(12) United States Patent
Buettner et al.

(10) Patent No.: US 7,812,136 B2
(45) Date of Patent: Oct. 12, 2010

(54) ANTIBODY OF HUMAN ORIGIN SPECIFICALLY BINDING TO ACTIVATED STATE OF PLATELET INTEGRIN RECEPTOR GPIIB/IIIA

(75) Inventors: Claudia Buettner, Schwetzingen (DE); Stefan Knackmuss, Plankstadt (DE); Melvyn Little, Neckargemünd (DE); Karlheinz Peter, Heidelberg (DE); Peter Roettgen, Ladenburg (DE); Meike Schwarz, Freiburg (DE)

(73) Assignee: Affimed Therapeutics, AG, Heidelberg (DE)

( * ) Notice: Subject to any disclaimer, the term of this patent is extended or adjusted under 35 U.S.C. 154(b) by 805 days.

(21) Appl. No.: 10/491,766

(22) PCT Filed: Oct. 4, 2002

(86) PCT No.: PCT/EP02/11154

§ 371 (c)(1),
(2), (4) Date: Dec. 9, 2004

(87) PCT Pub. No.: WO03/031476

PCT Pub. Date: Apr. 17, 2003

(65) Prior Publication Data

US 2007/0218067 A1   Sep. 20, 2007

(30) Foreign Application Priority Data

Oct. 5, 2001   (EP)   ................................. 01123851

(51) Int. Cl.
*C07K 16/28*   (2006.01)
(52) U.S. Cl. ............................... 530/388.22; 530/387.1; 530/388.1; 530/388.15; 530/388.2; 530/388.7
(58) Field of Classification Search ........................ None
See application file for complete search history.

(56) References Cited

U.S. PATENT DOCUMENTS

| | | | |
|---|---|---|---|
| 6,265,150 B1 * | 7/2001 | Terstappen et al. | ............. 435/5 |
| 6,790,938 B1 * | 9/2004 | Berchtold et al. | ...... 530/388.22 |
| 6,955,900 B1 * | 10/2005 | Barbas et al. | ............. 435/69.7 |
| 2003/0219434 A1 * | 11/2003 | Carter et al. | ............. 424/141.1 |

FOREIGN PATENT DOCUMENTS

EP        0 557 535 A1   9/1992

OTHER PUBLICATIONS

Schwarz et al., The FASEB Journal 18:12 express article 10.1096/fj.04-151fje, published online Sep. 16, 2004.*
Rudikoff et al., Proc Natl Acad Sci USA 79: 1979-1983, 1982.*
Colman, Research in Immunology 145: 33-36, 1994.*
Kussie et al., J. Immunol. 152: 146-152, 1994.*
Chen et al., EMBO J., 14: 2784-2794, 1995.*
Nurden et al., Blood 88: 887-899, 1996.*
Schwarz et al., The FASEB Journal express article 10.1096/fj.04-1513fje. Published online Sep. 16, 2004.*
Chung et al. The FASEB Journal express article 10.1096/fj.03-0586fje. Published online Dec. 19, 2003.*
Bedner, et al., "Identification of Low Molecular Weight GP Iib/Iia Antgonists That Bind Preferentially to Activated Platelets", *M. Pharmacology*, 285(3):1317-1326 (1998).
Berkowitz. "Current knowledge of the Platelet Glycoprotein Iib/IIIa Receptor Antagonists for the Treatment of Coronary Artery Disease", *Haemostatis* 30(Supp 3):27-43 (2000).
Bhatt and Topol, "Current Role of Platelet Glycoprotein Iib/IIIa Inhibitors in Acute Coronary Syndromes". *JAMA* 284(12):1549-1558 (2000).
Chew, et al., "Increased Mortality with Oral Platelet Glycoprotein IIb/IIIa Antagonists", *Circulation* 103(2):201-206 (2001).
Cohen, "Platelet Glycoprotein IIb/IIIa Receptor Inhibitors in Coronary Artery Disease", *Ann Intern. Med.* 124:843-844 (1996).
Colcher, et al, "Characterization an Biodistribution of Recombinant and Recombinatn/Chimeric Constructs of Monoclonal Antibody B72.3", *Cancer Research* 49:1732-1745, (1989).
Coller, et al, "A Murine Monoclonal Antibody That Completely Blocks the Binding of Fibrinogen to Platelets Produces a Thrombasthenic-like State in Normal Platelets and Binds to Glycoproteins Iib and/or IIIa". *J. Clin. Invest.* 72:325-338 (1983).
Davis, "Advances in the use of recombinant baculoviruses for the expression of heterologous proteins", *Curr. Opin. Biotech* 6:543-547 (1995).
Domesh, et al., "Advancing the Battle Against Acute Ischemic Syndromes: A Focus on the GP Iib-IIIa Inhibitors", *Pharmacology* 18(4):663-685 (1998).
Gawaz, M., Therapie bei koronarer Herzerkrankurg Stuttgart, New York, Thieme (1999), Table of Contents only.
Hillegass, et al., Glycoprotein Iib/IIIa Receptor Therapy in Percutaneous Coronary Intervention and Non-ST-Segment Elevation Acute Coronary Syndromes, *Pharmacoeconomics* 19(1):41-55 (2001).
Holmgren, "Thioredoxin", *Ann. Rev. Biochem*, 54:237-271 (1985).
Hoogenboom and Chames, "Natural and designer binding sites made by phage display technology", *Imm. Today* 21(8):371-377 (2000).
Jacobin, et al., "Human IgG Monoclonal Anti-$\alpha_{5b}\beta_3$-Binding Fragments Derived from Immunized Donors Using Phage Display", *J. Immun.* 168:2035-2045 (2002).
Jubellner, et al., "Acute Profound Thromobocytopenia Following C7E3 Fab (Abciximab) Therapy: Case Reports, Review of the Literature and Implications for Therapy", *Am. J. Hematol.* 61:205-208 (1999).

(Continued)

*Primary Examiner*—Phillip Gambel
(74) *Attorney, Agent, or Firm*—Howrey LLP

(57) ABSTRACT

The present invention is directed to an antibody or derivative thereof of human origin for inhibiting platelet aggregation, characterized in that it is effective by substantially exclusive binding to the activated state of platelet integrin receptor GPIIb/IIIa.

7 Claims, 31 Drawing Sheets

OTHER PUBLICATIONS

Kunick; et al., "A Molecular Basis for Affinity Modulation of Fab Ligand Binding to Intergrin $\alpha5b\beta_3$", *J. Bio. Chem.* 271(34):20315-20321 (1996).

LaVallie, et al., "A Thioredoxin Gene Fusion Expression System That Circumvents Inclusion Body Formation in the *E. coli* Cytoplasm", *Biotechnology* 11:187-193, 1993.

Nguyen-Ho and Lakkis, "Platelet Glycoprotein Iib/IIIa Receptor Antagonists and Coronary Artery Disease", *Current Astherosclerosis Reports* 3:139-148 (2001).

Peter, et al., "Induction of Fibrinogen Binding and Platelet Aggregation as a Potential Intrinsic Property of Various Glycoprotein Iib/IIIa ($\alpha5b\beta_3$) Inhibitors", Blood 92(9):3240-3249, 1998.

Sambrook, et al., Molecular Cloning—A Laboratory Manual, Cold Spring Harbor (1989), pp. XI-XXXVIII only.

Shattil, et al., "Changes in the Platelet Membrane Glycoprotein IIb IIIa Complex during Platelet Activation", *J. Bio. Chem.* 260(20):11107-11114 (1985).

Suzuki, et al., "Comparison of the antiplatelet effect of YM337 and abciximab in rhesus monkeys", *European J. Phar.* 336:169-176 (1997).

Topol, et al., "Platelet GPIIb-IIIa blockers", *Lancet* 353(9148):227-231, 1999.

Wong, "Advances in the use of *Bacillus subtilis* for the expression and secretion of heterologous proteins", *Curr. Opin. Bio.* 6:514-522 (1995).

* cited by examiner

SEQ No. 1

```
          NcoI
  1 ccatggcgga agtgcagctg gtgcagtctg gagctgaggt gaataagcct ggggcctcag
 61 tgaaggtctc ctgcaaggct tctggataca ccttcaccgg ctactatatg cactgggtgc
121 gacaggcccc tggacaaggg cttgagtgga tgggatggat caaccctaac agtggtggca
181 caaactatgc acagaagttt cagggctggg tcaccatgac cagggacacg tccatcagca
241 ccgcctacat ggagctgagc aggctgagat ctgacgacac ggccgtgtat tactgtgcga
301 gaggccgtgc tttgtataac cggaacgacc ggtccccaa ctggttcgac ccctggggcc
                                                                HindIII
361 agggaaccct ggtcaccgtc tcctcaggga gtgcatccgc cccaacccct aagcttgaag
          MluI
421 aaggtgaatt ttcagaagca cgcgtacagg ctgtgctgac tcagccgccc tcggtgtcag
481 tggccccagg acagacggcc aggattacct gtgggggaaa caacattgga agtaaaagtg
541 tgcagtggta ccagcagaag ccaggccagg cccctgtgct ggtcgtctat gatgatagcg
601 accggccctc agggatccct gagcgattct ctggctccaa ctctgggaac atggccaccc
661 tgaccatcag cagggtcgaa gccggggatg aggccgacta ttactgtcag gtgtgggata
721 gtagtagtga tcatgtggta ttcggcggag ggaccaagct gaccgtccta ggtcagccca
                                                                  NotI
781 aggctgcccc ctcggtcact ctgttcccgc cgtccgcggc cgc
```

Fig. 2a

Translation of MB9

```
  1 MAEVQLVQSG AEVNKPGASV KVSCKASGYT FTGYYMHWVR QAPGQGLEWM
 51 GWINPNSGGT NYAQKFQGWV TMTRDTSIST AYMELSRLRS DDTAVYYCAR
101 GRALYNRNDR SPNWFDPWGQ GTLVTVSSGS ASAPTLKLEE GEFSEARVQA
151 VLTQPPSVSV APGQTARITC GGNNIGSKSV QWYQQKPGQA PVLVVYDDSD
201 RPSGIPERFS GSNSGNMATL TISRVEAGDE ADYYCQVWDS SSDHVVFGGG
251 TKLTVLGQPK AAPSVTLFPP SAAAGSHHHH HH*
```

Fig. 2b

C9 scFv:                                                                (Seq. No. 2)
         NcoI
     1  ccatggcgca ggtacagctg caggagtctg ggggaggcgt ggtccagcct gggaggtccc
    61  tgagactctc ctgtgcagcc tctggattct ccttcagtaa ttatggcata cactgggtcc
   121  gccaggctcc aggcaagggg ctggagtggg tggcacttat atcatatgat ggaaataaga
   181  aattctatgc agactccgtg aagggccgat tcgccatctc cagagacact tctaagaata
   241  cggtggatct gcaaatgacc agcctgagac ctgaggacac ggctgtatat tactgtcga
   301  aatctggggg tattgccttg tactgggggg aatttgacta ctggggccag ggaaccctgg
                                                     HindIII
   361  tcaccgtctc ctcagcctcc accaagggcc aaagcttga agaaggtgaa ttttcagaag
         MluI
   421  cacgcgtatc ctatgaactg actcagccac cctcggtgtc agtggcccca ggacagacgg
   481  ccatgattac ctgtggggga aacaacattg gaagtacaac cgtgcactgg tatcagcaga
   541  agccaggcca ggcccctgtg ctggtcgtct atgatgataa cgagcgaccc tcagggatcc
   601  ctgagcgatt ctctggctcc aactctggga gcacggccac cctgaccatc aacagggtcg
   661  aagccgggga tgaggccgac tattattgtc aagtgtggga tagtggtagt gatcatgtgg
   721  tattcggcgg agggacgaag ctgaccgtcc taggtcagcc caaggctgcc cctcggtca
                                                     NotI
   781  ctctgttccc gccctcctct gcggccgc E4 scFv:                                                                (Seq. No. 3)
         NcoI
     1  ccatggcgca ggtgcagctg caggagtctg ggggaggctt ggtacagcct gggggtccc
    61  tgagactctc ctgtgcagcc tctggattca tgtttagcag gtatgccatg agctgggtcc
   121  gccaggctcc agggaagggg ccagagtggg tctcaggtat tagtggtagt ggtggtagta
   181  catactacgc agactccgtg aagggccggt tcaccgtctc cagagacaat tccaagaaca
   241  cgctgtatct gcaaatgaac agcctgagag ccgaggacac ggccgtatat tactgtgcga
   301  aagatctggg ctactatggt tcggggagcc aacccttga gtactgggc cagggaactc
                                                     HindIII
   361  tggtcaccgt ctcctcaggg agtgcatccg ccccaaagct tgaagaaggt gaattttcag
         MluI
   421  aagcacgcgt atctgaactg actcaggacc ctgctgtgtc tgtggccttg ggacagacag
   481  tcaggatcac atgccaagga gacagcctca gaaacttta tgcaagctgg taccagcaga
   541  agccaggaca ggcccctact cttgtcatct atggttaag taaaggccc tcagggatcc
   601  cagaccgatt ctctgcctcc agctcaggaa acacagcttc cttgaccatc actggggctc
   661  aggcggaaga tgaggctgac tattactgta actcccggga cagaagtggt aatcatgtaa
   721  atgtgctatt cggcggaggg accaagctga ccgtcctacg tcagcccaag gctgccccct
                                                     NotI
   781  cggtcactct gttcccgccc tcttctgcgg ccgc Figure 3: DNA sequence of C9 and E4 scFv masterframeworks
Restriction endonuclease recognition sequences flanking heavy and light chains (NcoI, HindIII and MluI, NotI respectively) are indicated.

Oligonucleotides used for the construction of the human scFv based synthetic antibody library. *BbsI* restriction enzyme recognition sites are indicated in bold style cut sites are underlined.

| vector construction | library construction |
|---|---|
| C9/VHCDR1.2/back/cut (#27):<br>TAC TAC GAA GAC GTG TCC TCA GGT CTC AGG CTG GTC<br>E4/VHCDR1.2/back/cut (#28):<br>TAC TAC GAA GAC GTG TCC TCG GCT CTC AGG CTG TTC<br>VH/for/cut (#29):<br>AAT GCA GGT ATC ACG AGG CCC TTT CGT CTT C<br><br>VL/back/cut (#24):<br>CAG CTC TGA TAT CTT TGG ATC CGT TTA GGT CTT CTT CTG<br>C9/VL/for/cut (#25):<br>TAC TAC GAA GAC TGG TCA CCG TCT CCT CAG CCT CCA<br>E4/VL/for/cut (#26):<br>TAC TAC GAA GAC TGG TCA CCG TCT CCT CAG GGA GTG<br><br>VHCDR3/stuff/for (#32):<br>GGA CAC GTC TTC AGC GCT GAG CTC GAA GAC TG<br>VHCDR3/stuff/back (#33):<br>TGA CCA GTC TTC GAG CTC AGC GCT GAA GAC GT | VHCDR3_3.4/cut:<br>GAG GAC ACG GCT GTA TAT TAC TGT GCG ARA (NNK)4 TTT GAS TAC TGG GGC CAG GGA ACC CTG GTC ACC<br>VHCDR3_3.5/cut:<br>GAG GAC ACG GCT GTA TAT TAC TGT GCG ARA (NNK)5 TTT GAS TAC TGG GGC CAG GGA ACC CTG GTC ACC<br>VHCDR3_3.6/cut:<br>GAG GAC ACG GCT GTA TAT TAC TGT GCG ARA (NNK)6 TTT GAS TAC TGG GGC CAG GGA ACC CTG GTC ACC<br>VHCDR3_3.7/cut:<br>GAG GAC ACG GCT GTA TAT TAC TGT GCG ARA (NNK)7 TTT GAS TAC TGG GGC CAG GGA ACC CTG GTC ACC<br><br>VHCDR3_for/cut:<br>AGC CTG GAA GAC GAG GAC ACG GCT GTA TAT TAC TGT GCG A<br>VHCDR3_back/cut:<br>GGC TGA GAA GAC GGT GAC CAG GGT TCC CTG GCC CCA GTA<br><br>VHCDR3_ev1/for/cut (#42):<br>AGC CTG GAA GAC GAG GAC ACG GCY GTG TAT TAC TGT<br>VHCDR3_ev2/for/cut (#43):<br>AGC CTG GAA GAC GAG GAC ACW GCC GTG TAT TAC TGT<br>VHCDR3_ev3/for/cut (#44):<br>AGC CTG GAA GAC GAG GAC ACG GCC GTA TAT TAC TGT<br>VHCDR3_ev/back/cut (#45):<br>GGC TGA GAA GAC GGT GAC CAG GGT KCC CTG GCC CCA |

Fig. 4

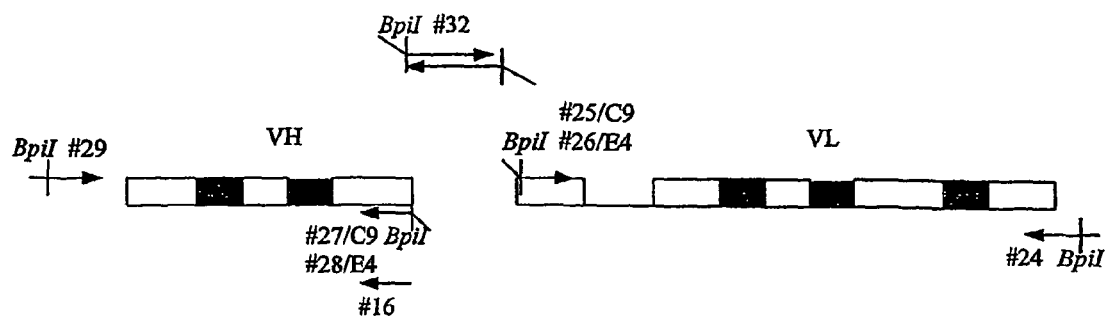

Schematic representation of annealing positions of oligonucleotides used for the construction of pEXHAM4/C9 and pEXHAM4/E4. Genes of the scFv's C9 and E4 cloned in pEXHAM1 are shown as boxes. Black painted areas represent CDR regions; Oligonucleotides are represented by arrows and identified by numbers (Fig. 4). BpiI restriction endonuclease recognition sites are indicated.

Fig. 5

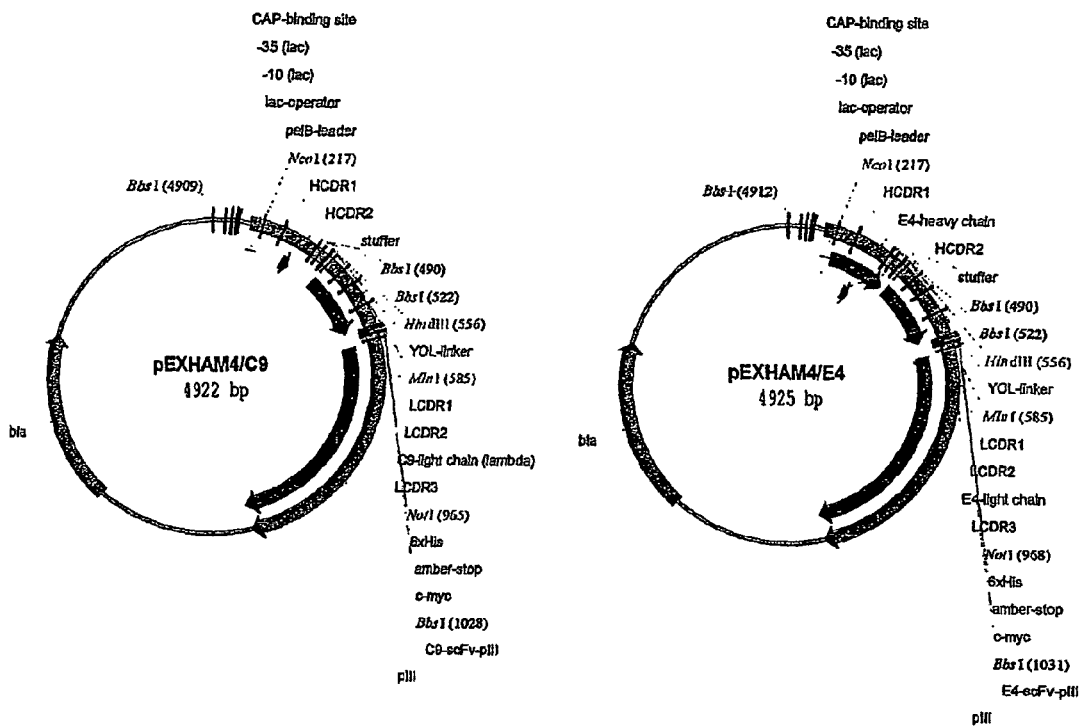
Figure 6: Vectormaps of pEXHAM4/C9 and pEXHAM4/E4
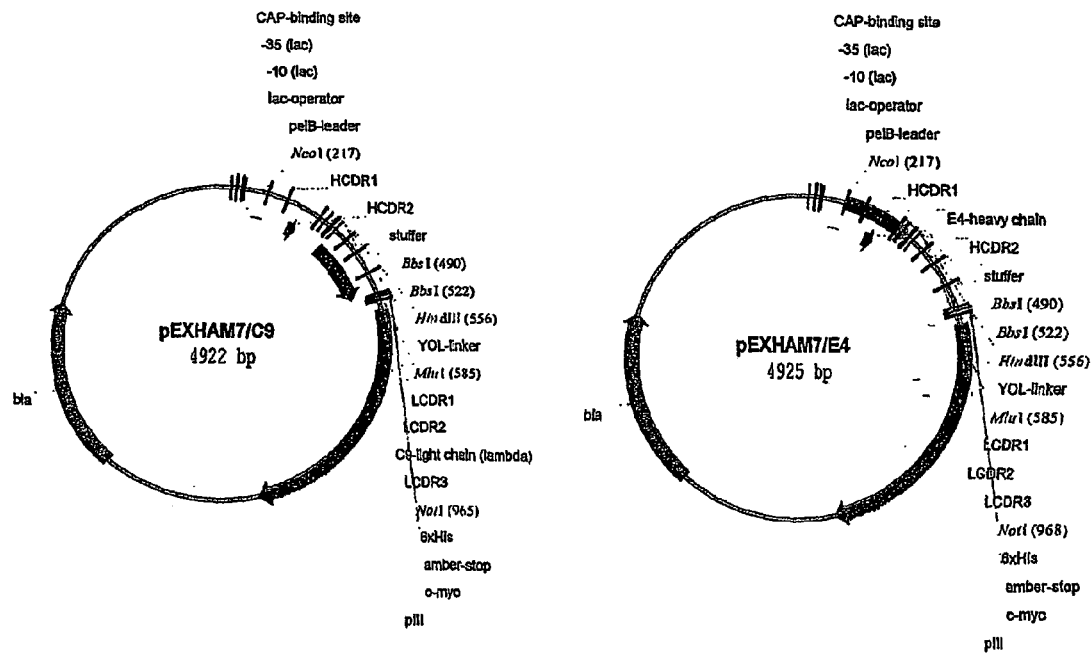
Figure 7: Vectormaps of pEXHAM7/C9 and pEXHAM7/E4

| Oligonucleotides used as primers in 1. PCR for amplification of human heavy and light chain variable regions | |
|---|---|
| heavy chain primer | light chain primer |
| VH-1a. 9 CAG GTG CAG CTG GTG CAG TCT | Vλ-1a 28 CAG TCT GTG CTG ACG CAG CCA 39 |
| VH-1b. 10 CAG GTC CAG CTT GTG CAG TCT | Vλ-1b 29 CAG TCT GTG CTG ACG CAG CCG |
| VH-1c. 11 CAG GTC CAG CTG GTA CAG TCT | Vλ-2 30 CAG TCT GCC CTG ACT CAG CCT |
| VH-1d. 12 GAG GTC CAG CTG GTA CAG TCT | Vλ-3a. 31 TCC TAT GAG CTG ACA CAG CCA |
| VH-1e. 13 CAG ATG CAG CTG GTA CAG TCT | Vλ-3b. 32 TCC TCT GAG CTG ACA CAG GAC |
| VH-2a. 14 CAG GTC ACC TTG AAG GAG TCT | Vλ-3c. 33 TCC TAT GTG CTG ACA CAG CCA |
| VH-2b. 15 CAG GTC ACC TTG AAG GAG TCT | Vλ-3d. 34 TCC TAT GAG CTG ACA CAG CTA |
| VH-3a. 16 GAA GTG CAG CTG GTG GAG TCT | Vλ-3e. 35 TCC TAT GAG CTG ATG CAG CCA |
| VH-3b. 17 CAG GTG CAG CTG GTG GAG TCT | Vλ-4a. 36 CTG CCT GTG CTG ACT CAG CCC |
| VH-3c. 18 GAG GTG CAG CTG TTG GAG TCT | Vλ-4b. 37 CAG CCT GTG CTG ACT CAA TCA |
| VH-4a. 19 CAG GTG CAG CTG CAG GAG TCG | Vλ-4c. 38 CAG CTT GTG CTG ACT CAA TCG |
| VH-4b. 20 CAG GTG CAG CTG CAG GAG TCG | Vλ-5a. 39 CAG CCT GTG CTG ACT CAG CCA |
| VH-4c. 21 CAG GTG CAG CTA CAG CAG TGG | Vλ-5b. 40 CAG GCT GTG CTG ACT CAG CCG |
| VH-5 22 GAA GTG CAG CTG GTG CAG TCT | Vλ-6 41 AAT TTT ATG CTG ACT CAG CCC |
| VH-6 23 CAG GTA CAG CTG CAG CAG TCA | Vλ-7a 42 CAG ACT GTG GTG ACT CAG GAG |
| VH-7 24 CAG GTG CAG CTG GTG CAA TCT | Vλ-7b 43 CAG GCT GTG GTG ACT CAG GAG |
| | Vλ-8 44 CAG ACT GTG GTG ACC CAG GAG |
| IgM 25 AAG GGT TGG GGC GGA TGC ACT 38 | Vλ-9 45 CAG CCT GTG CTG ACT CAG CCA |
| | Vλ-10 46 CAG GCA GGG CTG ACT CAG CCA |
| | Vκ-1a. 47 GAC ATC CAG ATG ACC CAG TCT |
| | Vκ-1b. 48 AAC ATC CAG ATG ACC CAG TCT |
| | Vκ-1c. 49 GCC ATC CAG TTG ACC CAG TCT |
| | Vκ-1d. 50 GAC ATC CAG TTG ACC CAG TCT |
| | Vκ-1e. 51 GCC ATC CGG ATG ACC CAG TCT |
| | Vκ-1f. 52 GTC ATC TGG ATG ACC CAG TCT |
| | Vκ-1g. 53 GCC ATC CAG ATG ACC CAG TCT |
| | Vκ-2a. 54 GAT ATT GTG ATG ACC CAG ACT |
| | Vκ-2b. 55 GAT ATT GTG ATG ACT CAG TCT |
| | Vκ-2c. 56 GAT ATT GTG ATG ACC CAG TCT |
| | Vκ-3a. 57 GAA ATT GTG TTG ACG CAG TCT |
| | Vκ-3b. 58 GAA ATT GTG ATG ACG CAG TCT |
| | Vκ-3c. 59 GAA ATT GTA ATG ACG CAG TCT |
| | Vκ-4 60 GAC ATC GTG ATG ACC CAG TCT |
| | Vκ-5 61 GAA ACG ACA CTC ACG CAG TCT |
| | Vκ-6a. 62 GAA ATT GTG CTG ACT CAG TCT |
| | Vκ-6b. 63 GAT GTT GTG ATG ACA CAG TCT |
| | Cλ 64 GGA CGG CGG GAA CAG AGT GAC |
| | Cκ 65 GAC AGA TGG TGC AGC CAC AGT 76 |

Fig. 8

Oligonucleotides used as primers in 2. PCR for introduction of restriction endonuclease recognition sequences (marked in bold style)

| | heavy chain primer | | light chain primer |
|---|---|---|---|
| | NcoI | | MluI |
| VH-1a. | TGG ACG CCC ATG GCG CAG GTG CAG CTG GTG CAG TCT | Vλ-1a. | CCT ACA GAA CGC GTA CAG TCT GTG CTG ACG CAG CCA |
| VH-1b. | TGG ACG CCC ATG GCG CAG GTC CAG CTT GTG CAG TCT | Vλ-1b. | CCT ACA GAA CGC GTA CAG TCT GTG CTG ACG CAG CCG |
| VH-1c. | TGG ACG CCC ATG GCG CAG GTC CAG CTG GTA CAG TCT | Vλ-2. | CCT ACA GAA CGC GTA CAG TCT GCC CTG ACT CAG CCT |
| VH-1d. | TGG ACG CCC ATG GCG CAG GTC CAG GTC CAG GTA CAG TCT | Vλ-3a. | CCT ACA GAA CGC GTA TCC TAT GAG CTG ACA CAG CCA |
| VH-1e. | TGG ACG CCC ATG GCG CAG ATG CAG CTG GTG CAG TCT | Vλ-3b. | CCT ACA GAA CGC GTA TCC TCT GAG CTG ACA CAG GAC |
| VH-2a. | TGG ACG CCC ATG GCG CAG ATC ACC TTG AAG GAG TCT | Vλ-3c. | CCT ACA GAA CGC GTA TCC TAT GTG CTG ACA CAG CCA |
| VH-2b. | TGG ACG CCC ATG GCG CAG GTC ACC TTG AAG GAG TCT | Vλ-3d. | CCT ACA GAA CGC GTA TCC TAT GAG CTG ACA CAG CTA |
| VH-3a. | TGG ACG CCC ATG GCG GAA GTG CAG CTG GTG GAG TCT | Vλ-3e. | CCT ACA GAA CGC GTA TCC TAT GAG CTG ATG CAG CCA |
| VH-3b. | TGG ACG CCC ATG GCG CAG GTG CAG CTG GTG GAG TCT | Vλ-4a. | CCT ACA GAA CGC GTA CTG CCT GTG CTG ACT CAG CCC |
| VH-3c. | TGG ACG CCC ATG GCG GAG GTG CAG CTG TTG GAG TCT | Vλ-4b. | CCT ACA GAA CGC GTA CAG CCT GTG CTG ACT CAA TCA |
| VH-4a. | TGG ACG CCC ATG GCG CAG GTG CAG CTG CAG GAG TCG | Vλ-4c. | CCT ACA GAA CGC GTA CAG CTT GTG CTG ACT CAA TCG |
| VH-4b. | TGG ACG CCC ATG GCG CAG CTG CAG CTG CAG GAG TGG | Vλ-5a. | CCT ACA GAA CGC GTA CAG CCT GTG CTG ACT CAG CCA |
| VH-4c. | TGG ACG CCC ATG GCG CAG GTG CAG CTA CAG CAG TGG | Vλ-5b. | CCT ACA GAA CGC GTA CAG GCT GTG CTG ACT CAG CCG |
| VH-5 | TGG ACG CCC ATG GCG GAA GTG CAG CTG GTG CAG TCT | Vλ-6 | CCT ACA GAA CGC GTA AAT TTT ATG CTG ACT CAG CCC |
| VH-6 | TGG ACG CCC ATG GCG CAG GTA CAG CTG CAG CAG TCA | Vλ-7a. | CCT ACA GAA CGC GTA CAG ACT GTG GTG ACT CAG GAG |
| VH-7 | TGG ACG CCC ATG GCG CAG GTG CAG CTG GTG CAA TCT | Vλ-7b. | CCT ACA GAA CGC GTA CAG GCT GTG GTG ACC CAG GAG |
| | | Vλ-8 | CCT ACA GAA CGC GTA CAG ACT GTG GTG ACC CAG GAG |
| | HindIII | Vλ-9 | CCT ACA GAA CGC GTA CAG CCT GTG CTG ACT CAG CCA |
| IgM | TGG GAA AAG CTT AAG GGT TGG GGC GGA TGC ACT | Vλ-10 | CCT ACA GAA CGC GTA CAG GCA GGG CTG ACT CAG CCA |
| | | Vκ-1a. | CCT ACA GAA CGC GTA GAC ATC CAG ATG ACC CAG TCT |
| | | Vκ-1b. | CCT ACA GAA CGC GTA GAC ATC CAG ATG ACC CAG TCT |
| | | Vκ-1c. | CCT ACA GAA CGC GTA GCC ATC CAG TTG ACC CAG TCT |
| | | Vκ-1d. | CCT ACA GAA CGC GTA GAC ATC CAG TTG ACC CAG TCT |
| | | Vκ-1e. | CCT ACA GAA CGC GTA GCC ATC CGG ATG ACC CAG TCT |
| | | Vκ-1f. | CCT ACA GAA CGC GTA GTC ATC TGG ATG ACC CAG TCT |
| | | Vκ-1g. | CCT ACA GAA CGC GTA GCC ATC CAG ATG ACC CAG TCT |
| | | Vκ-2a. | CCT ACA GAA CGC GTA GAT ATT GTG ATG ACC CAG ACT |
| | | Vκ-2b. | CCT ACA GAA CGC GTA GAT ATT GTG ATG ACT CAG TCT |
| | | Vκ-3a. | CCT ACA GAA CGC GTA GAA ATT GTG TTG ACG CAG TCT |
| | | Vκ-3b. | CCT ACA GAA CGC GTA GAA ATT GTG ATG ACG CAG TCT |
| | | Vκ-3c. | CCT ACA GAA CGC GTA GAA ATT GTA ATG ACG CAG TCT |
| | | Vκ-4 | CCT ACA GAA CGC GTA GAC ATC GTG ATG ACC CAG TCT |
| | | Vκ-5 | CCT ACA GAA CGC GTA GAA ACG ACA CTC ACG CAG TCT |
| | | Vκ-6a. | CCT ACA GAA CGC GTA GAA ATT GTG CTG ACT CAG TCT |
| | | Vκ-6b. | CCT ACA GAA CGC GTA GAT GTT GTG ATG ACA CAG TCT |
| | | | NotI |
| | | C-λ | GGG CGG CAG GGC GGC CGC GGA CGG GAA CAG AGT GAC |
| | | C-κ | GGG CGG CGG GGC GGC CGC GAC AGA TGG TGC AGC CAC AGT TC |

Fig. 9

FACS analysis of clones SA8, SA10 and SA11.
Binding of indicated scFv's to activated (black curve) and not activated (grey curve) thrombocytes.

```
                                                   CAP-binding site                         -35 (lac)
  1   CTCGAGAGCG GGCAGTGAGC GCAACGCAAT TAATGTGAGT TAGCTCACTC ATTAGGCACC CCAGGCTTTA CACTTTATGC
      GAGCTCTCGC CCGTCACTCG CGTTGCGTTA ATTACACTCA ATCGAGTGAG TAATCCGTGG GGTCCGAAAT GTGAAATACG
                                                                                              E4-scFv-p
              -10 (lac)              lac-operator                                             pelB-lead
 81   TTCCGGCTCG TATGTTGTGT GGAATTGTGA GCGGATAACA ATTTCACACA GAATTCATTA AAGAGGAGAA ATTAACCATG
      AAGGCCGAGC ATACAACACA CCTTAACACT CGCCTATTGT TAAAGTGTGT CTTAAGTAAT TTCTCCTCTT TAATTGGTAC
                                                                              NcoI    E4-heavy chain
                                                      E4-scFv-pIII
                                                    pelB-leader
161   AAATACCTAT TGCCTACGGC AGCCGCTGGC TTGCTGCTGC TGGCAGCTCA GCCGGCCATG GCGCAGGTGC AGCTGCAGGA
      TTTATGGATA ACGGATGCCG TCGGCGACCG AACGACGACG ACCGTCGAGT CGGCCGGTAC CGCGTCCACG TCGACGTCCT
                                                      E4-scFv-pIII
                                                                                              HCDR1
                                      E4-heavy chain
241   GTCTGGGGGA GGCTTGGTAC AGCCTGGGGG GTCCCTGAGA CTCTCCTGTG CAGCCTCTGG ATTCATGTTT AGCAGGTATG
      CAGACCCCCT CCGAACCATG TCGGACCCCC CAGGGACTCT GAGAGGACAC GTCGGAGACC TAAGTACAAA TCGTCCATAC
                                                      E4-scFv-pIII
       HCDR1                                                                  HCDR2
                            E4-heavy chain
321   CCATGAGCTG GGTCCGCCAG GCTCCAGGGA AGGGGCCAGA GTGGGTCTCA GGTATTAGTG GTAGTGGTGG TAGTACATAC
      GGTACTCGAC CCAGGCGGTC CGAGGTCCCT TCCCCGGTCT CACCCAGAGT CCATAATCAC CATCACCACC ATCATGTATG
                                                      E4-scFv-pIII
            HCDR2
                                    E4-heavy chain
401   TACGCAGACT CCGTGAAGGG CCGGTTCACC GTCTCCAGAG ACAATTCCAA GAACACGCTG TATCTGCAAA TGAACAGCCT
      ATGCGTCTGA GGCACTTCCC GGCCAAGTGG CAGAGGTCTC TGTTAAGGTT CTTGTGCGAC ATAGACGTTT ACTTGTCGGA
                                                      E4-scFv-pIII
                       stuffer
                                                    E4-heavy chain
              BbsI                                                             HindIII
481   GAGAGCCGAG GACACGTCTT CAGCGCTGAG CTCGAAGACT GGTCACCGTC TCCTCAGGGA GTGCATCCGC CCCAAAGCTT
      CTCTCGGCTC CTGTGCAGAA GTCGCGACTC GAGCTTCTGA CCAGTGGCAG AGGAGTCCCT CACGTAGGCG GGGTTTCGAA
               BbsI
                                                      E4-scFv-pIII
                    YOL-linker                                E4-light chain
                              MluI
561   GAAGAAGGTG AATTTTCAGA AGCACGCGTA TCTGAACTGA CTCAGGACCC TGCTGTGTCT GTGGCCTTGG GACAGACAGT
      CTTCTTCCAC TTAAAAGTCT TCGTGCGCAT AGACTTGACT GAGTCCTGGG ACGACACAGA CACCGGAACC CTGTCTGTCA
                                                      E4-scFv-pIII
                                        LCDR1
                                                  E4-light chain
641   CAGGATCACA TGCCAAGGAG ACAGCCTCAG AAACTTTTAT GCAAGCTGGT ACCAGCAGAA GCCAGGACAG GCCCCTACTC
      GTCCTAGTGT ACGGTTCCTC TGTCGGAGTC TTTGAAAATA CGTTCGACCA TGGTCGTCTT CGGTCCTGTC CGGGGATGAG
                                                      E4-scFv-pIII
                              LCDR2
                                               E4-light chain
721   TTGTCATCTA TGGTTTAAGT AAAAGGCCCT CAGGGATCCC AGACCGATTC TCTGCCTCCA GCTCAGGAAA CACAGCTTCC
      AACAGTAGAT ACCAAATTCA TTTTCCGGGA GTCCCTAGGG TCTGGCTAAG AGACGGAGGT CGAGTCCTTT GTGTCGAAGG
                                                      E4-scFv-pIII
                                                                                  LCDR3
                                                 E4-light chain
801   TTGACCATCA CTGGGGCTCA GGCGGAAGAT GAGGCTGACT ATTACTGTAA CTCCCGGGAC AGAAGTGGTA ATCATGTAAA
      AACTGGTAGT GACCCCGAGT CCGCCTTCTA CTCCGACTGA TAATGACATT GAGGGCCCTG TCTTCACCAT TAGTACATTT
                                                      E4-scFv-pIII
        LCDR3
                                               E4-light chain
881   TGTGCTATTC GGCGGAGGGA CCAAGCTGAC CGTCCTACGT CAGCCCAAGG CTGCCCCCTC GGTCACTCTG TTCCCGCCCT
      ACACGATAAG CCGCCTCCCT GGTTCGACTG GCAGGATGCA GTCGGGTTCC GACGGGGGAG CCAGTGAGAC AAGGGCGGGA
             NotI                                  amber-st                              BbsI
                                                      E4-scFv-pIII
       E4-light chain           6xHis                                c-myc
961   CTTCTGCGGC CGCTGGATCC CATCACCATC ACCATCACTA GGAACAAAAG CTGATCTCAG AAGAAGACCT AAACGGATCC
      GAAGACGCCG GCGACCTAGG GTAGTGGTAG TGGTAGTGAT CCTTGTTTTC GACTAGAGTC TTCTTCTGGA TTTGCCTAGG
                                                      E4-scFv-pIII
                                                                pIII
1041  AAAGATATCA GAGCTGAAAC TGTTGAAAGT TGTTTAGCAA AATCCCATAC AGAAAATTCA TTTACTAACG TCTGGAAAGA
      TTTCTATAGT CTCGACTTTG ACAACTTTCA ACAAATCGTT TTAGGGTATG TCTTTTAAGT AAATGATTGC AGACCTTTCT
```

Fig. 11a

```
                                           E4-scFv-pIII
                                                pIII
1121   CGACAAAACT TTAGATCGTT ACGCTAACTA TGAGGGCTGT CTGTGGAATG CTACAGGCGT TGTAGTTTGT ACTGGTGACG
       GCTGTTTTGA AATCTAGCAA TGCGATTGAT ACTCCCGACA GACACCTTAC GATGTCCGCA ACATCAAACA TGACCACTGC
                                           E4-scFv-pIII
                                                pIII
1201   AAACTCAGTG TTACGGTACA TGGGTTCCTA TTGGGCTTGC TATCCCTGAA AATGAGGGTG GTGGCTCTGA GGGTGGCGGT
       TTTGAGTCAC AATGCCATGT ACCCAAGGAT AACCCGAACG ATAGGGACTT TTACTCCCAC CACCGAGACT CCCACCGCCA
                                           E4-scFv-pIII
                                                pIII
1281   TCTGAGGGTG GCGGTTCTGA GGGTGGCGGT ACTAAACCTC CTGAGTACGG TGATACACCT ATTCCGGGCT ATACTTATAT
       AGACTCCCAC CGCCAAGACT CCCACCGCCA TGATTTGGAG GACTCATGCC ACTATGTGGA TAAGGCCCGA TATGAATATA
                                           E4-scFv-pIII
                                                pIII
1361   CAACCCTCTC GACGGCACTT ATCCGCCTGG TACTGAGCAA AACCCCGCTA ATCCTAATCC TTCTCTTGAG GAGTCTCAGC
       GTTGGGAGAG CTGCCGTGAA TAGGCGGACC ATGACTCGTT TTGGGGCGAT TAGGATTAGG AAGAGAACTC CTCAGAGTCG
                                           E4-scFv-pIII
                                                pIII
1441   CTCTTAATAC TTTCATGTTT CAGAATAATA GGTTCCGAAA TAGGCAGGGG GCATTAACTG TTTATACGGG CACTGTTACT
       GAGAATTATG AAAGTACAAA GTCTTATTAT CCAAGGCTTT ATCCGTCCCC CGTAATTGAC AAATATGCCC GTGACAATGA
                                           E4-scFv-pIII
                                                pIII
1521   CAAGGCACTG ACCCCGTTAA AACTTATTAC CAGTACACTC CTGTATCATC AAAAGCCATG TATGACGCTT ACTGGAACGG
       GTTCCGTGAC TGGGGCAATT TTGAATAATG GTCATGTGAG GACATAGTAG TTTTCGGTAC ATACTGCGAA TGACCTTGCC
                                           E4-scFv-pIII
                                                pIII
1601   TAAATTCAGA GACTGCGCTT TCCATTCTGG CTTTAATGAG GATTTATTTG TTTGTGAATA TCAAGGCCAA TCGTCTGACC
       ATTTAAGTCT CTGACGCGAA AGGTAAGACC GAAATTACTC CTAAATAAAC AAACACTTAT AGTTCCGGTT AGCAGACTGG
                                           E4-scFv-pIII
                                                pIII
1681   TGCCTCAACC TCCTGTCAAT GCTGGCGGCG GCTCTGGTGG TGGTTCTGGT GGCGGCTCTG AGGGTGGTGG CTCTGAGGGT
       ACGGAGTTGG AGGACAGTTA CGACCGCCGC CGAGACCACC ACCAAGACCA CCGCCGAGAC TCCCACCACC GAGACTCCCA
                                           E4-scFv-pIII
                                                pIII
1761   GGCGGTTCTG AGGGTGGCGG CTCTGAGGGA GGCGGTTCGG GTGGTGGCTC TGGTTCCGGT GATTTTGATT ATGAAAAGAT
       CCGCCAAGAC TCCCACCGCC GAGACTCCCT CCGCCAAGCC CACCACCGAG ACCAAGGCCA CTAAAACTAA TACTTTTCTA
                                           E4-scFv-pIII
                                                pIII
1841   GGCAAACGCT AATAAGGGGG CTATGACCGA AAATGCCGAT GAAAACGCGC TACAGTCTGA CGCTAAAGGC AAACTTGATT
       CCGTTTGCGA TTATTCCCCC GATACTGGCT TTTACGGCTA CTTTTGCGCG ATGTCAGACT GCGATTTCCG TTTGAACTAA
                                           E4-scFv-pIII
                                                pIII
1921   CTGTCGCTAC TGATTACGGT GCTGCTATCG ATGGTTTCAT TGGTGACGTT TCCGGCCTTG CTAATGGTAA TGGTGCTACT
       GACAGCGATG ACTAATGCCA CGACGATAGC TACCAAAGTA ACCACTGCAA AGGCCGGAAC GATTACCATT ACCACGATGA
                                           E4-scFv-pIII
                                                pIII
2001   GGTGATTTTG CTGGCTCTAA TTCCCAAATG GCTCAAGTCG GTGACGGTGA TAATTCACCT TTAATGAATA ATTTCCGTCA
       CCACTAAAAC GACCGAGATT AAGGGTTTAC CGAGTTCAGC CACTGCCACT ATTAAGTGGA AATTACTTAT TAAAGGCAGT
                                           E4-scFv-pIII
                                                pIII
2081   ATATTTACCT TCCCTCCCTC AATCGGTTGA ATGTCGCCCT TTTGTCTTTG GCGCTGGTAA ACCATATGAA TTTTCTATTG
       TATAAATGGA AGGGAGGGAG TTAGCCAACT TACAGCGGGA AAACAGAAAC CGCGACCATT TGGTATACTT AAAAGATAAC
                                           E4-scFv-pIII
                                                pIII
2161   ATTGTGACAA AATAAACTTA TTCCGTGGTG TCTTTGCGTT TCTTTTATAT GTTGCCACCT TTATGTATGT ATTTTCTACG
       TAACACTGTT TTATTTGAAT AAGGCACCAC AGAAACGCAA AGAAAATATA CAACGGTGGA AATACATACA TAAAAGATGC
                     E4-scFv-pIII
                           pIII
2241   TTTGCTAACA TACTGCGTAA TAAGGAGTCT TAATGATCTA GAGGCCTGTG CTAATGATCA GCTAGCTTGA GGCATCAATA
       AAACGATTGT ATGACGCATT ATTCCTCAGA ATTACTAGAT CTCCGGACAC GATTACTAGT CGATCGAACT CCGTAGTTAT
2321   AAACGAAAGG CTCAGTCGAA AGACTGGGCC TTTCGTTTTA TCTGTTGTTT GTCGGTTAAC GTCGACCTGG CGTAATAGCG
       TTTGCTTTCC GAGTCAGCTT TCTGACCCGG AAAGCAAAAT AGACAACAAA CAGCCAATTG CAGCTGGACC GCATTATCGC
2401   AAGAGGCCCG CACCGATCGC CCTTCCCAAC AGTTGCGCAG CCTGAATGGC GAATGGGACG CGCCCTGTAG CGGCGCATTA
       TTCTCCGGGC GTGGCTAGCG GGAAGGGTTG TCAACGCGTC GGACTTACCG CTTACCCTGC GCGGGACATC GCCGCGTAAT
2481   AGCGCGGCGG GTGTGGTGGT TACGCGCAGC GTGACCGCTA CACTTGCCAG CGCCCTAGCG CCCGCTCCTT TCGCTTTCTT
       TCGCGCCGCC CACACCACCA ATGCGCGTCG CACTGGCGAT GTGAACGGTC GCGGGATCGC GGGCGAGGAA AGCGAAAGAA
2561   CCCTTCCTTT CTCGCCACGT TCGCCGGCTT TCCCCGTCAA GCTCTAAATC GGGGGCTCCC TTTAGGGTTC CGATTTAGTG
       GGGAAGGAAA GAGCGGTGCA AGCGGCCGAA AGGGGCAGTT CGAGATTTAG CCCCCGAGGG AAATCCCAAG GCTAAATCAC
```

Fig. 11b

```
2641  CTTTACGGCA CCTCGACCCC AAAAAACTTG ATTAGGGTGA TGGTTCACGT AGTGGGCCAT CGCCCTGATA GACGGTTTTT
      GAAATGCCGT GGAGCTGGGG TTTTTTGAAC TAATCCCACT ACCAAGTGCA TCACCCGGTA GCGGGACTAT CTGCCAAAAA
2721  CGCCCTTTGA CGTTGGAGTC CACGTTCTTT AATAGTGGAC TCTTGTTCCA AACTGGAACA ACACTCAACC CTATCTCGGT
      GCGGGAAACT GCAACCTCAG GTGCAAGAAA TTATCACCTG AGAACAAGGT TTGACCTTGT TGTGAGTTGG GATAGAGCCA
2801  CTATTCTTTT GATTTATAAG GGATTTTGCC GATTTCGGCC TATTGGTTAA AAAATGAGCT GATTTAACAA AAATTTAACG
      GATAAGAAAA CTAAATATTC CCTAAAACGG CTAAAGCCGG ATAACCAATT TTTTACTCGA CTAAATTGTT TTTAAATTGC
2881  CGAATTTTAA CAAAATATTA AGGTTACAA  TTTAGGTGGC ACTTTTCGGG GAAATGTGCG CGGAACCCCT ATTTGTTTAT
      GCTTAAAATT GTTTTATAAT TGCGAATGTT AAATCCACCG TGAAAAGCCC CTTTACACGC GCCTTGGGGA TAAACAAATA
2961  TTTTCTAAAT ACATTCAAAT ATGTATCCGC TCATGAGACA ATAACCCTGA TAAATGCTTC AATAATATTG AAAAAGGAAG
      AAAAGATTTA TGTAAGTTTA TACATAGGCG AGTACTCTGT TATTGGGACT ATTTACGAAG TTATTATAAC TTTTTCCTTC
                                                                   bla
3041  AGTATGAGTA TTCAACATTT CCGTGTCGCC CTTATTCCCT TTTTTGCGGC ATTTTGCCTT CCTGTTTTTG CTCACCCAGA
      TCATACTCAT AAGTTGTAAA GGCACAGCGG GAATAAGGGA AAAAACGCCG TAAAACGGAA GGACAAAAAC GAGTGGGTCT
                                                                   bla
3121  AACGCTGGTG AAAGTAAAAG ATGCTGAAGA TCAGTTGGGT GCACGAGTGG GTTACATCGA ACTGGATCTC AACAGCGGTA
      TTGCGACCAC TTTCATTTTC TACGACTTCT AGTCAACCCA CGTGCTCACC CAATGTAGCT TGACCTAGAG TTGTCGCCAT
                                                                   bla
3201  AGATCCTTGA GAGTTTTCGC CCCGAAGAAC GTTTTCCAAT GATGAGCACT TTTAAAGTTC TGCTATGTGG CGCGGTATTA
      TCTAGGAACT CTCAAAAGCG GGGCTTCTTG CAAAAGGTTA CTACTCGTGA AAATTTCAAG ACGATACACC GCGCCATAAT
                                                                   bla
3281  TCCCGTATTG ACGCCGGGCA AGAGCAACTC GGTCGCCGCA TACACTATTC TCAGAATGAC TTGGTTGAGT ACTCACCAGT
      AGGGCATAAC TGCGGCCCGT TCTCGTTGAG CCAGCGGCGT ATGTGATAAG AGTCTTACTG AACCAACTCA TGAGTGGTCA
                                                                   bla
3361  CACAGAAAAG CATCTTACGG ATGGCATGAC AGTAAGAGAA TTATGCAGTG CTGCCATAAC CATGAGTGAT AACACTGCGG
      GTGTCTTTTC GTAGAATGCC TACCGTACTG TCATTCTCTT AATACGTCAC GACGGTATTG GTACTCACTA TTGTGACGCC
                                                                   bla
3441  CCAACTTACT TCTGACAACG ATCGGAGGAC CGAAGGAGCT AACCGCTTTT TTGCACAACA TGGGGGATCA TGTAACTCGC
      GGTTGAATGA AGACTGTTGC TAGCCTCCTG GCTTCCTCGA TTGGCGAAAA AACGTGTTGT ACCCCCTAGT ACATTGAGCG
                                                                   bla
3521  CTTGATCGTT GGGAACCGGA GCTGAATGAA GCCATACCAA ACGACGAGCG TGACACCACG ATGCCTGTAG CAATGGCAAC
      GAACTAGCAA CCCTTGGCCT CGACTTACTT CGGTATGGTT TGCTGCTCGC ACTGTGGTGC TACGGACATC GTTACCGTTG
                                                                   bla
3601  AACGTTGCGC AAACTATTAA CTGGCGAACT ACTTACTCTA GCTTCCCGGC AACAATTAAT AGACTGGATG GAGGCGGATA
      TTGCAACGCG TTTGATAATT GACCGCTTGA TGAATGAGAT CGAAGGGCCG TTGTTAATTA TCTGACCTAC CTCCGCCTAT
                                                                   bla
3681  AAGTTGCAGG ACCACTTCTG CGCTCGGCCC TTCCGGCTGG CTGGTTTATT GCTGATAAAT CTGGAGCCGG TGAGCGTGGG
      TTCAACGTCC TGGTGAAGAC GCGAGCCGGG AAGGCCGACC GACCAAATAA CGACTATTTA GACCTCGGCC ACTCGCACCC
                                                                   bla
3761  TCTCGCGGTA TCATTGCAGC ACTGGGGCCA GATGGTAAGC CCTCCCGTAT CGTAGTTATC TACACGACGG GGAGTCAGGC
      AGAGCGCCAT AGTAACGTCG TGACCCCGGT CTACCATTCG GAGGGCATA  GCATCAATAG ATGTGCTGCC CCTCAGTCCG
                                                                   bla
3841  AACTATGGAT GAACGAAATA GACAGATCGC TGAGATAGGT GCCTCACTGA TTAAGCATTG GTAACTGTCA GACCAAGTTT
      TTGATACCTA CTTGCTTTAT CTGTCTAGCG ACTCTATCCA CGGAGTGACT AATTCGTAAC CATTGACAGT CTGGTTCAAA
3921  ACTCATATAT ACTTTAGATT GATTTAAAAC TTCATTTTTA ATTTAAAAGG ATCTAGGTGA AGATCCTTTT TGATAATCTC
      TGAGTATATA TGAAATCTAA CTAAATTTTG AAGTAAAAAT TAAATTTTCC TAGATCCACT TCTAGGAAAA ACTATTAGAG
4001  ATGACCAAAA TCCCTTAACG TGAGTTTTCG TTCCACTGAG CGTCAAGACC CGTAGAAAAG ATCAAAGGAT CTTCTTGAGA
      TACTGGTTTT AGGGAATTGC ACTCAAAAGC AAGGTGACTC GCAGTCTGGG GCATCTTTTC TAGTTTCCTA GAAGAACTCT
4081  TCCTTTTTTT CTGCGCGTAA TCTGCTGCTT GCAAACAAAA AAACCACCGC TACCAGCGGT GGTTTGTTTG CCGGATCAAG
      AGGAAAAAAA GACGCGCATT AGACGACGAA CGTTTGTTTT TTTGGTGGCG ATGGTCGCCA CCAAACAAAC GGCCTAGTTC
4161  AGCTACCAAC TCTTTTTCCG AAGGTAACTG GCTTCAGCAG AGCGCAGATA CCAAATACTG TCCTTCTAGT GTAGCCGTAG
      TCGATGGTTG AGAAAAAGGC TTCCATTGAC CGAAGTCGTC TCGCGTCTAT GGTTTATGAC AGGAAGATCA CATCGGCATC
4241  TTAGGCCACC ACTTCAAGAA CTCTGTAGCA CCGCCTACAT ACCTCGCTCT GCTAATCCTG TTACCAGTGG CTGCTGCCAG
      AATCCGGTGG TGAAGTTCTT GAGACATCGT GGCGGATGTA TGGAGCGAGA CGATTAGGAC AATGGTCACC GACGACGGTC
4321  TGGCGATAAG TCGTGTCTTA CCGGGTTGGA CTCAAGACGA TAGTTACCGG ATAAGGCGCA GCGGTCGGGC TGAACGGGGG
      ACCGCTATTC AGCACAGAAT GGCCCAACCT GAGTTCTGCT ATCAATGGCC TATTCCGCGT CGCCAGCCCG ACTTGCCCCC
4401  GTTCGTGCAC ACAGCCCAGC TTGGAGCGAA CGACCTACAC CGAACTGAGA TACCTACAGC GTGAGCTATG AGAAAGCGCC
      CAAGCACGTG TGTCGGGTCG AACCTCGCTT GCTGGATGTG GCTTGACTCT ATGGATGTCG CACTCGATAC TCTTTCGCGG
4481  ACGCTTCCCG AAGGGAGAAA GGCGGACAGG TATCCGGTAA GCGGCAGGGT CGGAACAGGA GAGCGCACGA GGGAGCTTCC
      TGCGAAGGGC TTCCCTCTTT CCGCCTGTCC ATAGGCCATT CGCCGTCCCA GCCTTGTCCT CTCGCGTGCT CCCTCGAAGG
4561  AGGGGGAAAC GCCTGGTATC TTTATAGTCC TGTCGGGTTT CGCCACCTCT GACTTGAGCG TCGATTTTTG TGATGCTCGT
      TCCCCCTTTG CGGACCATAG AAATATCAGG ACAGCCCAAA GCGGTGGAGA CTGAACTCGC AGCTAAAAAC ACTACGAGCA
4641  CAGGGGGGCG GAGCCTATGG AAAAACGCCA GCAACGCGGC CTTTTTACGG TTCCTGGCCT TTTGCTGGCC TTTGCTCAC
      GTCCCCCCGC CTCGGATACC TTTTTGCGGT CGTTGCGCCG GAAAAATGCC AAGGACCGGA AAACGACCGG AAAACGAGTG
4721  ATGTTCTTTC CTGCGTTATC CCCTGATTCT GTGGATAACC GTATTACCGC CTTTGAGTGA GCTGATACCG CTCGCCGCAG
      TACAAGAAAG GACGCAATAG GGGACTAAGA CACCTATTGG CATAATGGCG GAAACTCACT CGACTATGGC GAGCGGCGTC
```

Fig. 11c

```
4801  CCGAACGACC GAGCGCAGCG AGTCAGTGAG CGAGGAAGCG GAAGAGCGCC CAATACGCAA ACCGCCTCTC CCCGCGCGTT
      GGCTTGCTGG CTCGCGTCGC TCAGTCACTC GCTCCTTCGC CTTCTCGCGG GTTATGCGTT TGGCGGAGAG GGGCGCGCAA
4881  GGCCGATTCA TTAATGCAGG TATCACGAGG CCCTTTCGTC TTCAC
      CCGGCTAAGT AATTACGTCC ATAGTGCTCC GGGAAAGCAG AAGTG
                                                  ‾‾‾‾‾
                                                   BbsI
```

Fig. 11d

```
                                              CAP-binding site                               -35 (lac)
   1   CTCGAGAGCG GGCAGTGAGC GCAACGCAAT TAATGTGAGT TAGCTCACTC ATTAGGCACC CCAGGCTTTA CACTTTATGC
       GAGCTCTCGC CCGTCACTCG CGTTGCGTTA ATTACACTCA ATCGAGTGAG TAATCCGTGG GGTCCGAAAT GTGAAATACG
                                                                                          C9-scFv-p
             -10 (lac)              lac-operator                                          pelB-lead
  81   TTCCGGCTCG TATGTTGTGT GGAATTGTGA GCGGATAACA ATTTCACACA GAATTCATTA AAGAGGAGAA ATTAACCATG
       AAGGCCGAGC ATACAACACA CCTTAACACT CGCCTATTGT TAAAGTGTGT CTTAAGTAAT TTCTCCTCTT TAATTGGTAC
                                                  C9-scFv-pIII
                                   pelB-leader
                                                                Ncol
 161   AAATACCTAT TGCCTACGGC AGCCGCTGGC TTGCTGCTGC TGGCAGCTCA GCCGGCCATG GCGCAGGTAC AGCTGCAGGA
       TTTATGGATA ACGGATGCCG TCGGCGACCG AACGACGACG ACCGTCGAGT CGGCCGGTAC CGCGTCCATG TCGACGTCCT
                                                  C9-scFv-pIII
                                                                                            HCDR1
 241   GTCTGGGGGA GGCGTGGTCC AGCCTGGGAG GTCCCTGAGA CTCTCCTGTG CAGCCTCTGG ATTCTCCTTC AGTAATTATG
       CAGACCCCCT CCGCACCAGG TCGGACCCTC CAGGGACTCT GAGAGGACAC GTCGGAGACC TAAGAGGAAG TCATTAATAC
                                                  C9-scFv-pIII
          HCDR1                                                           HCDR2
 321   GCATACACTG GGTCCGCCAG GCTCCAGGCA AGGGGCTGGA GTGGGTGGCA CTTATATCAT ATGATGGAAA TAAGAAATTC
       CGTATGTGAC CCAGGCGGTC CGAGGTCCGT TCCCCGACCT CACCCACCGT GAATATAGTA TACTACCTTT ATTCTTTAAG
                                                  C9-scFv-pIII
           HCDR2
 401   TATGCAGACT CCGTGAAGGG CCGATTCGCC ATCTCCAGAG ACACTTCTAA GAATACGGTG GATCTGCAAA TGACCAGCCT
       ATACGTCTGA GGCACTTCCC GGCTAAGCGG TAGAGGTCTC TGTGAAGATT CTTATGCCAC CTAGACGTTT ACTGGTCGGA
                                    stuffer
                                                  C9-scFv-pIII
                           Bbsl                                                           HindIII
 481   GAGACCTGAG GACACGTCTT CAGCGCTGAG CTCGAAGACT GGTCACCGTC TCCTCAGCCT CCACCAAGGG CCCAAAGCTT
       CTCTGGACTC CTGTGCAGAA GTCGCGACTC GAGCTTCTGA CCAGTGGCAG AGGAGTCGGA GGTGGTTCCC GGGTTTCGAA
                           Bbsl
                                                        C9-light chain (lambda)
                                                  C9-scFv-pIII
          YOL-linker
                              Mlul
 561   GAAGAAGGTG AATTTTCAGA AGCACGCGTA TCCTATGAAC TGACTCAGCC ACCCTCGGTG TCAGTGGCCC CAGGACAGAC
       CTTCTTCCAC TTAAAAGTCT TCGTGCGCAT AGGATACTTG ACTGAGTCGG TGGGAGCCAC AGTCACCGGG GTCCTGTCTG
                                                     LCDR1
                                                  C9-scFv-pIII
                                                  C9-light chain (lambda)
 641   GGCCATGATT ACCTGTGGGG GAAACAACAT TGGAAGTACA ACCGTGCACT GGTATCAGCA GAAGCCAGGC CAGGCCCCTG
       CCGGTACTAA TGGACACCCC CTTTGTTGTA ACCTTCATGT TGGCACGTGA CCATAGTCGT CTTCGGTCCG GTCCGGGGAC
                                       LCDR2
                                                  C9-scFv-pIII
                                                  C9-light chain (lambda)
 721   TGCTGGTCGT CTATGATGAT AACGAGCGAC CCTCAGGGAT CCCTGAGCGA TTCTCTGGCT CCAACTCTGG GAGCACGGCC
       ACGACCAGCA GATACTACTA TTGCTCGCTG GGAGTCCCTA GGGACTCGCT AAGAGACCGA GGTTGAGACC CTCGTGCCGG
                                                                                     LCDR3
                                                  C9-scFv-pIII
                                                  C9-light chain (lambda)
 801   ACCCTGACCA TCAACAGGGT CGAAGCCGGG GATGAGGCGA CTATTATTG TCAAGTGTGG GATAGTGGTA GTGATCATGT
       TGGGACTGGT AGTTGTCCCA GCTTCGGCCC CTACTCCGGC TGATAATAAC AGTTCACACC CTATCACCAT CACTAGTACA
        LCDR3
                                                  C9-scFv-pIII
                                                  C9-light chain (lambda)
 881   GGTATTCGGC GGAGGGACGA AGCTGACCGT CCTAGGTCAG CCCAAGGCTG CCCCCTCGGT CACTCTGTTC CCGCCCTCCT
       CCATAAGCCG CCTCCCTGCT TCGACTGGCA GGATCCAGTC GGGTTCCGAC GGGGGAGCCA GTGAGACAAG GGCGGGAGGA
           Notl                        amber-st                      Bbsl
                                                  C9-scFv-pIII
        C9-light chain (lam           6xHis                          c-myc
 961   CTGCGGCCGC TGGATCCCAT CACCATCACC ATCACTAGGA ACAAAAGCTG ATCTCAGAAG AAGACCTAAA CGGATCCAAA
       GACGCCGGCG ACCTAGGGTA GTGGTAGTGG TAGTGATCCT TGTTTTCGAC TAGAGTCTTC TTCTGGATTT GCCTAGGTTT
                                                  C9-scFv-pIII
                                                          pIII
1041   GATATCAGAG CTGAAACTGT TGAAAGTTGT TTAGCAAAAT CCCATACAGA AAATTCATTT ACTAACGTCT GGAAAGACGA
       CTATAGTCTC GACTTTGACA ACTTTCAACA AATCGTTTTA GGGTATGTCT TTTAAGTAAA TGATTGCAGA CCTTTCTGCT
```

Fig. 12a

```
                                                C9-scFv-pIII
                                                    pIII
1121  CAAAACTTTA GATCGTTACG CTAACTATGA GGGCTGTCTG TGGAATGCTA CAGGCGTTGT AGTTTGTACT GGTGACGAAA
      GTTTTGAAAT CTAGCAATGC GATTGATACT CCCGACAGAC ACCTTACGAT GTCCGCAACA TCAAACATGA CCACTGCTTT
                                                C9-scFv-pIII
                                                    pIII
1201  CTCAGTGTTA CGGTACATGG GTTCCTATTG GGCTTGCTAT CCCTGAAAAT GAGGGTGGTG GCTCTGAGGG TGGCGGTTCT
      GAGTCACAAT GCCATGTACC CAAGGATAAC CCGAACGATA GGGACTTTTA CTCCCACCAC CGAGACTCCC ACCGCCAAGA
                                                C9-scFv-pIII
                                                    pIII
1281  GAGGGTGGCG GTTCTGAGGG TGGCGGTACT AAACCTCCTG AGTACGGTGA TACACCTATT CCGGGCTATA CTTATATCAA
      CTCCCACCGC CAAGACTCCC ACCGCCATGA TTTGGAGGAC TCATGCCACT ATGTGGATAA GGCCCGATAT GAATATAGTT
                                                C9-scFv-pIII
                                                    pIII
1361  CCCTCTCGAC GGCACTTATC CGCCTGGTAC TGAGCAAAAC CCCGCTAATC CTAATCCTTC TCTTGAGGAG TCTCAGCCTC
      GGGAGAGCTG CCGTGAATAG GCGGACCATG ACTCGTTTTG GGCGATTAG GATTAGGAAG AGAACTCCTC AGAGTCGGAG
                                                C9-scFv-pIII
                                                    pIII
1441  TTAATACTTT CATGTTTCAG AATAATAGGT TCCGAAATAG GCAGGGGCA TTAACTGTTT ATACGGGCAC TGTTACTCAA
      AATTATGAAA GTACAAAGTC TTATTATCCA AGGCTTTATC CGTCCCCGT AATTGACAAA TATGCCCGTG ACAATGAGTT
                                                C9-scFv-pIII
                                                    pIII
1521  GGCACTGACC CCGTTAAAAC TTATTACCAG TACACTCCTG TATCATCAAA AGCCATGTAT GACGCTTACT GGAACGGTAA
      CCGTGACTGG GGCAATTTTG AATAATGGTC ATGTGAGGAC ATAGTAGTTT TCGGTACATA CTGCGAATGA CCTTGCCATT
                                                C9-scFv-pIII
                                                    pIII
1601  ATTCAGAGAC TGCGCTTTCC ATTCTGGCTT TAATGAGGAT TTATTTGTTT GTGAATATCA AGGCCAATCG TCTGACCTGC
      TAAGTCTCTG ACGCGAAAGG TAAGACCGAA ATTACTCCTA AATAAACAAA CACTTATAGT TCCGGTTAGC AGACTGGACG
                                                C9-scFv-pIII
                                                    pIII
1681  CTCAACCTCC TGTCAATGCT GGCGGCGGCT CTGGTGGTGG TTCTGGTGGC GGCTCTGAGG GTGGTGGCTC TGAGGGTGGC
      GAGTTGGAGG ACAGTTACGA CCGCCGCCGA GACCACCACC AAGACCACCG CCGAGACTCC CACCACCGAG ACTCCCACCG
                                                C9-scFv-pIII
                                                    pIII
1761  GGTTCTGAGG GTGGCGGCTC TGAGGGAGGC GGTTCCGGTG GTGGCTCTGG TTCCGGTGAT TTTGATTATG AAAAGATGGC
      CCAAGACTCC CACCGCCGAG ACTCCCTCCG CCAAGGCCAC CACCGAGACC AAGGCCACTA AAACTAATAC TTTTCTACCG
                                                C9-scFv-pIII
                                                    pIII
1841  AAACGCTAAT AAGGGGGCTA TGACCGAAAA TGCCGATGAA AACGCGCTAC AGTCTGACGC TAAAGGCAAA CTTGATTCTG
      TTTGCGATTA TTCCCCCGAT ACTGGCTTTT ACGGCTACTT TTGCGCGATG TCAGACTGCG ATTTCCGTTT GAACTAAGAC
                                                C9-scFv-pIII
                                                    pIII
1921  TCGCTACTGA TTACGGTGCT GCTATCGATG GTTTCATTGG TGACGTTTCC GGCCTTGCTA ATGGTAATGG TGCTACTGGT
      AGCGATGACT AATGCCACGA CGATAGCTAC CAAAGTAACC ACTGCAAAGG CCGGAACGAT TACCATTACC ACGATGACCA
                                                C9-scFv-pIII
                                                    pIII
2001  GATTTTGCTG GCTCTAATTC CCAAATGGCT CAAGTCGGTG ACGGTGATAA TTCACCTTTA ATGAATAATT TCCGTCAATA
      CTAAAACGAC CGAGATTAAG GGTTTACCGA GTTCAGCCAC TGCCACTATT AAGTGGAAAT TACTTATTAA AGGCAGTTAT
                                                C9-scFv-pIII
                                                    pIII
2081  TTTACCTTCC CTCCCTCAAT CGGTTGAATG TCGCCCTTTT GTCTTTGGCG CTGGTAAACC ATATGAATTT TCTATTGATT
      AAATGGAAGG GAGGGAGTTA GCCAACTTAC AGCGGGAAAA CAGAAACCGC GACCATTTGG TATACTTAAA AGATAACTAA
                                                C9-scFv-pIII
                                                    pIII
2161  GTGACAAAAT AAACTTATTC CGTGGTGTCT TTGCGTTTCT TTTATATGTT GCCACCTTTA TGTATGTATT TTCTACGTTT
      CACTGTTTTA TTTGAATAAG GCACCACAGA AACGCAAAGA AAATATACAA CGGTGGAAAT ACATACATAA AAGATGCAAA
           C9-scFv-pIII
                 pIII
2241  GCTAACATAC TGCGTAATAA GGAGTCTTAA TGATCTAGAG GCCTGTGCTA ATGATCAGCT AGCTTGAGGC ATCAATAAAA
      CGATTGTATG ACGCATTATT CCTCAGAATT ACTAGATCTC CGGACACGAT TACTAGTCGA TCGAACTCCG TAGTTATTTT
2321  CGAAAGGCTC AGTCGAAAGA CTGGGCCTTT CGTTTTATCT GTTGTTTGTC GGTTAACGTC GACCTGGCGT AATAGCGAAG
      GCTTTCCGAG TCAGCTTTCT GACCCGGAAA GCAAAATAGA CAACAAACAG CCAATTGCAG CTGGACCGCA TTATCGCTTC
2401  AGGCCCGCAC CGATCGCCCT TCCCAACAGT TGCGCAGCCT GAATGGCGAA TGGGACGCGC CCTGTAGCGG CGCATTAAGC
      TCCGGGCGTG GCTAGCGGGA AGGGTTGTCA ACGCGTCGGA CTTACCGCTT ACCCTGCGCG GGACATCGCC GCGTAATTCG
2481  GCGGCGGGTG TGGTGGTTAC GCGCAGCGTG ACCGCTACAC TTGCCAGCGC CCTAGCGCCC GCTCCTTTCG CTTTCTTCCC
      CGCCGCCCAC ACCACCAATG CGCGTCGCAC TGGCGATGTG AACGGTCGCG GGATCGCGGG CGAGGAAAGC GAAAGAAGGG
2561  TTCCTTTCTC GCCACGTTCG CCGGCTTTCC CCGTCAAGCT CTAAATCGGG GGCTCCCTTT AGGGTTCCGA TTTAGTGCTT
      AAGGAAAGAG CGGTGCAAGC GGCCGAAAGG GGCAGTTCGA GATTTAGCCC CCGAGGGAAA TCCCAAGGCT AAATCACGAA
```

Fig. 12b

```
2641  TACGGCACCT CGACCCCAAA AAACTTGATT AGGGTGATGG TTCACGTAGT GGGCCATCGC CCTGATAGAC GGTTTTTCGC
      ATGCCGTGGA GCTGGGGTTT TTTGAACTAA TCCCACTACC AAGTGCATCA CCCGGTAGCG GGACTATCTG CCAAAAAGCG
2721  CCTTTGACGT TGGAGTCCAC GTTCTTTAAT AGTGGACTCT TGTTCCAAAC TGGAACAACA CTCAACCCTA TCTCGGTCTA
      GGAAACTGCA ACCTCAGGTG CAAGAAATTA TCACCTGAGA ACAAGGTTTG ACCTTGTTGT GAGTTGGGAT AGAGCCAGAT
2801  TTCTTTTGAT TTATAAGGGA TTTTGCCGAT TTCGGCCTAT TGGTTAAAAA ATGAGCTGAT TTAACAAAAA TTTAACGCGA
      AAGAAAACTA AATATTCCCT AAAACGGCTA AAGCCGGATA ACCAATTTTT TACTCGACTA AATTGTTTTT AAATTGCGCT
2881  ATTTTAACAA AATATTAACG CTTACAATTT AGGTGGCACT TTTCGGGGAA ATGTGCGCGG AACCCCTATT TGTTTATTTT
      TAAAATTGTT TTATAATTGC GAATGTTAAA TCCACCGTGA AAAGCCCCTT TACACGCGCC TTGGGGATAA ACAAATAAAA
2961  TCTAAATACA TTCAAATATG TATCCGCTCA TGAGACAATA ACCCTGATAA ATGCTTCAAT AATATTGAAA AAGGAAGAGT
      AGATTTATGT AAGTTTATAC ATAGGCGAGT ACTCTGTTAT TGGGACTATT TACGAAGTTA TTATAACTTT TTCCTTCTCA
                                                                                      bla
3041  ATGAGTATTC AACATTTCCG TGTCGCCCTT ATTCCCTTTT TTGCGGCATT TTGCCTTCCT GTTTTTGCTC ACCCAGAAAC
      TACTCATAAG TTGTAAAGGC ACAGCGGGAA TAAGGGAAAA AACGCCGTAA AACGGAAGGA CAAAAACGAG TGGGTCTTTG
                                                                                      bla
3121  GCTGGTGAAA GTAAAAGATG CTGAAGATCA GTTGGGTGCA CGAGTGGGTT ACATCGAACT GGATCTCAAC AGCGGTAAGA
      CGACCACTTT CATTTTCTAC GACTTCTAGT CAACCCACGT GCTCACCCAA TGTAGCTTGA CCTAGAGTTG TCGCCATTCT
                                                                                      bla
3201  TCCTTGAGAG TTTTCGCCCC GAAGAACGTT TTCCAATGAT GAGCACTTTT AAAGTTCTGC TATGTGGCGC GGTATTATCC
      AGGAACTCTC AAAAGCGGGG CTTCTTGCAA AAGGTTACTA CTCGTGAAAA TTTCAAGACG ATACACCGCG CCATAATAGG
                                                                                      bla
3281  CGTATTGACG CCGGGCAAGA GCAACTCGGT CGCCGCATAC ACTATTCTCA GAATGACTTG GTTGAGTACT CACCAGTCAC
      GCATAACTGC GGCCCGTTCT CGTTGAGCCA GCGGCGTATG TGATAAGAGT CTTACTGAAC CAACTCATGA GTGGTCAGTG
                                                                                      bla
3361  AGAAAAGCAT CTTACGGATG GCATGACAGT AAGAGAATTA TGCAGTGCTG CCATAACCAT GAGTGATAAC ACTGCGGCCA
      TCTTTTCGTA GAATGCCTAC CGTACTGTCA TTCTCTTAAT ACGTCACGAC GGTATTGGTA CTCACTATTG TGACGCCGGT
                                                                                      bla
3441  ACTTACTTCT GACAACGATC GGAGGACCGA AGGAGCTAAC CGCTTTTTTG CACAACATGG GGGATCATGT AACTCGCCTT
      TGAATGAAGA CTGTTGCTAG CCTCCTGGCT TCCTCGATTG GCGAAAAAAC GTGTTGTACC CCCTAGTACA TTGAGCGGAA
                                                                                      bla
3521  GATCGTTGGG AACCGGAGCT GAATGAAGCC ATACCAAACG ACGAGCGTGA CACCACGATG CCTGTAGCAA TGGCAACAAC
      CTAGCAACCC TTGGCCTCGA CTTACTTCGG TATGGTTTGC TGCTCGCACT GTGGTGCTAC GGACATCGTT ACCGTTGTTG
                                                                                      bla
3601  GTTGCGCAAA CTATTAACTG GCGAACTACT TACTCTAGCT TCCCGGCAAC AATTAATAGA CTGGATGGAG GCGGATAAAG
      CAACGCGTTT GATAATTGAC CGCTTGATGA ATGAGATCGA AGGGCCGTTG TTAATTATCT GACCTACCTC CGCCTATTTC
                                                                                      bla
3681  TTGCAGGACC ACTTCTGCGC TCGGCCCTTC CGGCTGGCTG GTTTATTGCT GATAAATCTG GAGCCGGTGA GCGTGGGTCT
      AACGTCCTGG TGAAGACGCG AGCCGGGAAG GCCGACCGAC CAAATAACGA CTATTTAGAC CTCGGCCACT CGCACCCAGA
                                                                                      bla
3761  CGCGGTATCA TTGCAGCACT GGGGCCAGAT GGTAAGCCCT CCCGTATCGT AGTTATCTAC ACGACGGGGA GTCAGGCAAC
      GCGCCATAGT AACGTCGTGA CCCCGGTCTA CCATTCGGGA GGGCATAGCA TCAATAGATG TGCTGCCCCT CAGTCCGTTG
                                                                                      bla
3841  TATGGATGAA CGAAATAGAC AGATCGCTGA GATAGGTGCC TCACTGATTA AGCATTGGTA ACTGTCAGAC CAAGTTTACT
      ATACCTACTT GCTTTATCTG TCTAGCGACT CTATCCACGG AGTGACTAAT TCGTAACCAT TGACAGTCTG GTTCAAATGA
3921  CATATATACT TTAGATTGAT TTAAAACTTC ATTTTTAATT TAAAAGGATC TAGGTGAAGA TCCTTTTTGA TAATCTCATG
      GTATATATGA AATCTAACTA AATTTTGAAG TAAAAATTAA ATTTTCCTAG ATCCACTTCT AGGAAAAACT ATTAGAGTAC
4001  ACCAAAATCC CTTAACGTGA GTTTTCGTTC CACTGAGCGT CAGACCCCGT AGAAAAGATC AAAGGATCTT CTTGAGATCC
      TGGTTTTAGG GAATTGCACT CAAAAGCAAG GTGACTCGCA GTCTGGGGCA TCTTTTCTAG TTTCCTAGAA GAACTCTAGG
4081  TTTTTTTCTG CGCGTAATCT GCTGCTTGCA AACAAAAAAA CCACCGCTAC CAGCGGTGGT TTGTTTGCCG GATCAAGAGC
      AAAAAAAGAC GCGCATTAGA CGACGAACGT TTGTTTTTTT GGTGGCGATG GTCGCCACCA AACAAACGGC CTAGTTCTCG
4161  TACCAACTCT TTTTCCGAAG GTAACTGGCT TCAGCAGAGC GCAGATACCA AATACTGTCC TTCTAGTGTA GCCGTAGTTA
      ATGGTTGAGA AAAAGGCTTC CATTGACCGA AGTCGTCTCG CGTCTATGGT TTATGACAGG AAGATCACAT CGGCATCAAT
4241  GGCCACCACT TCAAGAACTC TGTAGCACCG CCTACATACC TCGCTCTGCT AATCCTGTTA CCAGTGGCTG CTGCCAGTGG
      CCGGTGGTGA AGTTCTTGAG ACATCGTGGC GGATGTATGG AGCGAGACGA TTAGGACAAT GGTCACCGAC GACGGTCACC
4321  CGATAAGTCG TGTCTTACCG GGTTGGACTC AAGACGATAG TTACCGGATA AGGCGCAGCG GTCGGGCTGA ACGGGGGGTT
      GCTATTCAGC ACAGAATGGC CCAACCTGAG TTCTGCTATC AATGGCCTAT TCCGCGTCGC CAGCCCGACT TGCCCCCCAA
4401  CGTGCACACA GCCCAGCTTG GAGCGAACGA CCTACACCGA ACTGAGATAC CTACAGCGTG AGCTATGAGA AAGCGCCACG
      GCACGTGTGT CGGGTCGAAC CTCGCTTGCT GGATGTGGCT TGACTCTATG GATGTCGCAC TCGATACTCT TTCGCGGTGC
4481  CTTCCCGAAG GGAGAAAGGC GGACAGGTAT CCGGTAAGCG GCAGGGTCGG AACAGGAGAG CGCACGAGGG AGCTTCCAGG
      GAAGGGCTTC CCTCTTTCCG CCTGTCCATA GGCCATTCGC CGTCCCAGCC TTGTCCTCTC GCGTGCTCCC TCGAAGGTCC
4561  GGGAAACGCC TGGTATCTTT ATAGTCCTGT CGGGTTTCGC CACCTCTGAC TTGAGCGTCG ATTTTTGTGA TGCTCGTCAG
      CCCTTTGCGG ACCATAGAAA TATCAGGACA GCCCAAAGCG GTGGAGACTG AACTCGCAGC TAAAAACACT ACGAGCAGTC
4641  GGGGGCGGAG CCTATGGAAA AACGCCAGCA ACGCGGCCTT TTTACGGTTC CTGGCCTTTT GCTGGCCTTT TGCTCACATG
      CCCCCGCCTC GGATACCTTT TTGCGGTCGT TGCGCCGGAA AAATGCCAAG GACCGGAAAA CGACCGGAAA ACGAGTGTAC
4721  TTCTTTCCTG CGTTATCCCC TGATTCTGTG GATAACCGTA TTACCGCCTT TGAGTGAGCT GATACCGCTC GCCGCAGCCG
      AAGAAAGGAC GCAATAGGGG ACTAAGACAC CTATTGGCAT AATGGCGGAA ACTCACTCGA CTATGGCGAG CGGCGTCGGC
```

Fig. 12c

```
4801  AACGACCGAG CGCAGCGAGT CAGTGAGCGA GGAAGCGGAA GAGCGCCCAA TACGCAAACC GCCTCTCCCC GCGCGTTGGC
      TTGCTGGCTC GCGTCGCTCA GTCACTCGCT CCTTCGCCTT CTCGCGGGTT ATGCGTTTGG CGGAGAGGGG CGCGCAACCG
4881  CGATTCATTA ATGCAGGTAT CACGAGGCCC TTTCGTCTTC AC
      GCTAAGTAAT TACGTCCATA GTGCTCCGGG AAAGCAGAAG TG
                                       ~~~~~~~~~~
                                          BbsI
```

```
                                                     pIII
1521  CAAGGCACTG ACCCCGTTAA AACTTATTAC CAGTACACTC CTGTATCATC AAAAGCCATG TATGACGCTT ACTGGAACGG
      GTTCCGTGAC TGGGGCAATT TTGAATAATG GTCATGTGAG GACATAGTAG TTTTCGGTAC ATACTGCGAA TGACCTTGCC
                                                     pIII
1601  TAAATTCAGA GACTGCGCTT TCCATTCTGG CTTTAATGAG GATTTATTTG TTTGTGAATA TCAAGGCCAA TCGTCTGACC
      ATTTAAGTCT CTGACGCGAA AGGTAAGACC GAAATTACTC CTAAATAAAC AAACACTTAT AGTTCCGGTT AGCAGACTGG
                                                     pIII
1681  TGCCTCAACC TCCTGTCAAT GCTGGCGGCG GCTCTGGTGG TGGTTCTGGT GGCGGCTCTG AGGGTGGTGG CTCTGAGGGT
      ACGGAGTTGG AGGACAGTTA CGACCGCCGC CGAGACCACC ACCAAGACCA CCGCCGAGAC TCCCACCACC GAGACTCCCA
                                                     pIII
1761  GGCGGTTCTG AGGGTGGCGG CTCTGAGGGA GGCGGTTCCG GTGGTGGCTC TGGTTCCGGT GATTTTGATT ATGAAAAGAT
      CCGCCAAGAC TCCCACCGCC GAGACTCCCT CCGCCAAGGC CACCACCGAG ACCAAGGCCA CTAAAACTAA TACTTTTCTA
                                                     pIII
1841  GGCAAACGCT AATAAGGGGG CTATGACCGA AAATGCCGAT GAAAACGCGC TACAGTCTGA CGCTAAAGGC AAACTTGATT
      CCGTTTGCGA TTATTCCCCC GATACTGGCT TTTACGGCTA CTTTTGCGCG ATGTCAGACT GCGATTTCCG TTTGAACTAA
                                                     pIII
1921  CTGTCGCTAC TGATTACGGT GCTGCTATCG ATGGTTTCAT TGGTGACGTT TCCGGCCTTG CTAATGGTAA TGGTGCTACT
      GACAGCGATG ACTAATGCCA CGACGATAGC TACCAAAGTA ACCACTGCAA AGGCCGGAAC GATTACCATT ACCACGATGA
                                                     pIII
2001  GGTGATTTTG CTGGCTCTAA TTCCCAAATG GCTCAAGTCG GTGACGGTGA TAATTCACCT TTAATGAATA ATTTCCGTCA
      CCACTAAAAC GACCGAGATT AAGGGTTTAC CGAGTTCAGC CACTGCCACT ATTAAGTGGA AATTACTTAT TAAAGGCAGT
                                                     pIII
2081  ATATTTACCT TCCCTCCCTC AATCGGTTGA ATGTCGCCCT TTTGTCTTTG GCGCTGGTAA ACCATATGAA TTTTCTATTG
      TATAAATGGA AGGGAGGGAG TTAGCCAACT TACAGCGGGA AAACAGAAAC CGCGACCATT TGGTATACTT AAAAGATAAC
                                                     pIII
2161  ATTGTGACAA AATAAACTTA TTCCGTGGTG TCTTTGCGTT TCTTTTATAT GTTGCCACCT TTATGTATGT ATTTTCTACG
      TAACACTGTT TTATTTGAAT AAGGCACCAC AGAAACGCAA AGAAAATATA CAACGGTGGA AATACATACA TAAAGATGC
                                           pIII
2241  TTTGCTAACA TACTGCGTAA TAAGGAGTCT TAATGATCTA GAGGCCTGTG CTAATGATCA GCTAGCTTGA GGCATCAATA
      AAACGATTGT ATGACGCATT ATTCCTCAGA ATTACTAGAT CTCCGGACAC GATTACTAGT CGATCGAACT CCGTAGTTAT
2321  AAACGAAAGG CTCAGTCGAA AGACTGGGCC TTTCGTTTTA TCTGTTGTTT GTCGGTTAAC GTCGACCTGG CGTAATAGCG
      TTTGCTTTCC GAGTCAGCTT TCTGACCCGG AAAGCAAAAT AGACAACAAA CAGCCAATTG CAGCTGGACC GCATTATCGC
2401  AAGAGGCCCG CACCGATCGC CCTTCCCAAC AGTTGCGCAG CCTGAATGGC GAATGGGACG CGCCCTGTAG CGGCGCATTA
      TTCTCCGGGC GTGGCTAGCG GGAAGGGTTG TCAACGCGTC GGACTTACCG CTTACCCTGC GCGGGACATC GCCGCGTAAT
2481  AGCGCGGCGG GTGTGGTGGT TACGCGCAGC GTGACCGCTA CACTTGCCAG CGCCCTAGCG CCCGCTCCTT TCGCTTTCTT
      TCGCGCCGCC CACACCACCA ATGCGCGTCG CACTGGCGAT GTGAACGGTC GCGGGATCGC GGGCGAGGAA AGCGAAAGAA
2561  CCCTTCCTTT CTCGCCACGT TCGCCGGCTT TCCCCGTCAA GCTCTAAATC GGGGGCTCCC TTTAGGGTTC CGATTTAGTG
      GGGAAGGAAA GAGCGGTGCA AGCGGCCGAA AGGGGCAGTT CGAGATTTAG CCCCCGAGGG AAATCCCAAG GCTAAATCAC
2641  CTTTACGGCA CCTCGACCCC AAAAAACTTG ATTAGGGTGA TGGTTCACGT AGTGGGCCAT CGCCCTGATA GACGGTTTTT
      GAAATGCCGT GGAGCTGGGG TTTTTTGAAC TAATCCCACT ACCAAGTGCA TCACCCGGTA GCGGGACTAT CTGCCAAAAA
2721  CGCCCTTTGA CGTTGGAGTC CACGTTCTTT AATAGTGGAC TCTTGTTCCA AACTGGAACA ACACTCAACC CTATCTCGGT
      GCGGGAAACT GCAACCTCAG GTGCAAGAAA TTATCACCTG AGAACAAGGT TTGACCTTGT TGTGAGTTGG GATAGAGCCA
2801  CTATTCTTTT GATTTATAAG GGATTTTGCC GATTTCGGCC TATTGGTTAA AAAATGAGCT GATTTAACAA AAATTTAACG
      GATAAGAAAA CTAAATATTC CCTAAAACGG CTAAAGCCGG ATAACCAATT TTTTACTCGA CTAAATTGTT TTTAAATTGC
2881  CGAATTTTAA CAAAATATTA ACGCTTACAA TTTAGGTGGC ACTTTTCGGG GAAATGTGCG CGGAACCCCT ATTTGTTTAT
      GCTTAAAATT GTTTTATAAT TGCGAATGTT AAATCCACCG TGAAAAGCCC CTTTACACGC GCCTTGGGGA TAAACAAATA
2961  TTTTCTAAAT ACATTCAAAT ATGTATCCGC TCATGAGACA ATAACCCTGA TAAATGCTTC AATAATATTG AAAAAGGAAG
      AAAAGATTTA TGTAAGTTTA TACATAGGCG AGTACTCTGT TATTGGGACT ATTTACGAAG TTATTATAAC TTTTTCCTTC
                                           bla
3041  AGTATGAGTA TTCAACATTT CCGTGTCGCC CTTATTCCCT TTTTTGCGGC ATTTTGCCTT CCTGTTTTTG CTCACCCAGA
      TCATACTCAT AAGTTGTAAA GGCACAGCGG GAATAAGGGA AAAAACGCCG TAAAACGGAA GGACAAAAAC GAGTGGGTCT
                                           bla
3121  AACGCTGGTG AAAGTAAAAG ATGCTGAAGA TCAGTTGGGT GCACGAGTGG GTTACATCGA ACTGGATCTC AACAGCGGTA
      TTGCGACCAC TTTCATTTTC TACGACTTCT AGTCAACCCA CGTGCTCACC CAATGTAGCT TGACCTAGAG TTGTCGCCAT
                                           bla
3201  AGATCCTTGA GAGTTTTCGC CCCGAAGAAC GTTTTCCAAT GATGAGCACT TTTAAAGTTC TGCTATGTGG CGCGGTATTA
      TCTAGGAACT CTCAAAAGCG GGGCTTCTTG CAAAAGGTTA CTACTCGTGA AAATTCAAG ACGATACACC GCGCCATAAT
                                           bla
3281  TCCCGTATTG ACGCCGGGCA AGAGCAACTC GGTCGCCGCA TACACTATTC TCAGAATGAC TTGGTTGAGT ACTCACCAGT
      AGGGCATAAC TGCGGCCCGT TCTCGTTGAG CCAGCGGCGT ATGTGATAAG AGTCTTACTG AACCAACTCA TGAGTGGTCA
                                           bla
3361  CACAGAAAAG CATCTTACGG ATGGCATGAC AGTAAGAGAA TTATGCAGTG CTGCCATAAC CATGAGTGAT AACACTGCGG
      GTGTCTTTTC GTAGAATGCC TACCGTACTG TCATTCTCTT AATACGTCAC GACGGTATTG GTACTCACTA TTGTGACGCC
                                           bla
3441  CCAACTTACT TCTGACAACG ATCGGAGGAC CGAAGGAGCT AACCGCTTTT TTGCACAACA TGGGGGATCA TGTAACTCGC
      GGTTGAATGA AGACTGTTGC TAGCCTCCTG GCTTCCTCGA TTGGCGAAAA AACGTGTTGT ACCCCCTAGT ACATTGAGCG
```

```
                                                          CAP-binding site                           -35 (lac)
  1   CTCGAGAGCG GGCAGTGAGC GCAACGCAAT TAATGTGAGT TAGCTCACTC ATTAGGCACC CCAGGCTTTA CACTTTATGC
      GAGCTCTCGC CCGTCACTCG CGTTGCGTTA ATTACACTCA ATCGAGTGAG TAATCCGTGG GGTCCGAAAT GTGAAATACG
                 -10 (lac)            lac-operator                                                   pelB-lead
 81   TTCCGGCTCG TATGTTGTGT GGAATTGTGA GCGGATAACA ATTTCACACA GAATTCATTA AAGAGGAGAA ATTAACCATG
      AAGGCCGAGC ATACAACACA CCTTAACACT CGCCTATTGT TAAAGTGTGT CTTAAGTAAT TTCTCCTCTT TAATTGGTAC
                                       pelB-leader
                                                                            NcoI
161   AAATACCTAT TGCCTACGGC AGCCGCTGGC TTGCTGCTGC TGGCAGCTCA GCCGGCCATG GCGCAGGTAC AGCTGCAGGA
      TTTATGGATA ACGGATGCCG TCGGCGACCG AACGACGACG ACCGTCGAGT CGGCCGGTAC CGCGTCCATG TCGACGTCCT
                                                                                          HCDR1
241   GTCTGGGGGA GGCGTGGTCC AGCCTGGGAG GTCCCTGAGA CTCTCCTGTG CAGCCTCTGG ATTCTCCTTC AGTAATTATG
      CAGACCCCCT CCGCACCAGG TCGGACCCTC CAGGGACTCT GAGAGGACAC GTCGGAGACC TAAGAGGAAG TCATTAATAC
          HCDR1                                                                HCDR2
321   GCATACACTG GGTCCGCCAG GCTCCAGGCA AGGGGCTGGA GTGGGTGGCA CTTATATCAT ATGATGGAAA TAAGAAATTC
      CGTATGTGAC CCAGGCGGTC CGAGGTCCGT TCCCCGACCT CACCCACCGT GAATATAGTA TACTACCTTT ATTCTTTAAG
           HCDR2
401   TATGCAGACT CCGTGAAGGG CCGATTCGCC ATCTCCAGAG ACACTTCTAA GAATACGGTG GATCTGCAAA TGACCAGCCT
      ATACGTCTGA GGCACTTCCC GGCTAAGCGG TAGAGGTCTC TGTGAAGATT CTTATGCCAC CTAGACGTTT ACTGGTCGGA
                                        stuffer
                                              BbsI                                              HindIII
481   GAGACCTGAG GACACGTCTT CAGCGCTGAG CTCGAAGACT GGTCACCGTC TCCTCAGCCT CCACCAAGGG CCCAAAGCTT
      CTCTGGACTC CTGTGCAGAA GTCGCGACTC GAGCTTCTGA CCAGTGGCAG AGGAGTCGGA GGTGGTTCCC GGGTTTCGAA
                                                                  BbsI
                                                                                  C9-light chain (lambda)
           YOL-linker
                                 MluI
561   GAAGAAGGTG AATTTTCAGA AGCACGCGTA TCCTATGAAC TGACTCAGCC ACCCTCGGTG TCAGTGGCCC CAGGACAGAC
      CTTCTTCCAC TTAAAAGTCT TCGTGCGCAT AGGATACTTG ACTGAGTCGG TGGGAGCCAC AGTCACCGGG GTCCTGTCTG
                                                     LCDR1
                                           C9-light chain (lambda)
641   GGCCATGATT ACCTGTGGGG AAACAACAT TGGAAGTACA ACCGTGCACT GGTATCAGCA GAAGCCAGGC CAGGCCCCTG
      CCGGTACTAA TGGACACCCC TTTGTTGTA ACCTTCATGT TGGCACGTGA CCATAGTCGT CTTCGGTCCG GTCCGGGGAC
                                                     LCDR2
                                           C9-light chain (lambda)
721   TGCTGGTCGT CTATGATGAT AACGAGCGAC CCTCAGGGAT CCCTGAGCGA TTCTCTGGCT CCAACTCTGG GAGCACGGCC
      ACGACCAGCA GATACTACTA TTGCTCGCTG GGAGTCCCTA GGGACTCGCT AAGAGACCGA GGTTGAGACC CTCGTGCCGG
                                                                                    LCDR3
                                              C9-light chain (lambda)
801   ACCCTGACCA TCAACAGGGT CGAAGCCGGG GATGAGGCCG ACTATTATTG TCAAGTGTGG GATAGTGGTA GTGATCATGT
      TGGGACTGGT AGTTGTCCCA GCTTCGGCCC CTACTCCGGC TGATAATAAC AGTTCACACC CTATCACCAT CACTAGTACA
        LCDR3
                                         C9-light chain (lambda)
881   GGTATTCGGC GGAGGGACCG AGCTGACCGT CCTAGGTCAG CCCAAGGCTG CCCCCTCGGT CACTCTGTTC CCGCCCTCCT
      CCATAAGCCG CCTCCCTGCT TCGACTGGCA GGATCCAGTC GGGTTCCGAC GGGGAGCCA GTGAGACAAG GCGGGAGGA
           NotI                                 amber-st
        C9-light chain (lam              6xHis                                c-myc
961   CTGCGGCCGC TGGATCCCAT CACCATCACC ATCACTAGGA ACAAAAGCTG ATCTCAGAAG AGGACCTAAA CGGATCCAAA
      GACGCCGGCG ACCTAGGGTA GTGGTAGTGG TAGTGATCCT TGTTTTCGAC TAGAGTCTTC TCCTGGATTT GCCTAGGTTT
                                                                   pIII
1041  GATATCAGAG CTGAAACTGT TGAAAGTTGT TTAGCAAAAT CCCATACAGA AAATTCATTT ACTAACGTCT GGAAAGACGA
      CTATAGTCTC GACTTTGACA ACTTTCAACA AATCGTTTTA GGGTATGTCT TTTAAGTAAA TGATTGCAGA CCTTTCTGCT
                                                                   pIII
1121  CAAAACTTTA GATCGGTTACG CTAACTATGA GGGCTGTCTG TGGAATGCTA CAGGCGTTGT AGTTTGTACT GGTGACGAAA
      GTTTTGAAAT CTAGCAATGC GATTGATACT CCCGACAGAC ACCTTACGAT GTCCGCAACA TCAAACATGA CCACTGCTTT
                                                                   pIII
1201  CTCAGTGTTA CGGTACATGG TTCCTATTG GGCTTGCTAT CCCTGAAAAT GAGGGTGGTG GCTCTGAGGG TGGCGGTTCT
      GAGTCACAAT GCCATGTACC AAGGATAAC CCGAACGATA GGGACTTTTA CTCCCACCAC CGAGACTCCC ACCGCCAAGA
                                                                   pIII
1281  GAGGGTGGCG GTTCTGAGGG TGGCGGTACT AAACCTCCTG AGTACGGTGA TACACCCTATT CCGGGCTATA CTTATATCAA
      CTCCCACCGC CAAGACTCCC ACCGCCATGA TTTGGAGGAC TCATGCCACT ATGTGGATAA GGCCCGATAT GAATATAGTT
                                                                   pIII
1361  CCCTCTCGAC GGCACTTATC CGCCTGGTAC TGAGCAAAAC CCCGCTAATC CTAATCCTTC TCTTGAGGAG TCTCAGCCTC
      GGGAGAGCTG CCGTGAATAG GCGGACCATG ACTCGTTTTG GGGCGATTAG GATTAGGAAG AGAACTCCTC AGAGTCGGAG
                                                                   pIII
1441  TTAATACTTT CATGTTTCAG AATAATAGGT TCCGAAATAG GCAGGGGGCA TTAACTGTTT ATACGGGCAC TGTTACTCAA
      AATTATGAAA GTACAAAGTC TTATTATCCA AGGCTTTATC CGTCCCCGT AATTGACAAA TATGCCCGTG ACAATGAGTT
```

Fig. 14a

|  | pIII |
|---|---|
| 1521 | GGCACTGACC CCGTTAAAAC TTATTACCAG TACACTCCTG TATCATCAAA AGCCATGTAT GACGCTTACT GGAACGGTAA |
|  | CCGTGACTGG GGCAATTTTG AATAATGGTC ATGTGAGGAC ATAGTAGTTT TCGGTACATA CTGCGAATGA CCTTGCCATT |

|  | pIII |
|---|---|
| 1601 | ATTCAGAGAC TGCGCTTTCC ATTCTGGCTT TAATGAGGAT TTATTTGTTT GTGAATATCA AGGCCAATCG TCTGACCTGC |
|  | TAAGTCTCTG ACGCGAAAGG TAAGACCGAA ATTACTCCTA AATAAACAAA CACTTATAGT TCCGGTTAGC AGACTGGACG |

|  | pIII |
|---|---|
| 1681 | CTCAACCTCC TGTCAATGCT GGCGGCGGCT CTGGTGGTGG TTCTGGTGGC GGCTCTGAGG GTGGTGGCTC TGAGGGTGGC |
|  | GAGTTGGAGG ACAGTTACGA CCGCCGCCGA GACCACCACC AAGACCACCG CCGAGACTCC CACCACCGAG ACTCCCACCG |

|  | pIII |
|---|---|
| 1761 | GGTTCTGAGG GTGGCGGCTC TGAGGGAGGC GGTTCCGGTG GTGGCTCTGG TTCCGGTGAT TTTGATTATG AAAAGATGGC |
|  | CCAAGACTCC CACCGCCGAG ACTCCCTCCG CCAAGGCCAC CACCGAGACC AAGGCCACTA AAACTAATAC TTTTCTACCG |

|  | pIII |
|---|---|
| 1841 | AAACGCTAAT AAGGGGGCTA TGACCGAAAA TGCCGATGAA AACGCGCTAC AGTCTGACGC TAAAGGCAAA CTTGATTCTG |
|  | TTTGCGATTA TTCCCCCGAT ACTGGCTTTT ACGGCTACTT TTGCGCGATG TCAGACTGCG ATTTCCGTTT GAACTAAGAC |

|  | pIII |
|---|---|
| 1921 | TCGCTACTGA TTACGGTGCT GCTATCGATG GTTTCATTGG TGACGTTTCC GGCCTTGCTA ATGGTAATGG TGCTACTGGT |
|  | AGCGATGACT AATGCCACGA CGATAGCTAC CAAAGTAACC ACTGCAAAGG CCGGAACGAT TACCATTACC ACGATGACCA |

|  | pIII |
|---|---|
| 2001 | GATTTTGCTG GCTCTAATTC CCAAATGGCT CAAGTCGGTG ACGGTGATAA TTCACCTTTA ATGAATAATT TCCGTCAATA |
|  | CTAAAACGAC CGAGATTAAG GGTTTACCGA GTTCAGCCAC TGCCACTATT AAGTGGAAAT TACTTATTAA AGGCAGTTAT |

|  | pIII |
|---|---|
| 2081 | TTTACCTTCC CTCCCTCAAT CGGTTGAATG TCGCCCTTTT GTCTTTGGCG CTGGTAAACC ATATGAATTT TCTATTGATT |
|  | AAATGGAAGG GAGGGAGTTA GCCAACTTAC AGCGGGAAAA CAGAAACCGC GACCATTTGG TATACTTAAA AGATAACTAA |

|  | pIII |
|---|---|
| 2161 | GTGACAAAAT AAACTTATTC CGTGGTGTCT TTGCGTTTCT TTTATATGTT GCCACCTTTA TGTATGTATT TTCTACGTTT |
|  | CACTGTTTTA TTTGAATAAG GCACCACAGA AACGCAAAGA AAATATACAA CGGTGGAAAT ACATACATAA AAGATGCAAA |

|  | pIII |
|---|---|
| 2241 | GCTAACATAC TGCGTAATAA GGAGTCTTAA TGATCTAGAG GCCTGTGCTA ATGATCAGCT AGCTTGAGGC ATCAATAAAA |
|  | CGATTGTATG ACGCATTATT CCTCAGAATT ACTAGATCTC CGGACACGAT TACTAGTCGA TCGAACTCCG TAGTTATTTT |

| 2321 | CGAAAGGCTC AGTCGAAAGA CTGGGCCTTT CGTTTTATCT GTTGTTTGTC GGTAACGTC GACCTGGCGT AATAGCGAAG |
|---|---|
|  | GCTTTCCGAG TCAGCTTTCT GACCCGGAAA GCAAATAGA CAACAAACAG CCAATTGCAG CTGGACCGCA TTATCGCTTC |

| 2401 | AGGCCCGCAC CGATCGCCCT TCCCAACAGT TGCGCAGCCT GAATGGCGAA TGGGACGCGC CCTGTAGCGG CGCATTAAGC |
|---|---|
|  | TCCGGGCGTG GCTAGCGGGA AGGGTTGTCA ACGCGTCGGA CTTACCGCTT ACCCTGCGCG GGACATCGCC GCGTAATTCG |

| 2481 | GCGGCGGGTG TGGTGGTTAC GCGCAGCGTG ACCGCTACAC TTGCCAGCGC CCTAGCGCCC GCTCCTTTCG CTTTCTTCCC |
|---|---|
|  | CGCCGCCCAC ACCACCAATG CGCGTCGCAC TGGCGATGTG AACGGTCGCG GGATCGCGGG CGAGGAAAGC GAAAGAAGGG |

| 2561 | TTCCTTTCTC GCCACGTTCG CCGGCTTTCC CCGTCAAGCT CTAAATCGGG GGCTCCCTTT AGGGTTCCGA TTTAGTGCTT |
|---|---|
|  | AAGGAAAGAG CGGTGCAAGC GGCCGAAAGG GGCAGTTCGA GATTTAGCCC CCGAGGGAAA TCCCAAGGCT AAATCACGAA |

| 2641 | TACGGCACCT CGACCCCAAA AAACTTGATT AGGGTGATGG TTCACGTAGT GGGCCATCGC CCTGATAGAC GGTTTTTCGC |
|---|---|
|  | ATGCCGTGGA GCTGGGGTTT TTTGAACTAA TCCCACTACC AAGTGCATCA CCCGGTAGCG GGACTATCTG CCAAAAAGCG |

| 2721 | CCTTTGACGT TGGAGTCCAC GTTCTTTAAT AGTGGACTCT TGTTCCAAAC TGGAACAACA CTCAACCCTA TCTCGGTCTA |
|---|---|
|  | GGAAACTGCA ACCTCAGGTG CAAGAAATTA TCACCTGAGA ACAAGGTTTG ACCTTGTTGT GAGTTGGGAT AGAGCCAGAT |

| 2801 | TTCTTTTGAT TTATAAGGGA TTTTGCCGAT TTCGGCCTAT TGGTTAAAAA ATGAGCTGAT TTAACAAAAA TTTAACGCGA |
|---|---|
|  | AAGAAAACTA AATATTCCCT AAAACGGCTA AAGCCGGATA ACCAATTTTT TACTCGACTA AATTGTTTTT AAATTGCGCT |

| 2881 | ATTTTAACAA AATATTAACG CTTACAATTT AGGTGGCACT TTTCGGGGAA ATGTGCGCGG AACCCCTATT TGTTTATTTT |
|---|---|
|  | TAAAATTGTT TTATAATTGC GAATGTTAAA TCCACCGTGA AAAGCCCCTT TACACGCGCC TTGGGGATAA ACAAATAAAA |

| 2961 | TCTAAATACA TTCAAATATG TATCCGCTCA TGAGACAATA ACCCTGATAA ATGCTTCAAT AATATTGAAA AAGGAAGAGT |
|---|---|
|  | AGATTTATGT AAGTTTATAC ATAGGCGAGT ACTCTGTTAT TGGGACTATT TACGAAGTTA TTATAACTTT TTCCTTCTCA |

|  | bla |
|---|---|
| 3041 | ATGAGTATTC AACATTTCCG TGTCGCCCTT ATTCCCTTTT TTGCGGCATT TTGCCTTCCT GTTTTTGCTC ACCCAGAAAC |
|  | TACTCATAAG TTGTAAAGGC ACAGCGGGAA TAAGGGAAAA AACGCCGTAA AACGGAAGGA CAAAAACGAG TGGGTCTTTG |

|  | bla |
|---|---|
| 3121 | GCTGGTGAAA GTAAAAGATG CTGAAGATCA GTTGGGTGCA CGAGTGGGTT ACATCGAACT GGATCTCAAC AGCGGTAAGA |
|  | CGACCACTTT CATTTTCTAC GACTTCTAGT CAACCCACGT GCTCACCCAA TGTAGCTTGA CCTAGAGTTG TCGCCATTCT |

|  | bla |
|---|---|
| 3201 | TCCTTGAGAG TTTTCGCCCC GAAGAACGTT TTCCAATGAT GAGCACTTTT AAAGTTCTGC TATGTGGCGC GGTATTATCC |
|  | AGGAACTCTC AAAAGCGGGG CTTCTTGCAA AAGGTTACTA CTCGTGAAAA TTTCAAGACG ATACACCGCG CCATAATAGG |

|  | bla |
|---|---|
| 3281 | CGTATTGACG CCGGGCAAGA GCAACTCGGT CGCCGCATAC ACTATTCTCA GAATGACTTG GTTGAGTACT CACCAGTCAC |
|  | GCATAACTGC GGCCCGTTCT CGTTGAGCCA GCGGCGTATG TGATAAGAGT CTTACTGAAC CAACTCATGA GTGGTCAGTG |

|  | bla |
|---|---|
| 3361 | AGAAAAGCAT CTTACGGATG GCATGACAGT AAGAGAATTA TGCAGTGCTG CCATAACCAT GAGTGATAAC ACTGCGGCCA |
|  | TCTTTTCGTA GAATGCCTAC CGTACTGTCA TTCTCTTAAT ACGTCACGAC GGTATTGGTA CTCACTATTG TGACGCCGGT |

|  | bla |
|---|---|
| 3441 | ACTTACTTCT GACAACGATC GGAGGACCGA AGGAGCTAAC CGCTTTTTTG CACAACATGG GGGATCATGT AACTCGCCTT |
|  | TGAATGAAGA CTGTTGCTAG CCTCCTGGCT TCCTCGATTG GCGAAAAAAC GTGTTGTACC CCCTAGTACA TTGAGCGGAA |

Fig. 14bv

```
                                    bla
3521  GATCGTTGGG AACCGGAGCT GAATGAAGCC ATACCAAACG ACGAGCGTGA CACCACGATG CCTGTAGCAA TGGCAACAAC
      CTAGCAACCC TTGGCCTCGA CTTACTTCGG TATGGTTTGC TGCTCGCACT GTGGTGCTAC GGACATCGTT ACCGTTGTTG
                                    bla
3601  GTTGCGCAAA CTATTAACTG GCGAACTACT TACTCTAGCT TCCCGGCAAC AATTAATAGA CTGGATGGAG GCGGATAAAG
      CAACGCGTTT GATAATTGAC CGCTTGATGA ATGAGATCGA AGGGCCGTTG TTAATTATCT GACCTACCTC CGCCTATTTC
                                    bla
3681  TTGCAGGACC ACTTCTGCGC TCGGCCCTTC CGGCTGGCTG GTTTATTGCT GATAAATCTG GAGCCGGTGA GCGTGGGTCT
      AACGTCCTGG TGAAGACGCG AGCCGGGAAG GCCGACCGAC CAAATAACGA CTATTTAGAC CTCGGCCACT CGCACCCAGA
                                    bla
3761  CGCGGTATCA TTGCAGCACT GGGGCCAGAT GGTAAGCCCT CCCGTATCGT AGTTATCTAC ACGACGGGGA GTCAGGCAAC
      GCGCCATAGT AACGTCGTGA CCCCGGTCTA CCATTCGGGA GGGCATAGCA TCAATAGATG TGCTGCCCCT CAGTCCGTTG
                                    bla
3841  TATGGATGAA CGAAATAGAC AGATCGCTGA GATAGGTGCC TCACTGATTA AGCATTGGTA ACTGTCAGAC CAAGTTTACT
      ATACCTACTT GCTTTATCTG TCTAGCGACT CTATCCACGG AGTGACTAAT TCGTAACCAT TGACAGTCTG GTTCAAATGA
3921  CATATATACT TTAGATTGAT TTAAAACTTC ATTTTTAATT TAAAAGGATC TAGGTGAAGA TCCTTTTTGA TAATCTCATG
      GTATATATGA AATCTAACTA AATTTTGAAG TAAAAATTAA ATTTTCCTAG ATCCACTTCT AGGAAAAACT ATTAGAGTAC
4001  ACCAAAATCC GTTAACGTGA GTTTTCGTTC CACTGAGCGT CAGACCCCGT AGAAAAGATC AAAGGATCTT CTTGAGATCC
      TGGTTTTAGG GAATTGCACT CAAAAGCAAG GTGACTCGCA GTCTGGGGCA TCTTTTCTAG TTTCCTAGAA GAACTCTAGG
4081  TTTTTTTCTG CGCGTAATCT GCTGCTTGCA AACAAAAAAA CCACCGCTAC CAGCGGTGGT TTGTTTGCCG GATCAAGAGC
      AAAAAAAGAC GCGCATTAGA CGACGAACGT TTGTTTTTTT GGTGGCGATG GTCGCCACCA AACAAACGGC CTAGTTCTCG
4161  TACCAACTCT TTTTCCGAAG GTAACTGGCT TCAGCAGAGC GCAGATACCA AATACTGTCC TTCTAGTGTA GCCGTAGTTA
      ATGGTTGAGA AAAAGGCTTC CATTGACCGA AGTCGTCTCG CGTCTATGGT TTATGACAGG AAGATCACAT CGGCATCAAT
4241  GGCCACCACT TCAAGAACTC TGTAGCACCG CCTACATACC TCGCTCTGCT AATCCTGTTA CCAGTGGCTG CTGCCAGTGG
      CCGGTGGTGA AGTTCTTGAG ACATCGTGGC GGATGTATGG AGCGAGACGA TTAGGACAAT GGTCACCGAC GACGGTCACC
4321  CGATAAGTCG TGTCTTACCG GGTTGGACTC AAGACGATAG TTACCGGATA AGGCGCAGCG GTCGGGCTGA ACGGGGGGTT
      GCTATTCAGC ACAGAATGGC CCAACCTGAG TTCTGCTATC AATGGCCTAT TCCGCGTCGC CAGCCCGACT TGCCCCCCAA
4401  CGTGCACACA GCCCAGCTTG GAGCGAACGA CCTACACCGA ACTGAGATAC CTACAGCGTG AGCTATGAGA AAGCGCCACG
      GCACGTGTGT CGGGTCGAAC CTCGCTTGCT GGATGTGGCT TGACTCTATG GATGTCGCAC TCGATACTCT TTCGCGGTGC
4481  CTTCCCGAAG GGAGAAAGGC GGACAGGTAT CCGGTAAGCG GCAGGGTCGG AACAGGAGAG CGCACGAGGG AGCTTCCAGG
      GAAGGGCTTC CCTCTTTCCG CCTGTCCATA GGCCATTCGC CGTCCCAGCC TTGTCCTCTC GCGTGCTCCC TCGAAGGTCC
4561  GGGAAACGCC TGGTATCTTT ATAGTCCTGT CGGGTTTCGC CACCTCTGAC TTGAGCGTCG ATTTTTGTGA TGCTCGTCAG
      CCCTTTGCGG ACCATAGAAA TATCAGGACA GCCCAAAGCG GTGGAGACTG AACTCGCAGC TAAAAACACT ACGAGCAGTC
4641  GGGGCGGAG CCTATGGAAA AACGCCAGCA ACGCGGCCTT TTTACGGTTC CTGGCCTTTT GCTGGCCTTT TGCTCACATG
      CCCCCGCCTC GGATACCTTT TTGCGGTCGT TGCGCCGGAA AAATGCCAAG GACCGGAAAA CGACCGGAAA ACGAGTGTAC
4721  TTCTTTCCTG CGTTATCCCC TGATTCTGTG GATAACCGTA TTACCGCCTT TGAGTGAGCT GATACCGCTC GCCGCAGCCG
      AAGAAAGGAC GCAATAGGGG ACTAAGACAC CTATTGGCAT AATGGCGGAA ACTCACTCGA CTATGGCGAG CGGCGTCGGC
4801  AACGACCGAG CGCAGCGAGT CAGTGAGCGA GGAAGCGGAA GAGCGCCCAA TACGCAAACC GCCTCTCCCC GCGCGTTGGC
      TTGCTGGCTC GCGTCGCTCA GTCACTCGCT CCTTCGCCTT CTCGCGGGTT ATGCGTTTGG CGGAGAGGGG CGCGCAACCG
4881  CGATTCATTA ATGCAGGTAT CACGAGGCCC TTTCGTCCTC AC
      GCTAAGTAAT TACGTCCATA GTGCTCCGGG AAAGCAGGAG TG
```

| vector construction | library construction |
|---|---|
| VH/for/cut (#29):<br>AAT GCA GGT ATC ACG AGG C<u>CC TTT</u> CGT CTT C<br>C9/VLCDR3/back/cut (#53)<br>TACTACGAAGACGC<u>CTCA</u>TCCCCGGCTTCGACCC<br>E4/VLCDR3/back/cut (#54)<br>TACTACGAAGACTGA<u>CCG</u>TCCTACGTCAGCCCAAGGC<br><br>CL/for/cut (#55)<br>TACTACGAAGACTGA<u>CCG</u>TCCTASGTCAGCCCAAGGC<br>VL/back/cut (#24):<br>CAG CTC TGA TAT CTT TGG ATC C<u>GT TTA</u> GGT CTT CTT CTG<br><br>VLCDR3/stuff/for/P (#58)<br>P-<u>TGAG</u>GCGTCTTCAGCGCTGAGCTCGAAGACTG<br>VLCDR3/stuff/back/P (#59)<br>P-<u>CGGT</u>CAGTCTTCGAGCTCAGCGCTGAAGACGC3'<br><br>LAM1 (#40)<br>AGCCTG<u>GAGCTCT</u>AAAAAGCGTGCTGCTGAACAGTA<br>LAM2 (#41)<br>CGACTG<u>GAGCT</u>CGAACACGGCTCACTTTTACCTTCA | C9VLCDR3_4/cut:<br>A<u>TGAG</u>GCCGACTATTATTGTCAAGTGTGG(NNK)<sub>4</sub>GTGGTATTCGGCGGA<br>GGGACGAAGCTGA<u>CCG</u>T<br>C9VLCDR3_5/cut:<br>A<u>TGAG</u>GCCGACTATTATTGTCAAGTGTGG(NNK)<sub>5</sub>GTGGTATTCGGCGGA<br>GGGACGAAGCTGA<u>CCG</u>T<br>C9VLCDR3_6/cut:<br>A<u>TGAG</u>GCCGACTATTATTGTCAAGTGTGG(NNK)<sub>6</sub>GTGGTATTCGGCGGA<br>GGGACGAAGCTGA<u>CCG</u>T<br>C9VLCDR3_for/cut:<br>TACTAC*GAAGA*CGA<u>TGAG</u>GCCGACTATTATTGTCAAGTG<br>C9VLCDR3_back/cut:<br>TACTAC*GAAGA*CGA<u>CGGT</u>CAGCTTCGTCCCTCCGCCGAA<br><br>E4VLCDR3_4/cut:<br>A<u>TGAG</u>GCTGACTATTACTGTAACTCCCGG(NNK)<sub>4</sub>GTGCTATTCGGCGGA<br>GGGACCAAGCTGA<u>CCG</u>T<br>E4VLCDR3_5/cut:<br>A<u>TGAG</u>GCTGACTATTACTGTAACTCCCGG(NNK)<sub>5</sub>GTGCTATTCGGCGGA<br>GGGACCAAGCTGA<u>CCG</u>T<br>E4VLCDR3_6/cut:<br>A<u>TGAG</u>GCTGACTATTACTGTAACTCCCGG(NNK)<sub>6</sub>GTGCTATTCGGCGGA<br>GGGACCAAGCTGA<u>CCG</u>T<br><br>E4VLCDR3_for/cut:<br>TACTAC*GAAGA*CGA<u>TGAG</u>GCTGACTATTACTGTAACTCC<br>E4VLCDR3_back/cut:<br>TACTAC*GAAGA*CGA<u>CGGT</u>CAGCTTGGTCCCTCCGCCGAA<br><br>VLCDR3_ev/for/cut:<br>TACTAC*GAAGA*CGA<u>TGAG</u>GCTGAYTATTACTG<br>VLCDR3_ev/back/cut:<br>TACTAC*GAAGA*CGA<u>CGGT</u>CAGCTTGGTCCCTCC |

Fig. 19
MB9 scFv (scFv21)
...V T V S *S G S A S A P T L K L E E G E F S E A R V* Q A V L...
MB9 diabody (scFv3)
...V T V S *S R V* Q A V L...
Fig. 20
pREFAB9
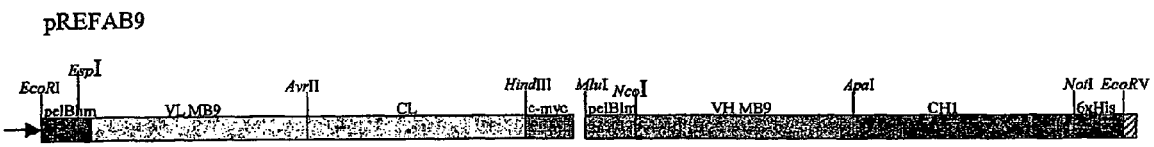
Fig. 21
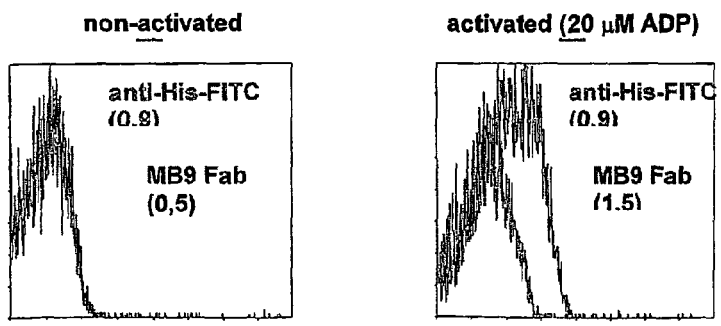

Fig. 22

```
ctcgagagcg ggcagtgagc gcaacgcaat taatgtgagt tagctcactc attaggcacc    60
ccaggcttta cactttatgc tcccggctcg tatgttgtgt ggaattgtga gcggataaca   120
atttcacaca gaattcatta aagaggagaa attaaccatg aagtacctct taccaaccgc   180
agcggctggt ttactgctcc tggcggctca gccggcaatg gcacaggctg tgctgactca   240
gccgccctcg gtgtcagtgg ccccaggaca gacggccagg attacctgtg ggggaaacaa   300
cattggaagt aaaagtgtgc agtggtacca gcagaagcca ggccaggccc ctgtgctggt   360
cgtctatgat gatagcgacc ggccctcagg gatccctgag cgattctctg gctccaactc   420
tgggaacatg gccaccctga ccatcagcag ggtcgaagcc ggggatgagg ccgactatta   480
ctgtcaggtg tgggatagta gtagtgatca tgtggtattc ggcggaggga ccaagctgac   540
cgtcctaggt cagcccaagg ctgccccctc ggtcactctg ttcccgccct cctctgagga   600
gcttcaagcc aacaaggcca cactggtgtg tctcataagt gacttctacc cgggagccgt   660
gacagtggcc tggaaggcag atagcagccc cgtcaaggcg ggagtggaga ccaccacacc   720
ctccaaacaa agcaacaaca agtacgcggc cagcagctat ctgagcctga cgcctgagca   780
gtggaagtcc cacagaagct acagctgcca ggtcacgcat gaagggagca ccgtggagaa   840
gacagtggcc cctacagaat gttcagaaca aaagcttatc tcagaagagg acctaaacta   900
atgaacgcgt tattaaagag gagaaattaa ccatgaaata cctattgcct acggcagccg   960
ctggcttgct gctgctggca gcacaaccgg ccatggcgga agtgcagctg gtgcagtctg  1020
gagctgaggt gaataagcct ggggcctcag tgaaggtctc ctgcaaggct tctggataca  1080
ccttcaccgg ctactatatg cactgggtgc gacaggcccc tggacaaggg cttgagtgga  1140
tgggatggat caaccctaac agtggtggca caaactatgc acagaagttt cagggctggg  1200
tcaccatgac cagggacacg tccatcagca ccgcctacat ggagctgagc aggctgagat  1260
ctgacgacac ggccgtgtat tactgtgcga gaggccgtgc tttgtataac cggaacgacc  1320
ggtcccccaa ctggttcgac ccctggggcc agggaaccct ggtcaccgtc tcctcagcct  1380
ccaccaaggg cccatcggtc ttccccctgg cacctcctc caagagcacc tctgggggca  1440
cagcggccct gggctgcctg gtcaaggact acttccccga accggtgacg gtgtcgtgga  1500
actcaggcgc cctgaccagc ggcgtgcaca ccttccggc tgtcctacag tcctcaggac  1560
tctactccct cagcagcgtg gtgaccgtgc cctccagcag cttgggcacc cagacctaca  1620
tctgcaacgt gaatcacaag cccagcaaca ccaaggtgga caagaaagtt gagcccaaat  1680
cttgtgcggc cgctggatcc catcaccatc accatcacta gggatccaaa gatatcagag  1740
ctgaaactgt tgaaagttgt ttagcaaaat cccatacaga aaattcattt actaacgtct  1800
ggaaagacga caaaacttta gatcgttacg ctaactatga gggctgtctg tggaatgcta  1860
caggcgttgt agtttgtact ggtgacgaaa ctcagtgtta cggtacatgg gttcctattg  1920
ggcttgctat ccctgaaaat gaggggtggtg gctctgaggg tggcggttct gagggtggcg  1980
gttctgaggg tggcggtact aaacctcctg agtacggtga tacaccntatt ccgggctata  2040
cttatatcaa ccctctcgac ggcacttatc cgcctggtac tgagcaaaac cccgctaatc  2100
ctaatccttc tcttgaggag tctcagcctc ttaatacttt catgtttcag aataataggt  2160
tccgaaatag gcaggggca ttaactgttt atacgggcac tgttactcaa ggcactgacc  2220
ccgttaaaac ttattaccag tacactcctg tatcatcaaa agccatgtat gacgcttact  2280
ggaacggtaa attcagagac tgcgctttcc attctggctt taatgaggat ttatttgttt  2340
gtgaatatca aggccaatcg tctgacctgc ctcaacctcc tgtcaatgct ggcggcggct  2400
ctggtggtgg ttctggtggc ggctctgagg gtggtggctc tgagggtggc ggttctgagg  2460
gtggcggctc tgagggaggc ggttccggtg tggctctgg ttccggtgat tttgattatg  2520
aaaagatggc aaacgctaat aaggggggcta tgaccgaaaa tgccgatgaa aacgcgctac  2580
agtctgacgc taaaggcaaa cttgattctg tcgctactga ttacggtgct gctatcgatg  2640
gtttcattgg tgacgtttcc ggccttgcta atggtaatgg tgctactggt gattttgctg  2700
gctctaattc ccaaatggct caagtcggtg acggtgataa ttcacctttta atgaataatt  2760
tccgtcaata tttaccttcc ctccctcaat cggttgaatg tcgcccttt gtctttggcg  2820
ctggtaaacc atatgaattt tctattgatt gtgacaaaat aaacttattc cgtggtgtct  2880
ttgcgtttct tttatatgtt gccaccttta tgtatgtatt ttctacgttt gctaacatac  2940
tgcgtaataa ggagtcttaa tgatctagag gcctgtgcta atgatcagct agcttgaggc  3000
atcaataaaa cgaaaggctc agtcgaaaga ctgggccttt catttatct gttgtttgtc  3060
ggttaacgtc gacctggcgt aatagcgaag aggcccgcac cgatcgccct tcccaacagt  3120
tgcgcagcct gaatggcgaa tgggacgcgc cctgtagcgg cgcattaagc gcggcgggtg  3180
tggtggttac gcgcagcgtg accgctacac ttgccagcgc cctagcgccc gctcctttcg  3240
ctttcttccc ttcctttctc gccacgttcg ccggctttcc ccgtcaagct ctaaatcggg  3300
ggctccctt agggttccga tttagtgctt tacggcacct cgaccccaaa aaacttgatt  3360
agggtgatgg ttcacgtagt gggccatcgc cctgatagac ggtttttcgc cctttgacgt  3420
tggagtccac gttctttaat agtggactct tgttccaaac tggaacaaca ctcaaccta   3480
tctcggtcta ttcttttgat ttataaggga ttttgccgat ttcggcctat tggttaaaaa  3540
atgagctgat ttaacaaaaa tttaacgcga attttaacaa atattaacg cttacaattt  3600
aggtggcact tttcggggaa atgtgcgcgg aacccctatt tgtttatttt tctaaataca  3660
ttcaaatatg tatccgctca tgagacaata accctgataa atgcttcaat aatattgaaa  3720
aaggaagagt atgagtattc aacatttccg tgtcgccctt attcccttt ttgcggcatt  3780
ttgccttcct gtttttgctc acccagaaac gctggtgaaa gtaaaagatg ctgaagatca  3840
```

Fig. 22 (Continuation)

```
gttgggtgca cgagtgggtt acatcgaact ggatctcaac agcggtaaga tccttgagag    3900
ttttcgcccc gaagaacgtt ttccaatgat gagcactttt aaagttctgc tatgtggcgc    3960
ggtattatcc cgtattgacg ccgggcaaga gcaactcggt cgccgcatac actattctca    4020
gaatgacttg gttgagtact caccagtcac agaaaagcat cttacggatg gcatgacagt    4080
aagagaatta tgcagtgctg ccataaccat gagtgataac actgcggcca acttacttct    4140
gacaacgatc ggaggaccga aggagctaac cgctttttg cacaacatgg gggatcatgt     4200
aactcgcctt gatcgttggg aaccggagct gaatgaagcc ataccaaacg acgagcgtga    4260
caccacgatg cctgtagcaa tggcaacaac gttgcgcaaa ctattaactg gcgaactact    4320
tactctagct tcccggcaac aattaataga ctggatggag gcggataaag ttgcaggacc    4380
acttctgcgc tcggcccttc cggctggctg gtttattgct gataaatctg gagccggtga    4440
gcgtgggtct cgcggtatca ttgcagcact ggggccagat ggtaagccct cccgtatcgt    4500
agttatctac acgacgggga gtcaggcaac tatggatgaa cgaaatagac agatcgctga    4560
gataggtgcc tcactgatta agcattggta actgtcagac caagtttact catatatact    4620
ttagattgat ttaaaacttc attttaatt taaaaggatc taggtgaaga tcctttttga    4680
taatctcatg accaaaatcc cttaacgtga gttttcgttc cactgagcgt cagacccgt     4740
agaaaagatc aaaggatctt cttgagatcc ttttttctg cgcgtaatct gctgcttgca     4800
aacaaaaaaa ccaccgctac cagcggtggt ttgtttgccg gatcaagagc taccaactct    4860
ttttccgaag gtaactggct tcagcagagc gcagatacca aatactgtcc ttctagtgta    4920
gccgtagtta ggccaccact tcaagaactc tgtagcaccg cctacatacc tcgctctgct    4980
aatcctgtta ccagtggctg ctgccagtgg cgataagtcg tgtcttaccg ggttggactc    5040
aagacgatag ttaccggata aggcgcagcg gtcgggctga acggggggtt cgtgcacaca    5100
gcccagcttg gagcgaacga cctacaccga actgagatac ctacagcgtg agctatgaga    5160
aagcgccacg cttcccgaag ggagaaaggc ggacaggtat ccggtaagcg gcagggtcgg    5220
aacaggagag cgcacgaggg agcttccagg gggaaacgcc tggtatcttt atagtcctgt    5280
cgggtttcgc cacctctgac ttgagcgtcg atttttgtga tgctcgtcag gggggcggag    5340
cctatggaaa aacgccagca acgcggcctt tttacggttc ctggccttt gctggccttt     5400
tgctcacatg ttctttcctg cgttatcccc tgattctgtg gataaccgta ttaccgcctt    5460
tgagtgagct gataccgctc gccgcagccg aacgaccgag cgcagcgagt cagtgagcga    5520
ggaagcggaa gagcgcccaa tacgcaaacc gcctctcccc gcgcgttggc cgattcatta    5580
atgcaggtat cacgaggccc tttcgtcctc ac                                  5612
```

MB9 scFv Translation recombinant human antibody fragment

```
MAEVQLVQSG AEVNKPGASV KVSCKASGYT FTGYYMHWVR QAPGQGLEWM GWINPNSGGT     60
NYAQKFQGWV TMTRDTSIST AYMELSRLRS DDTAVYYCAR GRALYNRNDR SPNWFDPWGQ    120
GTLVTVSSGS ASAPTLKLEE GEFSEARVQA VLTQPPSVSV APGQTARITC GGNNIGSKSV    180
QWYQQKPGQA PVLVVYDDSD RPSGIPERFS GSNSGNMATL TISRVEAGDE ADYYCQVWDS    240
SSDHVVFGGG TKLTVLGQPK AAPSVTLFPP SAAAGSHHHH HH                       282
```

ANTIBODY OF HUMAN ORIGIN SPECIFICALLY BINDING TO ACTIVATED STATE OF PLATELET INTEGRIN RECEPTOR GPIIB/IIIA

This application is a National Stage of International Application PCT/EP02/11154, filed Oct. 4, 2002, published Apr. 17, 2003 under PCT Article 21(2) in English; which claims the priority of EP 01123851.6 filed Oct. 5, 2001.

FIELD OF THE INVENTION

The present invention is directed to an antibody for inhibiting platelet aggregation, and a method for identifying and/or isolating such an antibody. Furthermore, the present invention concerns the DNA coding for this antibody and a pharmaceutical or diagnostic preparation containing the antibody or its coding DNA.

BACKGROUND OF THE INVENTION

Platelets or thrombocytes play a crucial role in the field of thrombosis, myocardial infarction and unstable angina: The platelet integrin receptor GPIIb/IIIa is of particular importance since it mediates platelet aggregation by binding of the bivalent plasma molecule fibrinogen. This receptor has at least two conformational states: 1) A non-activated state, which is the default state on unstimulated platelets. In this non-activated state, the receptor demonstrates a very low affinity for its ligands and is not capable of inducing platelet aggregation. 2) An activated state which is present after platelet activation, e.g. by thrombin. In this activated state GPIIb/IIIa has undergone a conformational change, which leads to high affinity binding of fibrinogen (Shatill et al., J. Biol. Chem. 1985: 260(20): 11107-11114).

Consequently the therapeutic blockade of GPIIb/IIIa is a very effective anti-platelet strategy, since it affects the final common endpoint of the platelet activation cascade. During the last years a great variety of GPIIb/IIIa-blockers have been developed. These are either chimeric mouse/human Fab-fragments of a GPIIb/IIIa-blocking monoclonal antibody (Abciximab) (Coller B., et al., J. Clin. Invest. 1983, 72: 325-338), cyclic peptides (Eptifibatide) or polycyclic synthetic peptidomimetics (e.g. Tirofiban) (Bhatt D L and Topol E J. JAMA. 2000; 284(12):1549-58; Topol E J, et al., Lancet. 1999; 353 (9148):227-31). This therapy has been proved to be effective but there still retain some problems in this context:

- especially under the therapy with Abciximab, an increased prevalence of severe thrombocytopenia is present (~1%) (Dasgupta H., et al., Am Heart J. 2000; 140(2):206-11).
- due to the expensive production the costs of the therapy are considerably high, especially for Abciximab. (Hillegass W B, et al., Pharmacoeconomics. 2001; 19(1):41-55).
- there is an increase in bleeding complications which are especially important when GPIIb/IIIa-blockers are combined with thrombolysis.
- synthetic GPIIb/IIIa-blockers which are administered orally brought disappointing results, due to their pharmacokinetic properties, particularly a rather low affinity for the receptor. (Chew D P. et al., Circulation. 2001; 103(2):201-206).
- there is evidence that GPIIb/IIIa-blocker, especially the low molecular agents, interact with the receptor after binding. This might result in a paradoxical intrinsic activating effect (Peter K., et al., Blood. 1998; 92(9):3240-) reversibility of the effect of Abciximab is very slow (>12 hours)
- approx. 6% of the patients treated with Abciximab develop anti-human-chimeric antibodies (AHAC); 11% in case of patients treated repeatedly (Gawaz M., Therapie bei koronarer Herzerkrankung. Stuttgart, New York: Thieme, 1999).

All GPIIb/IIIa-blockers, currently used, are binding to the activated and non-activated receptor with similar affinity. An activation specific inhibitor might offer several advantages. For example platelet adhesion would still be intact which should result in a reduction of bleeding events. Moreover interactions with the non-activated receptor would be prevented. It would be desirable to develop a smaller GPIIb/IIIa-blocking agent with an affinity similar to an antibody, which should demonstrate better pharmacokinetic properties.

Another application for an activation specific antibody would be the detection of activated platelets, which is very useful in a variety of research and diagnostic-settings.

SUMMARY OF THE INVENTION

It is the object of the present invention to find an antibody with such improved properties, as well as to provide methods for identifying such an antibody.

This object is solved by providing the antibody according to independent claim 1. Further advantageous features, embodiments and aspects of the present invention will become more readily understandable when looking at the further independent and dependent claims, the description and the drawings.

Accordingly, the invention is directed to an antibody of human origin for inhibiting platelet aggregation, characterised in that it is effective by substantially exclusive binding to the activated state of platelet integrin receptor GPIIb/IIIa.

BRIEF DESCRIPTION OF THE DRAWINGS

FIG. 2a shows the nucleic acid sequence (SEQ ID NO: 1) of clone MB9 coding for a scFV antibody according to the present invention. FIG. 2b shows the amino acid sequence of MB9 (SEQ ID NO: 159).

FIG. 3 shows the sequence of C9 scFv (SEQ ID NO: 2) and E4 scFv (SEQ ID NO: 3).

FIG. 4 shows oligonucleotides (SEQ ID NOs: 5-22) used for the construction of the human scFv based synthetic library. BbsI restriction enzyme recognition sites are indicated in bold style, cut sites are underlined FIG. 5 shows a schematic representation of annealing positions of oligonucleotides used for the construction of pEXHAM4/C9 and pEXHAM4/E4. Genes of the scFv's C9 and E4 cloned in pEXHAM1 are shown as boxes. Black painted areas represent CDR regions; Oligonucleotides are represented by arrows and identified by numbers (c.f. FIG. 4). BpiI restriction endonuclease recognition sites are indicated.

FIG. 6 shows vector maps of pEXHAM4/C9 and pEXHAM4/E4

FIG. 7 shows vector maps of pEXHAM7/C9 and pEXHAM7/E4

FIG. 8 lists oligonucleotides (SEQ ID Nos: 23-77) used as primers in 1. PCR for amplification of human heavy and light chain variable regions FIG. 9 lists oligonucleotides (SEQ ID Nos: 78-132) used as primers in 2 PCR for introduction of restriction endonuclease recognition sequences (Marked in bold style)

FIG. 11 shows the entire nucleotide sequence (SEQ ID NO: 134) concerning the vector map pEXHAM4/E4.

FIG. 12 shows the entire nucleotide sequence (SEQ ID NO: 133) concerning the vector map pEXHAM4/C9.

FIG. 13 shows the entire nucleotide sequence (SEQ ID NO: 136) concerning the vector map pEXHAM7/E4.

FIG. 14 shows the entire nucleotide sequence (SEQ ID NO: 135) concerning the vector map pEXHAM7/C9

FIG. 17). BpiI restriction endonuclease recognition sited are indicated.

FIG. 17 shows oligonucleotides (SEQ ID Nos: 137-157) used for the construction of the human scFv based synthetic VL library. BbsI restriction enzyme recognition sited are indicated bold, cut sites are underlined.

FIG. 19 shows the amino acid sequences (SEQ ID NOs: 160 and 161) of original MB9 scFv linker (italic) connecting VH and VL-domaines (underlined) and shortened linker (italic) for diabody formation.

FIG. 20 shows the localisation and features of heavy and light chain fragments of MB9 Fab in pREFAB9.

FIG. 21 shows the binding of MB9 Fab (dark grey curve) to activated but not to non-activated human thrombocytes (mean fluorescence intensities are indicated).

FIG. 22 shows the sequence (SEQ ID NO: 158) of pREFAB9/MB9 plasmid, and MB9 scFv translation recombinant human antibody fragment (SEQ ID NO: 159).

DETAILED DESCRIPTION OF THE INVENTION

Figure 1:
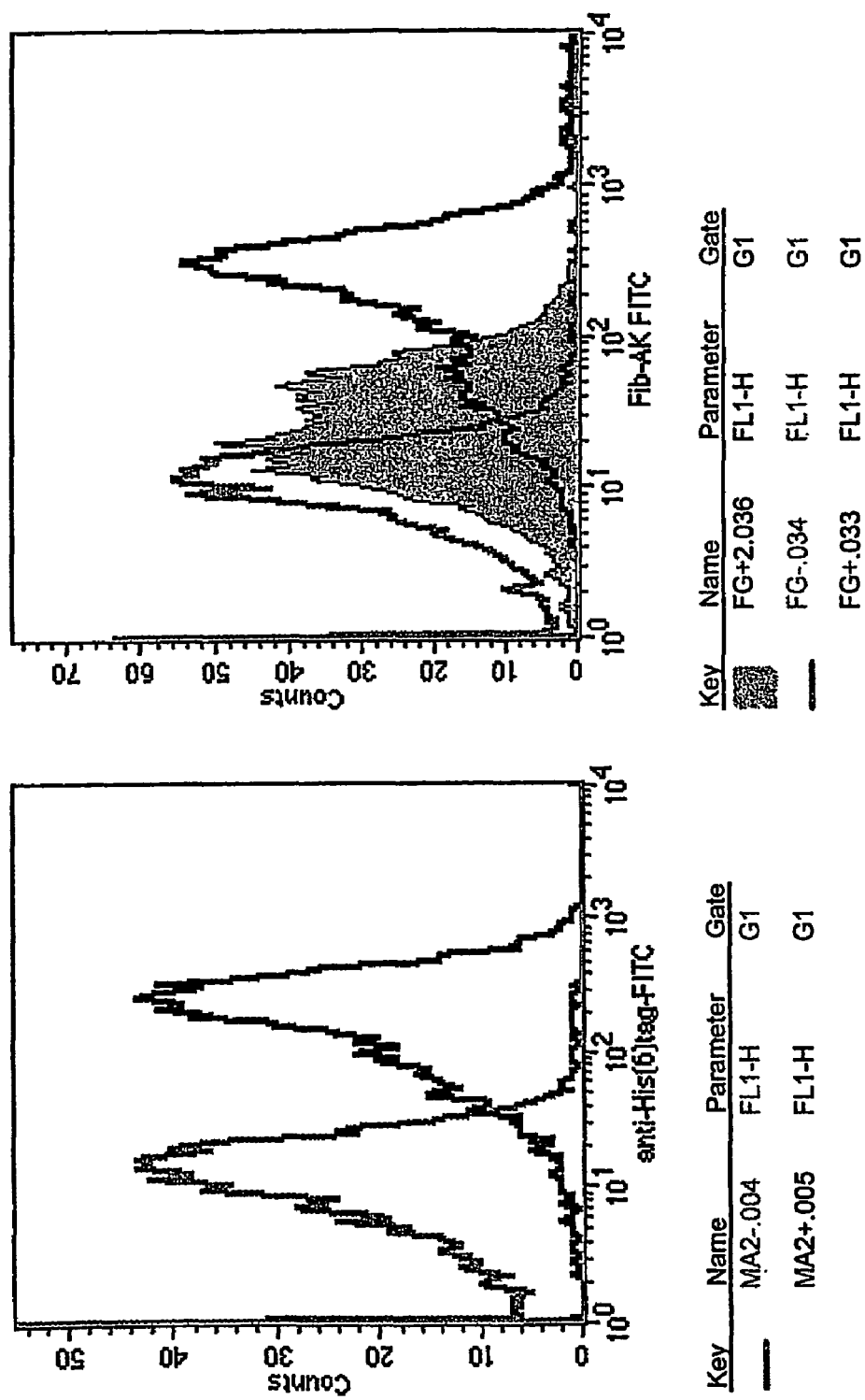
FIG. 1 shows a FACS analysis of a clone expressing an antibody fragment according to a first embodiment of the invention.

The terms thrombocyte and platelet are used synonymously in this specification. The general term "platelet integrin receptor" means "platelet integrin receptor GPIIb/IIIa".

According to the present invention, the antibody binds to the platelet integrin receptor GPIIb/IIIa (alpha IIb/beta 3) and inhibits the binding of the natural ligand fibrogen. As detailed above, this receptor is characterised by inducing the aggregation process when fibrinogen binds to it. Through blocking this receptor, crosslinking is impossible.

Due to the more selective effects obtainable, the antibody does "substantially exclusively bind" to the activated conformation of the platelet integrin receptor. This means that its binding affinity to the activated conformation of the platelet integrin receptor is much greater than its respective affinity for binding to the inactive conformation of the platelet integrin receptor. At best, the agent is substantially unable to bind to the nonactivated conformation of the integrin receptor.

In the present specification, the term "antibody" means immunoglobulins of human origin. The immunoglobulin may be also a fragment of human immunoglobulins comprising the variable domains of the heavy and light chain. The fragment may be a single chain antibody fragment (scFv), Fab or recombinant constructs and derivatives thereof. It may be monovalent, bivalent or multivalent.

It can contain modifications to its amino acid sequence when compared to genuine antibodies and exhibit a modified domain structure. It must however, still be able to adopt the typical domain configuration found in native antibodies, as well as an amino acid sequence, which is able to bind to targets (antigens) with high specificity. Typical examples of antibodies derivatives are antibodies coupled to other polypeptides, rearranged antibody domains or fragments of antibodies. The antibody may also comprise at least one further compound, e.g. a protein domain, said protein domain being linked by covalent or non-covalent bonds. The linkage can be based on genetic fusion according to the methods known in the art. The additional domain present in the fusion protein comprising the antibody employed in accordance with the invention may preferably be linked by a flexible linker, advantageously a peptide linker, wherein said peptide linker comprises plural, hydrophilic, peptide-bonded amino acids of a length sufficient to span the distance between the C-terminal end of the further protein domain and the N-terminal end of the antibody or vice versa. The above mentioned fusion protein may further comprise a cleavable linker or cleavage site for proteinases. Thus, e.g., the antibody might be linked to an effector molecule having a conformation suitable for biological activity or selective binding to a solid support, a biologically active substance (e.g. a cytokine or growth hormone), a chemical agent, a peptide, a protein or a drug.

The antibody of the present invention is of human origin. This is a particularly important feature of the invention, since it opens the use of such antibodies to a therapy in human patients without the risk of adverse immune reactions against other "foreign" antibody types. In particular, the overall structure/sequence and the constant regions of the used antibody are of human origin. The source of the human antibody may be a phagedisplay library of natural or modified human antibody fragments, screened for antibodies with affinity for thrombocytes.

Preferably, the antibody is a single chain antibody where a VH domain is linked to a VL domain. The term "linked" means preferably a peptide bond. Such a single chain antibody is preferably a recombinant scFv antibody. Methods for producing such a single chain antibody with the above mentioned properties or of DNA sequences coding for such an antibody, its expression in suitable hosts and its recovery and purification are described for examples in WO-A-89/09622, WO-A-89/01783, EP-A-0 239 400, WO90/07861 and Colcher et al., Cancer Research 49 (1989), p. 1732-1745. The scFv employed may be a recombinant construct of single chain antibody fragment(s), if such rearrangements or changes to the sequence are necessary in order to obtain the desired product. The person skilled in the art knows methods how to modify the respective immunoglobuline domains, e.g. via amino acid deletion, insertions, substitutions and/or recombinations. Methods for introducing such modifications in the coding sequence for the immunoglobuline chain are known to person skilled in the art (e.g. Sambrook et al., Molecular Cloning—A Laboratory Manual, Cold Spring Harbor (1989), N.Y.) On the other hand, the single chain antibody fragment may for example be derived from a human IgM or IgG antibody. Alternatively, recombinant BsAb or diabodies (containing two scFv fragments preferably linked via a peptide linker) can be formed. It will be also advantageously to construct tandem diabodies by homodimerisation of single chain fragments comprising four antibody variable domains (VH and VL) of two different specificities.

Due to the huge variability of the antibody generation process in the course of an immune response, in general a large number of different sequences suitable for attacking a foreign antigen can be produced. It is clear to the skilled person that therefore, several embodiments of antibody sequences could be found for meeting the requirements of the present invention. As an example, which is tested and worked well, the antibody according to the invention may be characterized in that the fragment comprises an amino acid region, which comprises the translation product of the nucleic acid sequence of FIG. 2 (SEQ. No. 1). In a further preferred embodiment, it comprises the amino acid sequence as shown in FIG. 2 or it consists of the amino acid sequence of FIG. 2. In a further embodiment, the present invention provides nucleic acid molecules encoding a fragment, derivative or allelic variation of the above polypeptide, which have substantially the same properties as that of FIG. 2. The term "derivative" in this context means that the sequence of these molecules differ from the sequences of the nucleic acid molecules and/or of the amino acid sequence of FIG. 2 at one or several positions but have a high level of homology to these sequences. Homology hereby means a sequence identity of at least 60%, in particular an identity of at least 70 or 80%, preferably of more than 90% and particularly preferred of more than 95%. The deviations of the above-mentioned nucleic acid molecules or peptide molecules may have been produced by deletion, substitutions, insertions or recombination.

Another suitable example is a synthetic library of antibody sequences. The identified fragment comprises a heavy chain CDR3 domain which contains the sequence ELEAYCRGD-CYPPYYG or a derivative thereof with comparable structure and properties. This sequence is found to be able of binding to the integrin receptor, may be because it can mimic the fibrinogen structure.

A further preferred embodiment concerns the DNA sequence coding for the single chain antibody. These DNA sequences can be inserted into a vector or expression vector. Thus, the present invention also relates to vectors and expression vectors containing these DNA sequences. The term "vector" means a plasmid (pUC18, pBR322, PBLUESCRIPT® (nucleic acid vectors for gene cloning, gene characterization, and gene transfer), etc.), a virus or any other suitable vehicle. In a preferred embodiment, the DNA sequences are functionally linked to regulatory elements, which allow their expression in procaryotic or eucaryotic host cells. Such vectors contain besides the regulatory elements (e.g. promoter) a replication origin and specific genes which allow the phenotypic selection of a transformed host cell. The regulatory elements for the expression in procaryotes (e.g. E. coli) are lac-, trp-promoter or T7 promoter, and for the expression in eucaryotes A0X1- or Gal promoter (for expression in yeasts) and CMV-, SV40-, RVS-40 promoter, CMV- or SV40 enhancer (for expression in animal cells). Further examples for promotors are metallothein I and polyhderin promoter. Suitable expression vectors for E. coli are pGEMEX, pUC derivatives, pEXHAM and pGEX-2T. Suitable promoters for the expression in yeast are pY100 and Ycpad1 and for the expression in mammal cells pMSXND, pKCR, pEFBOS, cDM8 and pCEV4.

General methods known in the art can be used for the construction of the expression vectors, which contain the DNA sequences of the present invention and suitable regulatory elements. Examples of these techniques are in-vitro recombination techniques, synthetic methods and in-vivo recombination techniques (c.f. Sambrook et al., Molecular Cloning—A Laboratory Manual, Cold Spring Harbor (1989), N.Y.). The DNA sequences according to the present invention may be also inserted into a vector in combination with DNA sequences coding for other proteins or peptides to be expressed as fusion proteins.

The present invention further concerns host cells containing these vectors. These host cells are e.g. bacteria (e.g. E. coli strains XL1blue, HB101, DH1, x1776, JM101, JM109, BL21 and SG13009), Yeasts (preferably S. cervisiae), insect cells (preferably sf9 cells) and animal cells (preferably mammal cells). Preferred mammal cells are myeloma cells, preferably mouse myeloma cells). Methods for transforming these host cells, methods for the phenotypic selection of transformants and for the expression of the DNA sequences according to the present invention by using the aforementioned vectors are known in the present technical field.

The present invention further relates to a method for the recombinant production of the (single chain) antibody by using the aforementioned expression vectors. This method comprises the cultivation of the aforementioned host cells under conditions which allow the expression (preferably stable expression) of the protein (or fusion protein) and the recovery of the protein from the culture or from the host cells. The person skilled in the art knows conditions how to cultivate transformed or transfected host cells. Suitable methods for the recombinant production of proteins are known (e.g. Holmgren, Annual Rev. Biochem. 54 (1985), 237; La Valle et al., Bio/Technology 11 (1993), 187, Wong, Curr. Opin. Biotech. 6 (1995), 517; Davies, Curr. Opin. Biotech 6 (1995), 543). Furthermore, suitable purification methods are known (e.g. preparative chromatographie, affinity chromatographie, HPLC etc.).

The invention is further directed to a process for identifying and/or isolating antibodies for inhibiting platelet aggregation by binding to the activated form of integrin receptor GPIIb/IIIa of blood thrombocytes.

Such process according to the invention comprises the following steps:
  providing a library of nucleic acids encoding for sequences of candidates;
  producing a phage library from said nucleic acids library;
  successively reacting said phage library with nonactive thrombocytes, active thrombocytes, other cells expressing nonactive integrin receptor molecules, and other cells expressing active integrin receptor molecules; and
  eluting phages bond to said thrombocytes or other cells expressing active integrin receptor molecules.

An important step of the inventive process is that the phage library is depleted of less suitable polypeptides, which either bind to nonactivated platelets, or to other components on the surface of activated platelets. Following each of the binding steps, a recovery of the selected phages should be performed, which can be done with known methods. Finally, those phages carrying polypeptides which specifically bind to the integrin receptor, are tested for their blocking activity.

The steps of selecting with other cells can be also omitted. By this modification, phages inhibiting platelet aggregation by other mechanisms may be detected.

The step of providing a library may comprise the following steps:
isolating whole RNA from human donors;
isolating mRNA contained in the whole RNA coding for antibody polypeptides;
generation of cDNA; and
deriving DNA molecules coding for single chain fragments from cDNA molecules coding for antibody polypeptides.

By this, a "natural library", based on the antibody population of the donors, can be obtained Alternatively, a synthetic library may be used, wherein the step of providing a library comprises the following steps:
providing a nucleic acid containing a sequence for a single chain antibody fragment containing a heavy and a light variable domain; and
introducing at least one randomised nucleotide sequence in a region of said single chain antibody fragment.

The region into which the at least one randomised nucleotide sequence is introduced, preferably is the CDR3 region of vH or vL such a scFv.

Said other cells may preferably be CHO cells, which are well known and may express the integrin receptor on their surface after having been transformed.

The invention is further directed to the use of a pharmaceutical composition containing the antibody, DNA or expression vectors according to the present invention for blocking the platelet integrin receptor on thrombocytes.

The invention is still further directed to the use of the antibody, DNA or expression vector according to the invention for manufacturing a pharmaceutical composition.

The subject matter of the present invention is also of diagnostic interest. It may be used for determining the number of activated thrombocytes in relation to non-activated thrombocytes in a patient. It is particular useful for monitoring the (de)activation status if the patient is treated with thrombocyte aggregation inhibitors.

The pharmaceutical or diagnostic composition may contain additionally a pharmaceutically acceptable carrier. Suitable carriers are phosphate buffered saline solutions, Water, emulsions (e.g. water-in-oil emulsions), surfactants, sterile solutions etc. The administration of the pharmaceutical composition may be orally or parenterally (e.g. topically, intraarterially, intramuscularly, subcutaneously, intramedullarly, intrathecally, intraventricularly, intraveneously, intraperitoneally or intranasally). The suitable dosage will be determined by the medical doctor and is dependent on various conditions (e.g. age, sex, weight of the patient, kind of illness and kind of administration, etc.).

The DNA sequences of the present invention may be also inserted into a vector suitable for gene therapy, e.g. under the control of a tissue-specific promoter. In a preferred embodiment the vector containing the DNA sequences is a virus (e.g. an adenovirus, vaccinia virus or adeno-associated virus). Preferred are retroviruses. Examples of suitable retroviruses are MoMuLV, HaMuSV, MuMTV, RSV or GaLV. For gene therapy purposes the DNA sequences according to the present invention may be also transported in form of colloidal dispersions to the target cells; In this connection also liposomes and lipoplexes are mentioned (Mannino et al., Biotechniques 6 (1988), 682).

Finally, the invention is directed to a method a treating a patient, comprising the following step:

administering a pharmaceutical composition according to the invention in a pharmaceutically effective dose to the patient.

In the following, examples for the production of human scFv antibodies specific for activated platelet integrin receptor GPIIb/IIIa will be given.

EXAMPLES

General Strategy

Phage libraries for the display of single chain antibody fragments (scFv) are generated from human IgM antibody genes. Alternatively, a synthetic library is generated by randomization of the CDR3 region of the heavy chain in two scFv master frameworks of human origin. Both libraries are subtracted for not activation specific binders by incubation on resting thrombocytes prior to using them for selection on activated platelets. To focus the selection onto the GPIIbIIIa receptor, additional rounds of selection are done on in vitro cultivated cells expressing recombinant GPIIbIIIa receptor. Following the selection, scFv clones are analysed for binding to activated thrombocytes and competition of fibronogen binding by FACS analysis.

Example 1

Production of the Human scFv Antibody Fragment MB9

RNA and cDNA Preparation

Total RNA is isolated from spleen samples of six human donors and peripheral blood lymphocytes (PBL) of five healthy human donors (app. 1–5×10$^8$ PBLs each, RNeasy™ Midiprep.Kit, Qiagen). From total RNA poly A$^+$-RNA is prepared (Oligotex mRNA Kit, Qiagen) and used for cDNA synthesis (SuperScript™ Preamplifications System, Gibco BRL/LIFE Technologies).

Amplification of Human Ig Variable Regions

Oligonucleotides used in PCR for amplification of variable regions of human immunoglobulin heavy and light chains those of FIG. 8. Heavy chains are amplified using a single IgM specific constant primer and one of a number of different primers (VH-1 to VH-7) specific for the variable region in separate PCR reactions. Accordingly lambda and kappa light chains are amplified using a single lambda or kappa specific constant primer and one out of a number of different variable primers (Vλ-1 to Vλ10 and Vκ-1 to 6). PCR is done in a volume of 50 µl using 0.5 µl cDNA, 1 unit VENT$_R$® exo$^-$-DNA-polymerase (DNA polymerase genetically engineered to eliminate the 3'→5' proofreading exonuclease activity associated with Vent® DNA Polymerase New England Biolabs) and 0.5 µM of each primer under following conditions: 3 min 95° C., 20×[30 sec 95° C., 1 min 55° C., 1 min 72° C.] 5 min 72° C. The products of the first PCR are purified using the PCR purification Kit (Qiagen) and used as templates for as second PCR using a corresponding set of oligonucleotide primers of FIG. 9 to introduce restriction sites for cloning. The second PCR is carried out separately for each primer set according to the first PCR but using 1 min 57° C. for annealing. Products of the second PCR of the heavy chain, the lambda light chain and the kappa light chain are pooled and purified via PCR-purification Kit (Qiagen).

Cloning of the scFv Phage Display Library

Heavy chain fragments are digested with NcoI and HindIII, light chain fragments with MluI and NotI (each New England Biolabs) according to the suppliers instructions and finally purified by gel extraction from 1% agarose gels using the Gel Extraction Kit (Qiagen). To create a sublibrary, the heavy chains are cloned first into the phagedisplay vector pEX-HAM1 (FIG. 1) containing a stuffer scFv. Vector DNA is cut with NcoI and HindIII, purified via gel extraction and ligated separately with heavy chain fragments originating from different donors. Ligation is done in 20 µl volume using 50 ng vector, 9 ng heavy chain fragment and 1 unit T4 DNA-ligase (Roche) for three hours at room temperature. The ligation mixture is precipitated, resuspended in 10 µl water and mixed with 35 µl of electrocompetent *E. coli* XL1 blue cells (Stratagene) for electroporation according to the suppliers instructions. Transformed cells are plated on selective LB agarose plates containing 50 mM glucose, 100 µg/ml ampicillin and 20 µg/ml tetracyclin and incubated at 30° C. over night. The size of the sublibraries is in the range of $1.5 \times 10^6$ to $7.1 \times 10^7$ as determined by plating appropriate dilutions.

Bacterial clones are scraped from the plates and used for DNA-maxipreparation (Qiagen) to prepare the vector DNA for cloning of the complete libraries. Sublibrary DNA is cut with MluI and NotI, purified by gel extraction and ligated with lambda and kappa light chain fragments separately. Ligation is done in 20 µl volume using 1 µg vector DNA and a two fold molar excess of light chain DNA. After incubation with 1 unit T4 ligase (Roche) over night at 8° C., the ligation mixture is precipitated and redissolved in 2.5 µl Tris 10 mM, pH8.5. Of this 2 µl are used for transformation of 50 µl aliquots of electrocompetent XL1 blue cells. Cells are plated on selective agarplates and the number of transformants is determined by plating of appropriate dilutions as described above. The total size of all libraries generated from spleen and PBL RNA material is $1.75 \times 10^9$.

Library Rescue

For phage display of scFv's, the library is inoculated in 250 ml aliquots of LB medium supplemented with 50 mM glucose, 100 µg/ml ampicillin and 20 µg/ml tetracyclin at a start OD600 of 0.025 ensuring that the number of cells exceeds the complexity by a factor of 10. Cells are incubated at 37° C. and 200 rpm until an OD600 of 0.2 and infected with M13K07 helperphages at a multiplicity of infection of 10. After one hour incubation at 37° C. cells are harvested by centrifugation, resuspended in 250 ml glucose free medium and incubated over night at 30° C. and 200 rpm. Phage are isolated by PEG precipitation (PEG6000 20%, NaCl 2.5M) and redissolved in phage dilution buffer (Tris 10 mM pH 7.5, NaCl 20 mM, EDTA 2 mM).

Screening the Library for scFv's Binding Activated Platelets

Depletion of the Library for scFV's Binding Non Activated Platelets:

5 ml of human, venous blood are collected in a S MONOVETTE® (Sarstedt, blood taking apparatus) containing 25 µl prostaglandine E20 (10 mM) and centrifuged at 110 g for 10 min. Of platelet rich plasma (upper phase), 1 ml is transferred into a fresh tube, mixed with 9 ml CGS-buffer (sodium citrate 10 mM, dextrose 30 mM, NaCl 120 mM) and centrifuged at 1000 g for 10 min. The pellet is resuspended in 4 ml tyrode buffer (NaCl (150 mM), NaHCO3 (12 mM), KCl, MgCl (2 mM each), glucose, BSA (1 mg/ml each), pH 7.4) containing 2% skimmed milk powder and incubated with $1.75 \times 10^{12}$ bacteriophages (1000× complexity) for 2 hours at room temperature. Platelets are centrifuged at 1000 g for 10 min, the supernatant removed and stored at 4° C., Binding onto Activated Platelets:

5 ml of human, venous blood are collected in a S-MONOVETTE® (Sarstedt) and centrifuged at 110 g for 10 min. Of platelet rich plasma (upper phase), 1 ml is transferred in a fresh tube, mixed with 9 ml CGS-buffer and centrifuged at 1000 g for 10 min. The pellet is resuspended with 4 ml depleted phage solution containing $CaCl_2$, $MgCl_2$ (2 mM each), ADP (15 µM) and incubated at room temperature for 2 hours. Platelets are washed twice by centrifugation (1000 g, 10 min) and resuspended in 14 ml tyrode buffer.

Elution:

For elution of binding phage, the platelets are centrifuged (1000 g, 10 min), resuspended in 1 ml glycine buffer (0.1 M, pH 2.2) and incubated for 10 min at room temperature. After centrifugation (1000 g, 10 min) the supernatant is neutralized by addition of Tris (2 M, pH 8.0).

Reinfection:

Eluted phages are mixed with 10 ml of logarithmic growing *E. coli* XL1 blue cells and incubated at 37° C. for 30 min. After centrifugation (10 min, 6000 g), cells are resuspended in 400 µl $LB_{GAT}$ medium (LB medium containing 50 mM glucose, 100 µg/ml ampicillin and 20 µg/ml tetracyclin), plated on $LB_{GAT}$ agarplates and incubated over night at 37° C.

Packaging:

Colonies are scraped from agar plates using two times 5 ml $LB_{GAT}$ medium and used for inoculation of 20 ml $LB_{GAT}$ medium at an OD600 of 0.1. Cells are incubated at 37° C. and 200 rpm for one hour and superinfected with about $1 \times 10^{10}$ M13K07 helperphages. After one hour at 37° C., cells are collected by centrifugation (5 min, 6000 g) resuspended in LB medium supplemented with ampicillin (100 µg/ml) and kanamycin (50 µg/ml) and incubated over night at 30° C. and 200 rpm. Phages are collected by PEG precipitation and resuspended in 1 ml phage dilution buffer (as described for library rescue).

Screening the Library for scFv's Binding Recombinant GPIIb/IIIa on CHO-Cells

Depletion of scFv's Binding Non Activated GPIIb/IIIa:

Chinese hamster ovary cells (CHO) expressing non activated GPIIb/IIIa receptor (A5 cells; Peter et al., Blood, Vol. 9, 1998, pp. 3240-3249) are trypsinated, centrifuged (10 min, 140 g) and resuspended at $5 \times 10^6$ cells/ml in tyrode buffer. About $10^9$ packaged phage from the first round of selection are mixed with 4 ml cell suspension and incubated for one hour at room temperature. Cells are centrifuged for 20 min at 140 g and the supernatant cleared again by centrifugation (20 min, 3200 g).

Binding on Activated GPIIb/IIIa:

CHO cells presenting active GPIIb/IIIa (Cl3 cells, Peter K and O'Toole T E, J Exp Med. 1995, 181(1): 315-326) are harvested by trypsination, centrifuged and washed once using 1 ml tyrode buffer. $4 \times 10^6$ cells are incubated with 4 ml depleted phage solution for 30 min at room temperature.

Elution by Antibody Competition:

Cells are centrifuged for 10 min at 140 g, resuspended in 50 ml tyrode buffer, three times centrifuged for 20 min at 700 g and resuspended in 1 ml tyrode buffer and finally resuspended in 200 µl REOPRO® (pharmaceutical preparations for the prevention and treatment of diseases of the circulatory system) (2 mg/ml). After 20 min at room temperature, cells are removed by 10 min centrifugation at 13000 rpm in a benchtop centrifuge.

Acidic Elution:

Cells are centrifuged for 10 min at 140 g, resuspended in 50 ml modified tyrode buffer (tyrode buffer pH 6 adjusted with Hepes, containing $CaCl_2$, $MgCl_2$ (2 mM each) and 1 mg/ml BSA), twice centrifuged for 20 min at 700 g and resuspended in 1 ml modified tyrode buffer and finally resuspended in 1 ml glycine (pH 2.2). After 15 min at room temperature the mixture is neutralized by addition of 100 µl Tris (2 M, pH 8) and cleared by centrifugation at 13000 rpm for 10 min in a benchtop centrifuge.

Reinfection and packaging: is done as described above.

Restriction Endonuclease Digestion Analysis of Selected Clones

DNA of clones from selection experiments are prepared using DNA spin columns following the recommendations of the manufacture (Quiagen). DNA is digested with BstNI (New England Biolabs) and analysed on a 1% agarose gel.

Preparation of Periplasmic Extracts 5 ml of $LB_{GAT}$ medium are inoculated with 250 µl of an overnight culture and incubated at 37° C. and 180 rpm for 4 hours. Cells are harvested by centrifugation (5 min, 6000 g) resuspended in 5 ml LB medium containing ampicillin (10 µg/ml) and IPTG (100 µM) and incubated at 28° C. and 180 rpm over night. Cells are again harvested by centrifugation and resuspended in 500 µl shock solution (50 mM Tris HCl pH 8.0, 20% saccharose, 1 mM EDTA) and incubated at 8° C. for one hour. Cells are removed by centrifugation (10 min, 13000 rpm benchtop centrifuge) and the supernatant dialysed two times 3 hours against PBS at 4° C.

FACS-Analysis

FACS-analysis is done using a FACSCALIBUR™ (automated, multicolor flow cytometry system) device (Becton Dickinson).

Analysis of Activation Specificity:

Complete citrate blood (S MONOVETTE®, Sarstedt) is diluted 1/50 in 50 µl tyrode buffer with or without ADP (20 µM) and incubated for 20 min at room temperature with 10 µl of periplasmic scFv extracts. As secondary antibody FITC labelled anti-His-antibody (Dianova) is added, incubated for 20 min and fixed with CELLFIX™ (immunomagnetic tools, namely, magnetic nanoparticles and devices for cell separation, manipulation, collection and presentation for analysis, for use in laboratory research tests) (1×).

Analysis of Fibrinogen Competition:

Complete citrate blood (S MONOVETTE®, Sarstedt) is diluted 1/50 in 50 µl tyrode buffer with or without ADP (20 µM) and incubated for 20 min with FITC labeled anti-fibrinogen-antibody (WAK-Chemie Medical) in presence or absence of 20 µl of periplasmic scFv extracts before fixation with CELLFIX™ (1×, Becton Dickinson).

Aggregometry Measurements:

Aggregometry was performed using a Biodata PAP-AG-GREGOMETER™ (an instrument for simultaneous performance of a routine aggregation profile) according to the manufacturer's recommendations. After incubation with the scFv for 10 min at 37° C. the aggregation was induced by addition of 20 µM.

Results

Selection of GPIIb/IIIa Binding scFv's

Human scFv phagedisplay libraries originating from spleen and PBL are screened for GPIIb/IIIa specific clones by selection on activated human platelets for one round. The library is depleted before on not activated platelets to remove not activation-specific binders. The second and third round of selection is done on CHO cells expressing recombinant, activated GPIIb/IIIa receptor after depletion on cells presenting a not activated variant. Elution is done either by acid or by competition with REOPRO®. After the third round of selection clones are randomly picked and analysed first for enrichment by BstN1 digestion and activation-specific binding to thrombocytes (Table 1). One clone, MB9, is found to be enriched using acidic as well as competitive elution to 10 of 80 clones and 10 of 60 clones respectively. MB9 is also strongly activation-specific in platelet binding and inhibits binding of fibrinogen to platelets as shown by FACS-analysis depicted in FIG. 1. Therein, the following is depicted: Left histogram: demonstrates binding of MB9 scFv to activated (black) but not to unactivated (grey) human thrombocytes.

Right histogram: Binding of fibrinogen to activated (black) but not to unactivated thrombocytes. Binding of fibrinogen to activated thrombocytes is inhibited in presence of MB9 scFv (filled bright grey curve).

Additionally MB9 competes with REOPRO® for binding. Other enriched clones like MA1 also show activation of specific binding but fail in inhibition of fibrinogen binding or are not strongly specific for activated thrombocytes like MA3 or MB1.

The DNA sequence of clone MB9 is given in SEQ ID No. 1 (FIG. 2). Restriction endonuclease recognition sequences flanking heavy and light chains (NcoI, HindIII and MluI, NotI respectively) are indicated.

A clone encoding MB9 has been deposited under DSM 14491 (XL1blue (pEXHAM4/MP9)) on Sep. 6, 2001 with the "Deutsche Sammlung von Mikroorganismen und Zellkulturen GmbH, D-38124 Braunschweig" under the Budapest Treaty.

TABLE 1

Characterization of scFv clones enriched on activated GPIIb/IIIa.

| Clone | elution done by | Enrichment Identical clones/ analysed clones | Activation specific binding to human platelets | inhibition of fibrinogen binding | competition by REOPRO® |
|---|---|---|---|---|---|
| MA1 | Acid | 20/80 | ++ | − | − |
| MA2 | Acid | 10/80 | ++ | ++ | + |
| MA3 | Acid | 24/80 | + | − | − |
| MB1 | Competition | 21/60 | + | + | + |
| MB9 Identical to MA2 | Competition | 10/60 | ++ | ++ | + |

++: strongly positive;
+: positive;
−: negative

Figure 15A:
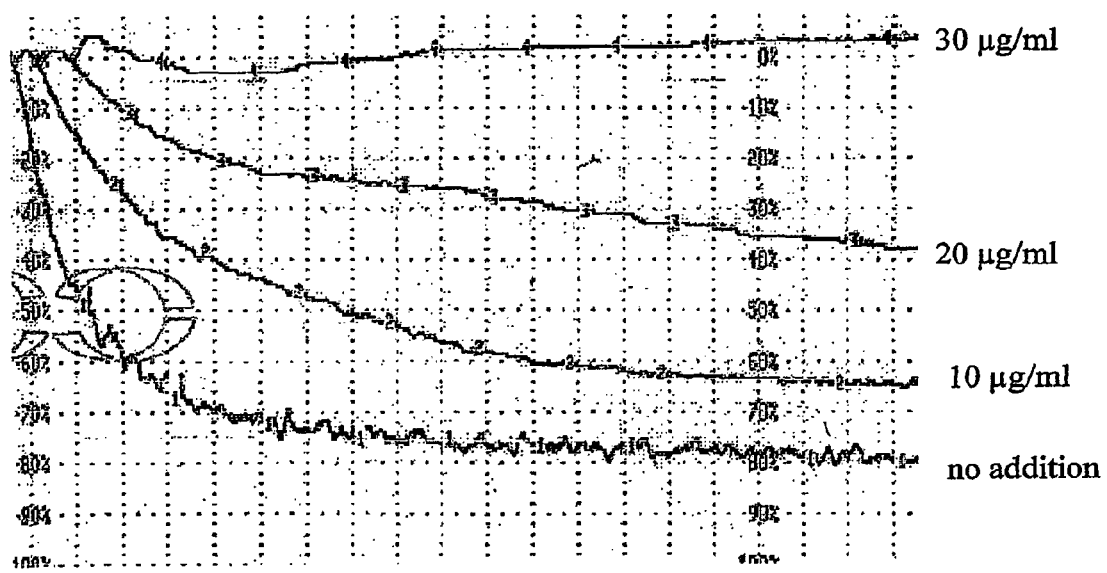
FIG. 15a shows aggregometry with MB9 scFv. Inhibition of platelet aggregation by addition of MB9 scFv in different concentrations. Aggregation was monitored by the increase of light transmission.
Figure 15B:
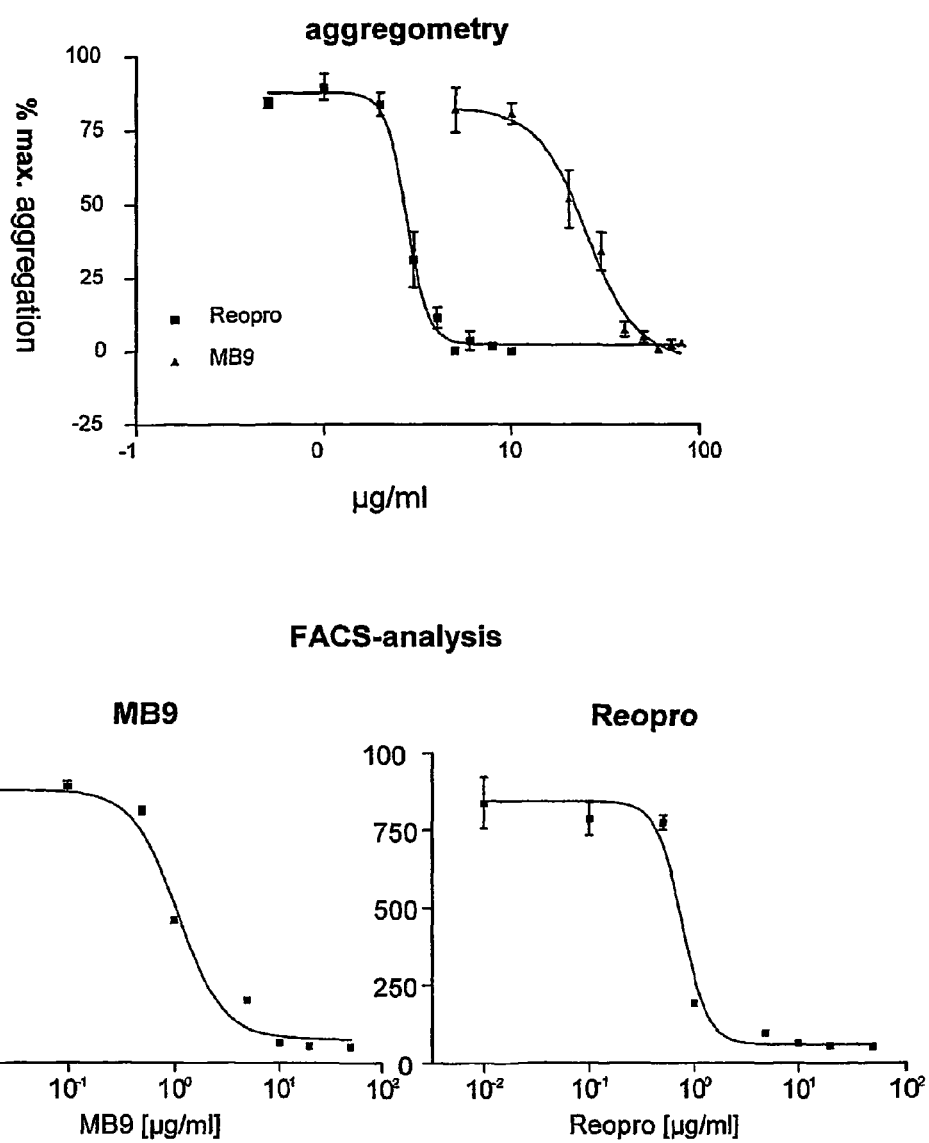
FIG. 15b shows the comparison of Reopro and MB9 binding to activated throbocytes by aggregometry and FACS analysis

For MB9 scFv inhibition of aggregation of activated human platelets in presence of fibrinogen in a concentration dependent manner has been demonstrated by aggregometry (FIG. 15a). By this method half maximal inhibition of platelet aggregation was achieved with MB9 scFv (31 kDa) at 25 µg/ml (806 nM) and with REOPRO® (Fab, 50 kDa) at 2.7 µg/ml (54 nM), whereas half maximal inhibition of fibrinogen binding in FACS was reached at 1.1 µg/ml (35 nM) for MB9 and 0.75 µg/ml (15 nM) for REOPRO® (FIG. 15b).

Example 2

Production of the Synthetic Human Framework Based scFv Antibody Fragment

Origin of Human scFv Master Frameworks

For the generation of a synthetic library by randomization of the CDR3 region of the heavy chain two human master frameworks (C9 and E4, FIG. 3) are chosen because of their excellent production characteristics in *E. coli* cells. Both scFv's originate from a large human phage display antibody library (Little, M., et al., J. Immunol. Methods 1999, 231: 3-9) and specific for hepatitis B virus antigen (C9) and estradiol (E4) respectively.

Vector Construction for the Synthetic scFv Library

C9 and E4 scFv's are cloned in pEXHAM1 vector DNA replacing the stuffer scFv by standard recombinant cloning techniques using NcoI and NotI cloning sites.

To prepare a vector allowing the randomization of CDR3 of the heavy chain without changes of the original sequence this region is replaced by a stuffer DNA fragment containing restriction enzyme recognition sites of the type IIS enzyme BpiI (BbsI). Standard PCR reactions are set up using the oligonucleotid primers as shown in FIG. 4 to generate DNA fragments of the scFv regions 3' and 5' of the heavy chain CDR3 containing unique BpiI cloning sites as outlined in FIG. 5, which is a schematic representation of annealing positions of oligonucleotides used for the construction of pEXHAM4/C9 and pEXHAM4/E4. Genes of the scFv's C9 and E4 cloned in pEXHAM1 are shown as boxes. Black painted areas represent CDR regions; Oligonucleotides are represented by arrows and identified by numbers (cp. sequence definitions). BpiI restriction endonuclease recognition sites are indicated.

The stuffer DNA fragment is generated directly by hybridisation of synthetic oligonucleotides. DNA-fragments are cut with BpiI and cloned in BpiI digested pEXHAM1 vector DNA to generate pEXHAM4/C9 and pEXHAM4/E4 (FIGS. 6, 11 and 12).

Figure 13A:
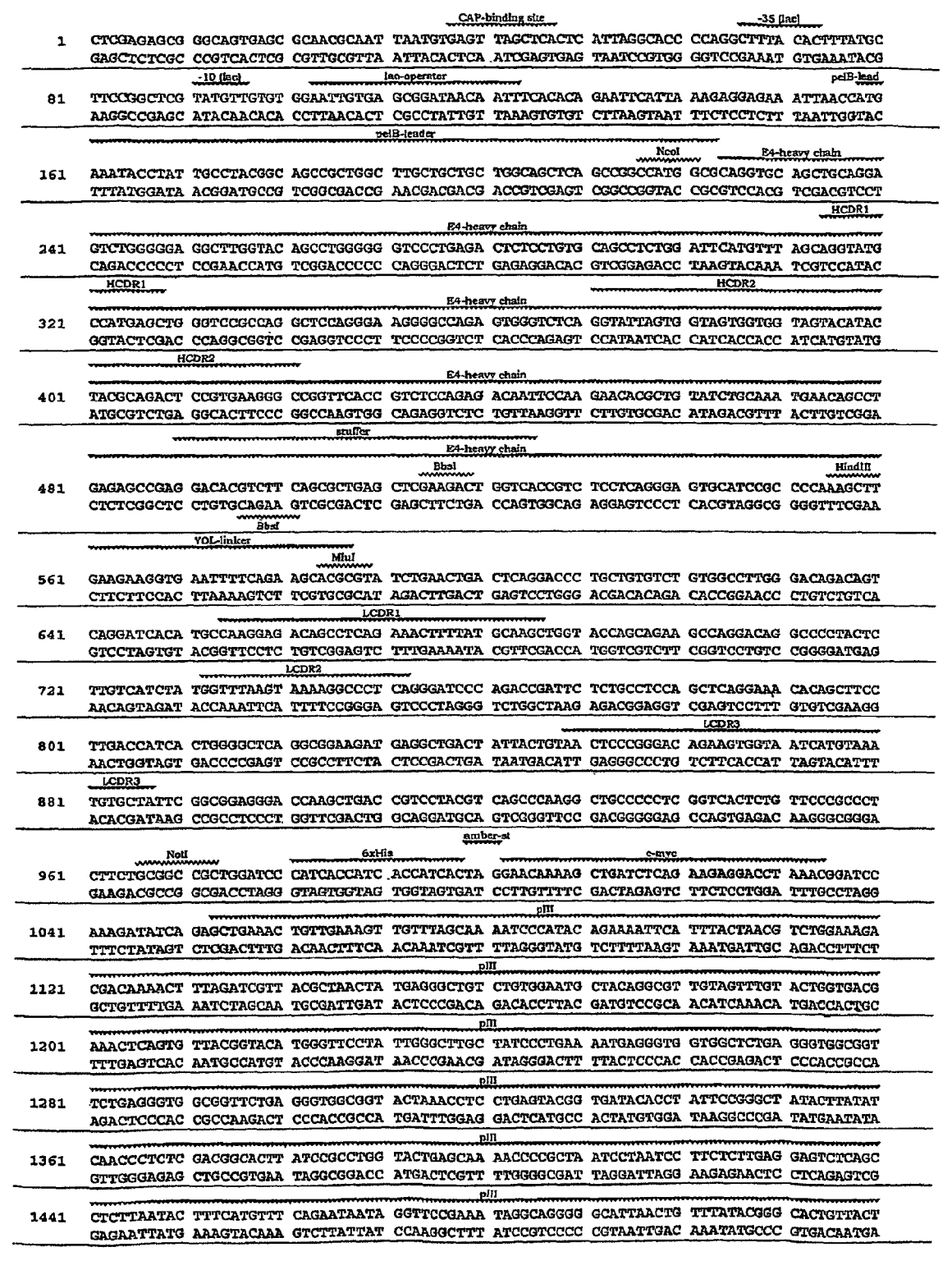
Figure 13C:
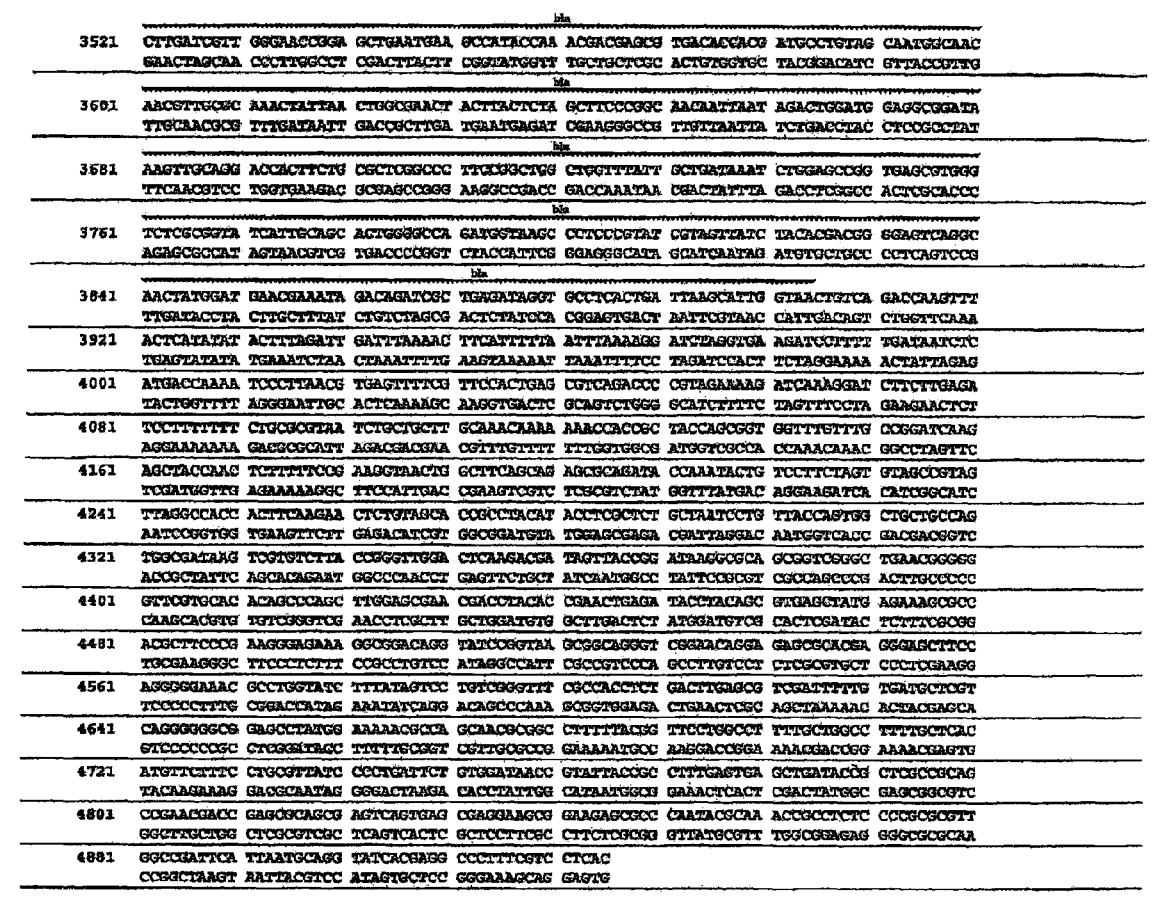

Direct use of pEXHAM4 vector DNA for cloning via BbsI necessitates the purification of two vector fragments, 3.8 and 0.5 kb in size. To avoid this both BbsI restriction sites outside the scFv sequence are removed in several steps without changing the protein sequence using mismatched oligonucleotides as primers for PCR or directly hybridised synthetic oligonucleotides to replace BbsI containing DNA-fragments by cloning via neighboring restriction sites. The final constructs is named pEXHAM7/C9 and pEXHAM7/E4 (FIGS. 7, 13 and 14) respectively.

Generation of the Synthetic, Human Framework Based scFv Library

To generate a library synthetic oligonucleotides encoding four to seven random amino acids by NNK codons (VH-CDR3_3.4/cut until VHCDR3_3.7/cut; 1 µM each) are filled in separately using oligonucleotides VHCDR3_for/cut and VHCDR3_back/cut (0.2 µM) (FIG. 4) with 1 unit VENT® exo⁻DNA-polymerase (New England Biolabs) unter following PCR conditions: 2 min 94° C., 5×[1 min 94° C., 1 min 40° C., 1 min 72° C.] 10 min 72° C. in 100 µl Volume. PCR-products are purified using PCR purification Kit (Qiagen). ⅔ of the material is cut with 100 units BbsI for 6 hours and again purified via the mentioned kit. In case of VHCDR3_3.4/cut and VHCDR3_3.5/cut the vector DNA pEXHAM4/C9 and pEXHAM4/E4 is cut with BbsI (1 unit/µg in 6 hours) and both vector fragments (3.8 and 0.5 kb) are purified via gel elution from a 1 agarose gel (Gel Extraction Kit, Qiagen). For VHCDR3_3.6/cut and VHCDR3_3.7/cut pEXHAM6/C9 and pEXHAM6/E4 are used, therefore only one vector fragment had to be purified. Ligation is done in all cases at an equimolar ratio of all fragments. Afterwards the ligation mixture is precipitated, redissolved in Tris 10 mM, pH8.5 and used for transformation of XL1 blue cells essentially as described for example 1.

In addition to synthetic randomized DNA-fragments, CDR3 of the heavy chain is also replaced by natural CDR3 sequences amplified from the products of the first PCR of the natural library (see example 1) to focus on functional, in vivo used sequences for this region. Oligonucleotides used and described in FIG. 4 are designed to cover most of the human heavy chain CDR3 regions without modifying C9 or E4 framework sequences. PCR is done separately for each human VH PCR template using 1 unit VENT® exo⁻-DNA polymerase (New England Biolabs) and 0.2 µM primer in a volume of 100 µl under following conditions: 2 min 94° C., 30×[1 min 95° C., 1 min 50° C., 1 min 72° C.] 10 min 72° C. Oligo nucleotides #42, #43 and #44 are used as an equimolar mixture. PCR products are purified via PCR purification kit and material originating from spleen or PBL respectively is pooled. Restriction with BbsI, ligation with pEXHAM6/C9 and pEXHAM6/E4 respectively and transformation is done as described above.

The size of the whole synthetic library (synthetic and natural CDR3's cloned in C9 or E4 frameworks) in this example is 7.5×10⁸ clones.

Library Rescue

Packaging of synthetic libraries is done as described for the natural library (example 1).

Screening of the Synthetic Library

Screening of the synthetic library is done exactly as described for the natural library (example 1) starting with 7.5×10¹¹ bacteriophages (1000× complexity).

Results

The synthetic library derived from human scFv frameworks (C9 and E4) is screened for GPIIb/IIIa specific clones exactly as described in example 1. After the third round of selection clones are randomly picked and the DNA sequence of the VH-CDR3 regions was determined (c.f. Table 2)

TABLE 2

Analysis of the DNA-Sequence of VH-CDR3 of eleven GPIIb/IIIa selected clones from the synthetic library (SEQ ID Nos: 162-169).

| clone | Translation of VH-CDR3 DNA | No of identical clones | Oligonucleotide used for CDR3 |
|---|---|---|---|
| SA1 | CAR RYRVG FDY (SEQ ID NO: 162) | 1 | VHCDR3_3.5/cut |
| SA2 | CAR GATYTSRSDVPDQTS FDY (SEQ ID NO: 163) | 2 | VHCDR3_ev2/for/cut |
| SA3 | CAR DDLAYCRGDCSGRFA FDI (SEQ ID NO: 164) | 2 | VHCDR3_ev2/for/cut |
| SA4 | CAR RFSISRA FDY (SEQ ID NO: 165) | 1 | VHCDR3_3.7/cut |

TABLE 2-continued

Analysis of the DNA-Sequence of VH-CDR3 of eleven GPIIb/IIIa selected clones from the synthetic library (SEQ ID Nos: 162-169).

| clone | Translation of VH-CDR3 DNA | No of identical clones | Oligonucleotide used for CDR3 |
|---|---|---|---|
| SA6 | CAR RWGKARS FDY (SEQ ID NO: 166) | 1 | VHCDR3__3.7/cut |
| SA8 | CAK ELEAYCRGDCYPPYYG MDV (SEQ ID NO: 167) | 1 | VHCDR3__ev3/for/cut |
| SA10 | CAR DLFGRGDYGDYG MDV (SEQ ID NO: 168) | 1 | VHCDR3__ev2/for/cut |
| SA11 | CAR TYYYDSRTDRRPPHA FDI (SEQ ID NO: 169) | 1 | VHCDR3__ev3/for/cut |

Figure 10:
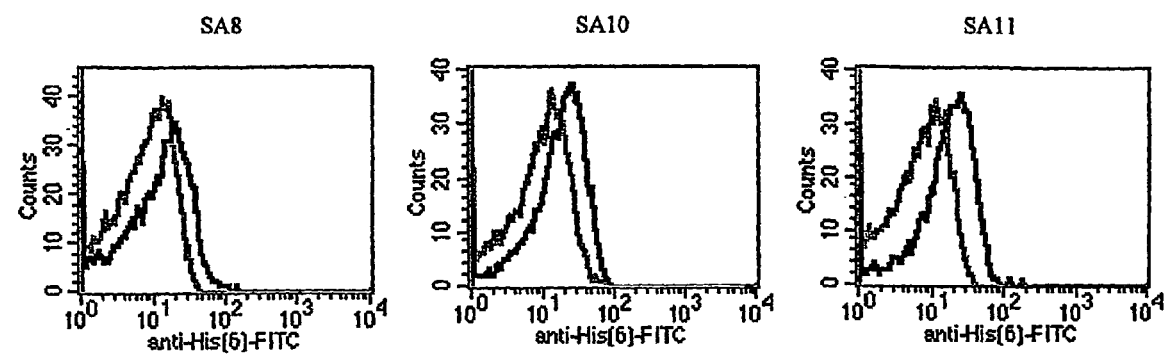
FIG. 10 shows the FACS analysis of clones SA8, SA10 and SA11. Binding of indicated scFv's to activated (black curve) and non-activated (grey curve) thrombocytes.

All of the clones use the E4 framework sequence. Three of the eleven analysed clones encode the amino acid sequence RGD (also present in fibrogen) within CDR3 (SA3, SA8 and SA10). In clones SA3 and SA8 the RGD motive is directly flanked by two cysteine residues that might stabilize the loop by disulfide bridges. Clone SA3 was found twice under eleven analysed clones and, therefore, has probably enriched by the screening procedure. The same is true for clone SA11. These scFv clones are similar to antibodies like PAC-1 that contain RGD-like sequences and inhibit fibrogen binding by blocking the activated receptor (Shatill et al., 1985). Only SA8, Sa10 and SA11 showed an activation specific binding to thrombocytes in the presence of fibrinogen (c.f. FIG. 10).

The selected clones probably interact exactly with the fibrinogen binding site of the GPIIb/IIa receptor but with an affinity similar or lower than fibrinogen. The affinity has been enhanced by mutation within the VH and/or the VL-domain of the scFv antibody fragment or the exchange of the whole VL domain ("chain shuffling).

Example 3

Figure 16:
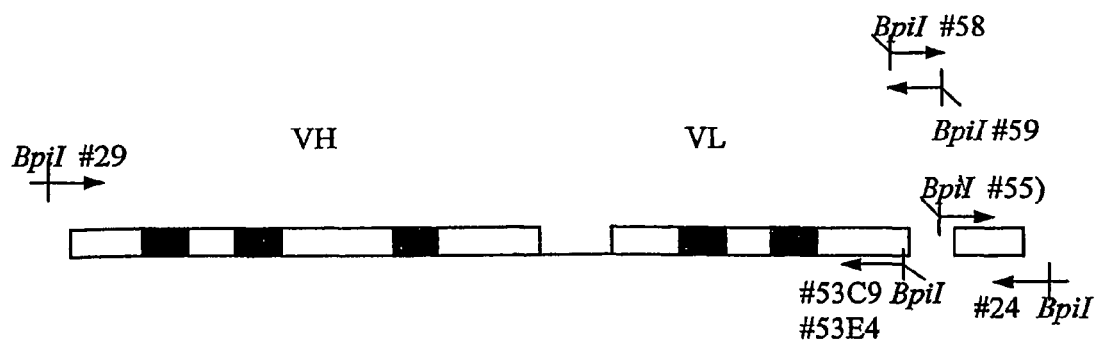
FIG. 16 shows the schematic representation of annealing positions of oligonucleotides used for the construction of pEXHAM9/C9 and pEXHAM9/E4. Genes of the scFV's C9 and E4 cloned in pEXHAM1 are shown in boxes. Black boxes represent CDR regions; oligonucleotides are represented by arrows and identified by numbers (c.f.

Improvement of GPIIb/IIIa Specific Synthetic scFv Fragments by Light Chain Shuffling Vector Construction:

CDR3 sequences of the variable domain of the light chain of C9 and E4 scFv in pEXHAM1 were replaced by a synthetic stuffer introducing flanking BbsI restriction sites as outlined in FIG. 16. Standard PCR reactions were set up using the oligonucleotides shown in FIG. 17 to amplify the DNA-Fragments of the scFv regions in 3' and 5' direction of the light chain CDR3. PCR-fragments were purified cleaved with BbsI. The stuffer CDR3 fragment was generated directly by hybridisation of the indicated oligos. All three fragments were ligated with BbsI digested pEXHAM1 vector-DNA to generate pEXHAM9/C9 and pEXHAM9/E4 respectively. To remove additional BbsI sites the light chain fragments of pEXHAM9/C9 and pEXHAM9/E4 were recloned in pEXHAM6/C9 and pEXHAM6/E4 using MluI and NotI sites to generate pEXHAM10/C9 and pEXHAM10/E4. To facilitate the cloning of randomized VLCDR3 sequences, a 1.5 kb DNA fragment amplified from bacteriophage lambda DNA (bp 15629-17152) using standard PCR reactions and primer LAM1 and LAM2 (FIG. 17) was introduced via SacI between BbsI sites in the stuffer region of pEXHAM10 derivatives to create pEXHAM11(C9) and pEXHAM11/(E4).

Generation of a Synthetic, Human Framework scFv Based Light Chain Library

To generate a VL library, synthetic oligos encoding four to six random aminoacids by NNK-codons (C9VLCDR3__4/cut until C9VLCDR3__6/cut and E4VLCDR3__4/cut until E4VLCDR3__6/cut, FIG. 17) were filled in separately essentially as described in example 2 using oligos C9VLCDR3_for/cut and C9VLCDR3_back/cut or E4VLCDR3_for/cut and E4VLCDR3_back/cut (FIG. 17). PCR-products were cut with BbsI and ligated with BbsI digested vector DNA fragments of pEXHAM11/C9 and pEXHAM11/E4 respectively and used for transformation of E. coli XL1blue cells essentially as described for example 1.

In addition to the synthetic randomised DNA-fragments, CDR3 of the light chain was replaced also by natural VLCDR3-sequences. Vλ genes amplified in the first PCR on human cDNA from PBL and spleen as described in example 1 were used as a template to amplify VLCDR3 essentially as described in example 2 using oligos VLCDR3_ev/for/cut and VLCDR3_ev/back/cut (FIG. 17). PCR-products were cloned after BbsI digestion in pEXHAM11/C9 and pEXHAM11/E4 and used for the transformation of E. coli XL1blue as described above.

The overall size of the VL-library is $3.6 \times 10^7$ clones for the C9 framework and $4.7 \times 10^7$ for the E4 framework.

Generation of GPIIb/IIIa Specific scFv-Sublibaries by Chain Shuffling

ScFv clones SA2, SA3, SA8, SA10 and SA11 described in example 2 were selected for chain shuffling. VL genes of these clones were replaced via MluI and NotI sites by randomised VL genes from the E4 VL-library using standard cloning procedures. By repeated transformations of E. coli XL1blue separate sublibraries of $2.6 \times 10^7$ until $6.5 \times 10^7$ clones were generated.

Library Rescue

Packaging of the sublibraries was done as described in example 1.

Screening of GPIIb/IIIa Specific Sublibraries

Five rounds of panning were performed on activated GPIIb/IIIa-expressing CHO-cells essentially as described for example 1, but using only 105 CHO cells. During the first four rounds bound phages were eluted by low pH and in the fifth round by increasing concentrations of Eptifibatide (0.1-1000 μg/ml). Phages eluted with 100 μg/ml were further investigated.

Results

Figure 18:
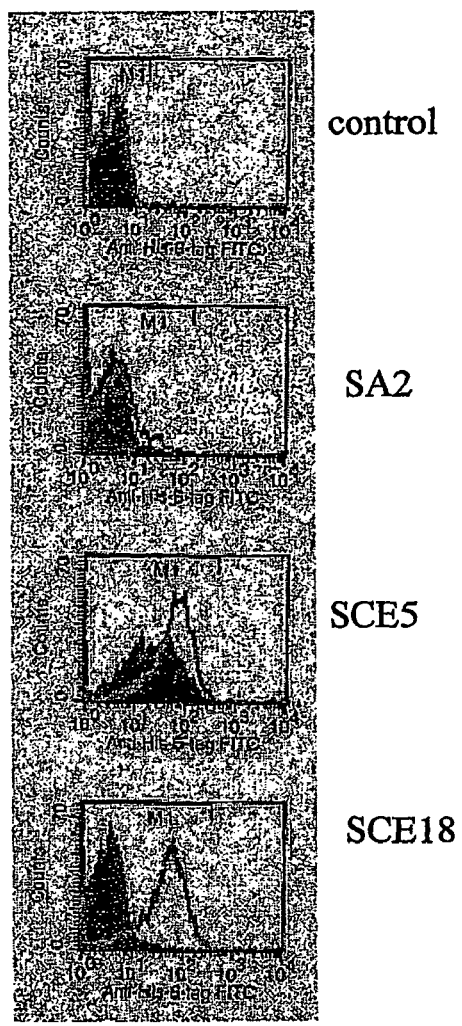
FIG. 18 shows the FACS analysis of affinity maturated scFv SCE5 and SCE18. Binding of scFv preparations of SA2 (original cloned) and light chain shuffled derivatives SCE5 and SCE18 to non activated (filled black curve) and activated (grey curve) thrombocytes. Measurement was done with whole blood in presence of fibrinogen. "Control" demonstrates no binding of secondary anti-H is antibody.

Five scFv clones isolated from the synthetic library and showing an RXD-motif in CDR3 of the heavy chain (SA2, SA3, SA8, SA10 and SA11, see example 2) were selected for affinity maturation by chain shuffling. For each clone the constant light chain domains were replaced by an E4 light chain library with randomised synthetic or natural CDR3 regions. These sublibraries were screened again on GPIIb/IIIa presenting CHO-cells using acidic elution for four rounds of panning. In the fifth round elution was done by increasing concentrations of Eptifibatide, a low molecular weight GPIIb/IIIa inhibitor (RGD-mimetic), to select clones with increased affinity. Single clones were analysed first by FACS for binding to activated platelets. Most of the clones showed increased but nonuniform binding to activated platelets. By subsequent DNA-sequencing no strong enrichment of single clones was observed. Two clones, SCE5 and SCE18, were identified that stained all activated platelets in an uniform manner (FIG. 18). Both clones are derived from the SA2 framework and have similar light chain CDR3 sequences (SCE5: CLLYYGGGQQGVFGGG, SEQ ID NO: 170; SCE18: CLLYYGGAWVFGGG, SEQ ID NO:171).

Example 4

Converting GPIIb/IIIa Specific scFv in Other Formats

MB9 scFv was converted into different recombinant antibody formats to generate variants possibly improved e.g. in terms of size, stability or affinity.

MB9 Diabody

To increase the size of MB9, a diabody can be generated for example by reducing the linker between VH and VL to generate a molecule that is not able to form a functional scFv but a non-covalently linked homodimer bearing two antigen binding sites. Such a diabody was generated by shortening the original linker to three amino acids (FIG. 19) using standard PCR methods. Absence of scFv monomers and presence of dimeric (and multimeric) forms has been demonstrated by size exclusion chromatography for this MB9 derivative as well as inhibition of fibrinogen binding to activated platelets.

MB9 Fab

To convert MB9 scFv into a Fab format the variable domains of the heavy and light chains were amplified separately by PCR and cloned into the Fab-Vector pREFAB9 (FIG. 20) in front of CH1 and Clambda respectively. The sequence is shown in FIG. 22. FACS-analysis of periplasmic preparations of the MB9 Fab demonstrated specific binding of MB9 Fab to activated human thrombocytes (FIG. 21).

The invention claimed is:

1. An Antibody of human origin, wherein said antibody inhibits platelet aggregation and has a greater binding affinity to the activated state of platelet integrin receptor GPIIb/IIIa than to the inactive conformation of the platelet integrin receptor GPIIb/IIIa, wherein the antibody comprises the heavy and light chain variable domains of the amino acid sequence of SEQ ID NO: 159.

2. An antibody derivative, wherein said derivative is a bivalent or multivalent antibody construct comprising the variable domains of the heavy and light chains of an antibody of human origin, wherein said antibody of human origin inhibits platelet aggregation and has a greater binding affinity to the activated state of platelet integrin receptor GPIIb/IIIa than to the inactive conformation of the platelet integrin receptor GPIIb/IIIa, wherein said antibody derivative specifically binds to the activated state of platelet integrin receptor GPIIb/IIIa and inhibits platelet aggregation, wherein said antibody derivative comprises:

(i) a heavy chain variable domain comprising CDR1 and CDR2 of the heavy chain variable domain encoded by nucleic acids comprising nucleotides 4 to 399 of SEQ ID NO: 3 and CDR3 having the sequence as set forth in SEQ ID NO: 163 and a light chain variable domain comprising CDR1 and CDR2 of the light chain variable domain encoded by nucleic acids comprising nucleotides 427 to 810 of SEQ ID NO: 3 and CDR3 having the sequence as set forth in SEQ ID NO: 170 or SEQ ID NO: 171; or (ii) a light chain variable domain encoded by nucleic acids comprising nucleotides 427 to 810 of SEQ ID NO: 3, wherein the CDR3 encoded by SEQ ID NO: 3 is replaced by a CDR3 having the sequence as set forth in SEQ ID NO: 170 or SEQ ID NO: 171; or (iii) a heavy chain variable domain encoded by nucleic acids comprising nucleotides 4 to 399 of SEQ ID NO:3, wherein the CDR3 encoded by SEQ ID NO:3 is replace by a CDR3 having the sequence as set forth in SEQ ID NO: 163.

3. An Antibody of human origin which specifically binds to the activated state of platelet integrin receptor GPIIb/IIIa and inhibits platelet aggregation, wherein said antibody is a single chain antibody fragment or a Fab fragment or comprising the variable domains of the heavy and light chains of a single chain antibody fragment or a Fab fragment, wherein said antibody comprises the heavy and light chain variable domains of the amino acid sequence of SEQ ID NO: 159.

4. An Antibody of human origin which specifically binds to the activated state of platelet integrin receptor GPIIb/IIIa and inhibits platelet aggregation, wherein said antibody is a single chain antibody fragment or a Fab fragment or comprising the variable domains of the heavy and light chains of a single chain antibody fragment or a Fab fragment, wherein said antibody comprises
  (i) a heavy chain variable domain comprising CDR1 and CDR2 of the heavy chain variable domain encoded by nucleic acids comprising nucleotides 4 to 399 of SEQ ID NO: 3 and CDR3 having the sequence as set forth in SEQ ID NO: 163 and a light chain variable domain comprising CDR1 and CDR2 of the light chain variable domain encoded by nucleic acids comprising nucleotides 427 to 810 of SEQ ID NO: 3 and CDR3 having the sequence as set forth in SEQ ID NO: 170 or SEQ ID NO: 171; or
  (ii) a light chain variable domain encoded by nucleic acids comprising nucleotides 427 to 810 of SEQ ID NO: 3, wherein the CDR3 encoded by SEQ ID NO: 3 is replaced by a CDR3 having the sequence as set forth in SEQ ID NO: 170 or SEQ ID NO: 171; or
  (iii) a heavy chain variable domain encoded by nucleic acids comprising nucleotides 4 to 399 of SEQ ID NO:3, wherein the CDR3 encoded by SEQ ID NO:3 is replace by a CDR3 having the sequence as set forth in SEQ ID NO: 163.

5. An antibody of human origin which specifically binds to the activated state of platelet integrin receptor GPIIb/IIIa and inhibits platelet aggregation and the binding site of said antibody is formed by a variable light chain immunoglobulin domain and a variable heavy chain immunoglobulin domain, wherein the variable light chain domain is encoded by nucleic acids comprising nucleotides 427 to 810 of SEQ ID NO:3 and the heavy chain variable domain is encoded by nucleic acids comprising nucleotides 4 to 399 of SEQ ID NO:3, wherein the CDR3 of the variable heavy chain domain is replaced by SEQ ID NO:163.

6. An antibody of human origin which specifically binds to the activated state of platelet integrin receptor GPIIb/IIIa and inhibits platelet aggregation and the binding site of said antibody is formed by a variable light chain immunoglobulin domain and a variable heavy chain immunoglobulin domain, wherein the variable light chain domain is encoded by nucleic acids comprising nucleotides 427 to 810 of SEQ ID NO:3, wherein the CDR3 of the variable light chain is replaced by SEQ ID NO:170 and the heavy chain variable domain is encoded by nucleic acids comprising nucleotides 4 to 399 of SEQ ID NO:3, wherein the CDR3 of the variable heavy chain domain is replaced by SEQ ID NO:163.

7. An antibody of human origin which specifically binds to the activated state of platelet integrin receptor GPIIb/IIIa and inhibits platelet aggregation and the binding site of said antibody is formed by a variable light chain immunoglobulin domain and a variable heavy chain immunoglobulin domain, wherein the variable light chain domain is encoded by nucleic acids comprising nucleotides 427 to 810 of SEQ ID NO:3, wherein the CDR3 of the variable light chain is replaced by SEQ ID NO:171 and the heavy chain variable domain is encoded by nucleic acids comprising nucleotides 4 to 399 of SEQ ID NO:3, wherein the CDR3 of the variable heavy chain domain is replaced by SEQ ID NO:163.

* * * * *

SEQUENCE LISTING

<160> NUMBER OF SEQ ID NOS: 171

<210> SEQ ID NO 1
<211> LENGTH: 823
<212> TYPE: DNA
<213> ORGANISM: Artificial Sequence
<220> FEATURE:
<223> OTHER INFORMATION: Recombinant human antibody fragment

<400> SEQUENCE: 1

```
ccatggcgga agtgcagctg gtgcagtctg gagctgaggt gaataagcct ggggcctcag      60
tgaaggtctc ctgcaaggct tctggataca ccttcaccgg ctactatatg cactgggtgc     120
gacaggcccc tggacaaggg cttgagtgga tgggatggat caaccctaac agtggtggca     180
caaactatgc acagaagttt cagggctggg tcaccatgac cagggacacg tccatcagca     240
ccgcctacat ggagctgagc aggctgagat ctgacgacac ggccgtgtat tactgtgcga     300
gaggccgtgc tttgtataac cggaacgacc ggtcccccaa ctggttcgac ccctggggcc     360
agggaaccct ggtcaccgtc tcctcaggga gtgcatccgc cccaaccctt aagcttgaag     420
aaggtgaatt ttcagaagca cgcgtacagg ctgtgctgac tcagccgccc tcggtgtcag     480
tggccccagg acagacggcc aggattacct gtgggggaaa caacattgga agtaaaagtg     540
tgcagtggta ccagcagaag ccaggccagg cccctgtgct ggtcgtctat gatgatagcg     600
accggccctc agggatccct gagcgattct ctggctccaa ctctgggaac atggccaccc     660
tgaccatcag cagggtcgaa gccggggatg aggccgacta ttactgtcag gtgtgggata     720
gtagtagtga tcatgtggta ttcggcggag ggaccaagct gaccgtccta ggtcagccca     780
aggctgcccc ctcggtcact ctgttcccgc cgtccgcggc cgc                       823
```

<210> SEQ ID NO 2

<211> LENGTH: 808
<212> TYPE: DNA
<213> ORGANISM: Artificial Sequence
<220> FEATURE:
<223> OTHER INFORMATION: Recombinant human antibody fragment

<400> SEQUENCE: 2

```
ccatggcgca ggtacagctg caggagtctg ggggaggcgt ggtccagcct gggaggtccc      60
tgagactctc ctgtgcagcc tctggattct ccttcagtaa ttatggcata cactgggtcc     120
gccaggctcc aggcaagggg ctggagtggg tggcacttat atcatatgat ggaaataaga     180
aattctatgc agactccgtg aagggccgat tcgccatctc cagagacact tctaagaata     240
cggtggatct gcaaatgacc agcctgagac tgaggacac ggctgtatat tactgtgcga      300
aatctggggg tattgccttg tactgggggg aatttgacta ctggggccag gaaccctgg      360
tcaccgtctc ctcagcctcc accaaggggcc caaagcttga agaaggtgaa ttttcagaag    420
cacgcgtatc ctatgaactg actcagccac cctcggtgtc agtggcccca ggacagacgg     480
ccatgattac ctgtggggga acaacattg gaagtacaac cgtgcactgg tatcagcaga      540
agccaggcca ggcccctgtg ctggtcgtct atgatgataa cgagcgaccc tcagggatcc     600
ctgagcgatt ctctggctcc aactctggga gcacggccac cctgaccatc aacagggtcg     660
aagccgggga tgaggccgac tattattgtc aagtgtggga tagtggtagt gatcatgtgg     720
tattcggcgg agggacgaag ctgaccgtcc taggtcagcc caaggctgcc ccctcggtca     780
ctctgttccc gccctcctct gcggccgc                                        808
```

<210> SEQ ID NO 3
<211> LENGTH: 814
<212> TYPE: DNA
<213> ORGANISM: Artificial Sequence
<220> FEATURE:
<223> OTHER INFORMATION: Recombinant human antibody fragment

<400> SEQUENCE: 3

```
ccatggcgca ggtgcagctg caggagtctg ggggaggctt ggtacagcct gggggtccc       60
tgagactctc ctgtgcagcc tctggattca tgtttagcag gtatgccatg agctgggtcc     120
gccaggctcc agggaagggg ccagagtggg tctcaggtat tagtggtagt ggtggtagta     180
catactacgc agactccgtg aagggccggt tcaccgtctc cagagacaat tccaagaaca     240
cgctgtatct gcaaatgaac agcctgagag ccgaggacac ggccgtatat tactgtgcga     300
aagatctggg ctactatggt tcggggagcc aacccttga gtactggggc agggaactc       360
tggtcaccgt ctcctcaggg agtgcatccg ccccaaagct tgaagaaggt gaattttcag     420
aagcacgcgt atctgaactg actcaggacc ctgctgtgtc tgtggccttg gacagacag      480
tcaggatcac atgccaagga cagcctca gaaactttta tgcaagctgg taccagcaga      540
agccaggaca ggcccctact cttgtcatct atggtttaag taaaaggccc tcaggatcc      600
cagaccgatt ctctgcctcc agctcaggaa acacagcttc cttgaccatc actgggctc      660
aggcggaaga tgaggctgac tattactgta actcccggga cagaagtggt aatcatgtaa    720
atgtgctatt cggcggaggg accaagctga ccgtcctacg tcagcccaag gctgccccct    780
cggtcactct gttcccgccc tcttctgcgg ccgc                                 814
```

<210> SEQ ID NO 4
<211> LENGTH: 804
<212> TYPE: PRT
<213> ORGANISM: Artificial Sequence

```
<220> FEATURE:
<223> OTHER INFORMATION: Recombinant human antibody fragment

<400> SEQUENCE: 4

Met Glu Thr Ala Leu Ala Gly Leu Val Ala Leu Gly Leu Asn Leu Glu
1               5                   10                  15

Val Ala Leu Gly Leu Asn Ser Glu Arg Gly Leu Tyr Ala Leu Ala Gly
                20                  25                  30

Leu Val Ala Leu Ala Ser Asn Leu Tyr Ser Pro Arg Gly Leu Tyr Ala
                35                  40                  45

Leu Ala Ser Glu Arg Val Ala Leu Leu Tyr Ser Val Ala Leu Ser Glu
50                  55                  60

Arg Cys Tyr Ser Leu Tyr Ser Ala Leu Ala Ser Glu Arg Gly Leu Tyr
65                  70                  75                  80

Thr Tyr Arg Thr His Arg Pro His Glu Thr His Arg Gly Leu Tyr Thr
                85                  90                  95

Tyr Arg Thr Tyr Arg Met Glu Thr His Ile Ser Thr Arg Pro Val Ala
                100                 105                 110

Leu Ala Arg Gly Gly Leu Asn Ala Leu Ala Pro Arg Gly Leu Tyr Gly
                115                 120                 125

Leu Asn Gly Leu Tyr Leu Glu Gly Leu Thr Arg Pro Met Glu Thr Gly
130                 135                 140

Leu Tyr Thr Arg Pro Ile Leu Glu Ala Ser Asn Pro Arg Ala Ser Asn
145                 150                 155                 160

Ser Glu Arg Gly Leu Tyr Gly Leu Tyr Thr His Arg Ala Ser Asn Thr
                165                 170                 175

Tyr Arg Ala Leu Ala Gly Leu Asn Leu Tyr Ser Pro His Glu Gly Leu
                180                 185                 190

Asn Gly Leu Tyr Thr Arg Pro Val Ala Leu Thr His Arg Met Glu Thr
                195                 200                 205

Thr His Arg Ala Arg Gly Ala Ser Pro Thr His Arg Ser Glu Arg Ile
210                 215                 220

Leu Glu Ser Glu Arg Thr His Arg Ala Leu Ala Thr Tyr Arg Met Glu
225                 230                 235                 240

Thr Gly Leu Leu Glu Ser Glu Arg Ala Arg Gly Leu Glu Ala Arg Gly
                245                 250                 255

Ser Glu Arg Ala Ser Pro Ala Ser Pro Thr His Arg Ala Leu Ala Val
                260                 265                 270

Ala Leu Thr Tyr Arg Thr Tyr Arg Cys Tyr Ser Ala Leu Ala Ala Arg
                275                 280                 285

Gly Gly Leu Tyr Ala Arg Gly Ala Leu Ala Leu Glu Thr Tyr Arg Ala
                290                 295                 300

Ser Asn Ala Arg Gly Ala Ser Asn Ala Ser Pro Ala Arg Gly Ser Glu
305                 310                 315                 320

Arg Pro Arg Ala Ser Asn Thr Arg Pro Pro His Glu Ala Ser Pro Pro
                325                 330                 335

Arg Thr Arg Pro Gly Leu Tyr Gly Leu Asn Gly Leu Tyr Thr His Arg
                340                 345                 350

Leu Glu Val Ala Leu Thr His Arg Val Ala Leu Ser Glu Arg Ser Glu
                355                 360                 365

Arg Gly Leu Tyr Ser Glu Arg Ala Leu Ala Ser Glu Arg Ala Leu Ala
                370                 375                 380

Pro Arg Thr His Arg Leu Glu Leu Tyr Ser Leu Glu Gly Leu Gly Leu
385                 390                 395                 400
```

```
Gly Leu Tyr Gly Leu Pro His Glu Ser Glu Arg Gly Leu Ala Leu Ala
                405                 410                 415
Ala Arg Gly Val Ala Leu Gly Leu Asn Ala Leu Ala Val Ala Leu Leu
            420                 425                 430
Glu Thr His Arg Gly Leu Asn Pro Arg Pro Arg Ser Glu Arg Val Ala
        435                 440                 445
Leu Ser Glu Arg Val Ala Leu Ala Leu Ala Pro Arg Gly Leu Tyr Gly
    450                 455                 460
Leu Asn Thr His Arg Ala Leu Ala Ala Arg Gly Ile Leu Glu Thr His
465                 470                 475                 480
Arg Cys Tyr Ser Gly Leu Tyr Gly Leu Tyr Ala Ser Asn Ala Ser Asn
                485                 490                 495
Ile Leu Glu Gly Leu Tyr Ser Glu Leu Tyr Ser Ser Glu Arg Val
            500                 505                 510
Ala Leu Gly Leu Asn Thr Arg Pro Thr Tyr Arg Gly Leu Asn Gly Leu
        515                 520                 525
Asn Leu Tyr Ser Pro Arg Gly Leu Tyr Gly Leu Asn Ala Leu Ala Pro
    530                 535                 540
Arg Val Ala Leu Leu Glu Val Ala Leu Val Ala Leu Thr Tyr Arg Ala
545                 550                 555                 560
Ser Pro Ala Ser Pro Ser Glu Arg Ala Ser Pro Ala Arg Gly Pro Arg
                565                 570                 575
Ser Glu Arg Gly Leu Tyr Ile Leu Glu Pro Arg Gly Leu Ala Arg Gly
            580                 585                 590
Pro His Glu Ser Glu Arg Gly Leu Tyr Ser Glu Arg Ala Ser Asn Ser
        595                 600                 605
Glu Arg Gly Leu Tyr Ala Ser Asn Met Glu Thr Ala Leu Ala Thr His
    610                 615                 620
Arg Leu Glu Thr His Arg Ile Leu Glu Ser Glu Arg Ala Arg Gly Val
625                 630                 635                 640
Ala Leu Gly Leu Ala Leu Ala Gly Leu Tyr Ala Ser Pro Gly Leu Ala
                645                 650                 655
Leu Ala Ala Ser Pro Thr Tyr Arg Thr Tyr Arg Cys Tyr Ser Gly Leu
            660                 665                 670
Asn Val Ala Leu Thr Arg Pro Ala Ser Pro Ser Glu Arg Ser Glu Arg
        675                 680                 685
Ser Glu Arg Ala Ser Pro His Ile Ser Val Ala Leu Val Ala Leu Pro
    690                 695                 700
His Glu Gly Leu Tyr Gly Leu Tyr Gly Leu Tyr Thr His Arg Leu Tyr
705                 710                 715                 720
Ser Leu Glu Thr His Arg Val Ala Leu Leu Glu Gly Leu Tyr Gly Leu
                725                 730                 735
Asn Pro Arg Leu Tyr Ser Ala Leu Ala Ala Leu Ala Pro Arg Ser Glu
            740                 745                 750
Arg Val Ala Leu Thr His Arg Leu Glu Pro His Glu Pro Arg Pro Arg
        755                 760                 765
Ser Glu Arg Ala Leu Ala Ala Leu Ala Ala Leu Ala Gly Leu Tyr Ser
    770                 775                 780
Glu Arg His Ile Ser His Ile Ser His Ile Ser His Ile Ser His Ile
785                 790                 795                 800
Ser His Ile Ser
```

```
<210> SEQ ID NO 5
<211> LENGTH: 36
<212> TYPE: DNA
<213> ORGANISM: Artificial Sequence
<220> FEATURE:
<223> OTHER INFORMATION: Synthetic Oligonucleotides

<400> SEQUENCE: 5
tactacgaag acgtgtcctc aggtctcagg ctggtc                              36

<210> SEQ ID NO 6
<211> LENGTH: 36
<212> TYPE: DNA
<213> ORGANISM: Artificial Sequence
<220> FEATURE:
<223> OTHER INFORMATION: Synthetic Oligonucleotides

<400> SEQUENCE: 6
tactacgaag acgtgtcctc ggctctcagg ctgttc                              36

<210> SEQ ID NO 7
<211> LENGTH: 31
<212> TYPE: DNA
<213> ORGANISM: Artificial Sequence
<220> FEATURE:
<223> OTHER INFORMATION: Synthetic Oligonucleotides

<400> SEQUENCE: 7
aatgcaggta tcacgaggcc ctttcgtctt c                                   31

<210> SEQ ID NO 8
<211> LENGTH: 39
<212> TYPE: DNA
<213> ORGANISM: Artificial Sequence
<220> FEATURE:
<223> OTHER INFORMATION: Synthetic Oligonucleotides

<400> SEQUENCE: 8
cagctctgat atctttggat ccgtttaggt cttcttctg                           39

<210> SEQ ID NO 9
<211> LENGTH: 36
<212> TYPE: DNA
<213> ORGANISM: Artificial Sequence
<220> FEATURE:
<223> OTHER INFORMATION: Synthetic Oligonucleotides

<400> SEQUENCE: 9
tactacgaag actggtcacc gtctcctcag cctcca                              36

<210> SEQ ID NO 10
<211> LENGTH: 36
<212> TYPE: DNA
<213> ORGANISM: Artificial Sequence
<220> FEATURE:
<223> OTHER INFORMATION: Synthetic Oligonucleotides

<400> SEQUENCE: 10
tactacgaag actggtcacc gtctcctcag ggagtg                              36

<210> SEQ ID NO 11
<211> LENGTH: 32
<212> TYPE: DNA
<213> ORGANISM: Artificial Sequence
<220> FEATURE:
<223> OTHER INFORMATION: Synthetic Oligonucleotides
```

<400> SEQUENCE: 11
ggacacgtct tcagcgctga gctcgaagac tg                                          32

<210> SEQ ID NO 12
<211> LENGTH: 32
<212> TYPE: DNA
<213> ORGANISM: Artificial Sequence
<220> FEATURE:
<223> OTHER INFORMATION: Synthetic Oligonucleotides

<400> SEQUENCE: 12
tgaccagtct tcgagctcag cgctgaagac gt                                          32

<210> SEQ ID NO 13
<211> LENGTH: 75
<212> TYPE: DNA
<213> ORGANISM: Artificial Sequence
<220> FEATURE:
<223> OTHER INFORMATION: Synthetic Oligonucleotides
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t

<400> SEQUENCE: 13
gaggacacgg ctgtatatta ctgtgcgara nnknnknnkn nktttgasta ctggggccag            60
ggaaccctgg tcacc                                                             75

<210> SEQ ID NO 14
<211> LENGTH: 78
<212> TYPE: DNA
<213> ORGANISM: Artificial Sequence
<220> FEATURE:
<223> OTHER INFORMATION: Synthetic Oligonucleotides
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t

<400> SEQUENCE: 14
gaggacacgg ctgtatatta ctgtgcgara nnknnknnkn nknktttga stactggggc             60 cagggaaccc tggtcacc                                                          78

<210> SEQ ID NO 15
<211> LENGTH: 81
<212> TYPE: DNA
<213> ORGANISM: Artificial Sequence
<220> FEATURE:
<223> OTHER INFORMATION: Synthetic Oligonucleotides
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t

<400> SEQUENCE: 15
gaggacacgg ctgtatatta ctgtgcgara nnknnknnkn nknnknnktt tgastactgg    60
ggccagggaa ccctggtcac c                                             81

<210> SEQ ID NO 16
<211> LENGTH: 84
<212> TYPE: DNA
<213> ORGANISM: Artificial Sequence
<220> FEATURE:
<223> OTHER INFORMATION: Synthetic Oligonucleotides
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t

<400> SEQUENCE: 16
gaggacacgg ctgtatatta ctgtgcgara nnknnknnkn nknnknnknn ktttgastac    60

```
tggggccagg gaaccctggt cacc                                          84

<210> SEQ ID NO 17
<211> LENGTH: 40
<212> TYPE: DNA
<213> ORGANISM: Artificial Sequence
<220> FEATURE:
<223> OTHER INFORMATION: Synthetic Oligonucleotides

<400> SEQUENCE: 17
agcctggaag acgaggacac ggctgtatat tactgtgcga                         40

<210> SEQ ID NO 18
<211> LENGTH: 39
<212> TYPE: DNA
<213> ORGANISM: Artificial Sequence
<220> FEATURE:
<223> OTHER INFORMATION: Synthetic Oligonucleotides

<400> SEQUENCE: 18
ggctgagaag acggtgacca gggttccctg gccccagta                          39

<210> SEQ ID NO 19
<211> LENGTH: 36
<212> TYPE: DNA
<213> ORGANISM: Artificial Sequence
<220> FEATURE:
<223> OTHER INFORMATION: Synthetic Oligonucleotides

<400> SEQUENCE: 19
agcctggaag acgaggacac ggcygtgtat tactgt                             36

<210> SEQ ID NO 20
<211> LENGTH: 36
<212> TYPE: DNA
<213> ORGANISM: Artificial Sequence
<220> FEATURE:
<223> OTHER INFORMATION: Synthetic Oligonucleotides

<400> SEQUENCE: 20
agcctggaag acgaggacac wgccgtgtat tactgt                             36

<210> SEQ ID NO 21
<211> LENGTH: 36
<212> TYPE: DNA
<213> ORGANISM: Artificial Sequence
<220> FEATURE:
<223> OTHER INFORMATION: Synthetic Oligonucleotides

<400> SEQUENCE: 21
agcctggaag acgaggacac ggccgtatat tactgt                             36

<210> SEQ ID NO 22
<211> LENGTH: 36
<212> TYPE: DNA
<213> ORGANISM: Artificial Sequence
<220> FEATURE:
<223> OTHER INFORMATION: Synthetic Oligonucleotides

<400> SEQUENCE: 22
ggctgagaag acggtgacca gggtkccctg gccca                              36

<210> SEQ ID NO 23
<211> LENGTH: 21
<212> TYPE: DNA
<213> ORGANISM: Artificial Sequence
```

```
<220> FEATURE:
<223> OTHER INFORMATION: Primers

<400> SEQUENCE: 23
caggtgcagc tggtgcagtc t                                              21

<210> SEQ ID NO 24
<211> LENGTH: 21
<212> TYPE: DNA
<213> ORGANISM: Artificial Sequence
<220> FEATURE:
<223> OTHER INFORMATION: Primers

<400> SEQUENCE: 24
caggtccagc ttgtgcagtc t                                              21

<210> SEQ ID NO 25
<211> LENGTH: 21
<212> TYPE: DNA
<213> ORGANISM: Artificial Sequence
<220> FEATURE:
<223> OTHER INFORMATION: Primers

<400> SEQUENCE: 25
caggtccagc tggtacagtc t                                              21

<210> SEQ ID NO 26
<211> LENGTH: 21
<212> TYPE: DNA
<213> ORGANISM: Artificial Sequence
<220> FEATURE:
<223> OTHER INFORMATION: Primers

<400> SEQUENCE: 26
gaggtccagc tggtacagtc t                                              21

<210> SEQ ID NO 27
<211> LENGTH: 21
<212> TYPE: DNA
<213> ORGANISM: Artificial Sequence
<220> FEATURE:
<223> OTHER INFORMATION: Primers

<400> SEQUENCE: 27
cagatgcagc tggtacagtc t                                              21

<210> SEQ ID NO 28
<211> LENGTH: 21
<212> TYPE: DNA
<213> ORGANISM: Artificial Sequence
<220> FEATURE:
<223> OTHER INFORMATION: Primers

<400> SEQUENCE: 28
cagatcacct tgaaggagtc t                                              21

<210> SEQ ID NO 29
<211> LENGTH: 21
<212> TYPE: DNA
<213> ORGANISM: Artificial Sequence
<220> FEATURE:
<223> OTHER INFORMATION: Primers

<400> SEQUENCE: 29
caggtcacct tgaaggagtc t                                              21
```

```
<210> SEQ ID NO 30
<211> LENGTH: 21
<212> TYPE: DNA
<213> ORGANISM: Artificial Sequence
<220> FEATURE:
<223> OTHER INFORMATION: Primers

<400> SEQUENCE: 30
gaagtgcagc tggtggagtc t                                      21

<210> SEQ ID NO 31
<211> LENGTH: 21
<212> TYPE: DNA
<213> ORGANISM: Artificial Sequence
<220> FEATURE:
<223> OTHER INFORMATION: Primers

<400> SEQUENCE: 31
caggtgcagc tggtggagtc t                                      21

<210> SEQ ID NO 32
<211> LENGTH: 21
<212> TYPE: DNA
<213> ORGANISM: Artificial Sequence
<220> FEATURE:
<223> OTHER INFORMATION: Primers

<400> SEQUENCE: 32
gaggtgcagc tgttggagtc t                                      21

<210> SEQ ID NO 33
<211> LENGTH: 21
<212> TYPE: DNA
<213> ORGANISM: Artificial Sequence
<220> FEATURE:
<223> OTHER INFORMATION: Primers

<400> SEQUENCE: 33
caggtgcagc tgcaggagtc g                                      21

<210> SEQ ID NO 34
<211> LENGTH: 21
<212> TYPE: DNA
<213> ORGANISM: Artificial Sequence
<220> FEATURE:
<223> OTHER INFORMATION: Primers

<400> SEQUENCE: 34
cagctgcagc tgcaggagtc g                                      21

<210> SEQ ID NO 35
<211> LENGTH: 21
<212> TYPE: DNA
<213> ORGANISM: Artificial Sequence
<220> FEATURE:
<223> OTHER INFORMATION: Primers

<400> SEQUENCE: 35
caggtgcagc tacagcagtg g                                      21

<210> SEQ ID NO 36
<211> LENGTH: 21
<212> TYPE: DNA
<213> ORGANISM: Artificial Sequence
<220> FEATURE:
<223> OTHER INFORMATION: Primers
```

-continued

<400> SEQUENCE: 36
gaagtgcagc tggtgcagtc t                                              21

<210> SEQ ID NO 37
<211> LENGTH: 21
<212> TYPE: DNA
<213> ORGANISM: Artificial Sequence
<220> FEATURE:
<223> OTHER INFORMATION: Primers

<400> SEQUENCE: 37
caggtacagc tgcagcagtc a                                              21

<210> SEQ ID NO 38
<211> LENGTH: 21
<212> TYPE: DNA
<213> ORGANISM: Artificial Sequence
<220> FEATURE:
<223> OTHER INFORMATION: Primers

<400> SEQUENCE: 38
caggtgcagc tggtgcaatc t                                              21

<210> SEQ ID NO 39
<211> LENGTH: 21
<212> TYPE: DNA
<213> ORGANISM: Artificial Sequence
<220> FEATURE:
<223> OTHER INFORMATION: Primers

<400> SEQUENCE: 39
aagggttggg gcggatgcac t                                              21

<210> SEQ ID NO 40
<211> LENGTH: 21
<212> TYPE: DNA
<213> ORGANISM: Artificial Sequence
<220> FEATURE:
<223> OTHER INFORMATION: Primers

<400> SEQUENCE: 40
cagtctgtgc tgacgcagcc a                                              21

<210> SEQ ID NO 41
<211> LENGTH: 21
<212> TYPE: DNA
<213> ORGANISM: Artificial Sequence
<220> FEATURE:
<223> OTHER INFORMATION: Primers

<400> SEQUENCE: 41
cagtctgtgc tgacgcagcc g                                              21

<210> SEQ ID NO 42
<211> LENGTH: 21
<212> TYPE: DNA
<213> ORGANISM: Artificial Sequence
<220> FEATURE:
<223> OTHER INFORMATION: Primers

<400> SEQUENCE: 42
cagtctgccc tgactcagcc t                                              21

<210> SEQ ID NO 43

```
<211> LENGTH: 21
<212> TYPE: DNA
<213> ORGANISM: Artificial Sequence
<220> FEATURE:
<223> OTHER INFORMATION: Primers

<400> SEQUENCE: 43
tcctatgagc tgacacagcc a                                              21

<210> SEQ ID NO 44
<211> LENGTH: 21
<212> TYPE: DNA
<213> ORGANISM: Artificial Sequence
<220> FEATURE:
<223> OTHER INFORMATION: Primers

<400> SEQUENCE: 44
tcctctgagc tgacacagga c                                              21

<210> SEQ ID NO 45
<211> LENGTH: 21
<212> TYPE: DNA
<213> ORGANISM: Artificial Sequence
<220> FEATURE:
<223> OTHER INFORMATION: Primers

<400> SEQUENCE: 45
tcctatgtgc tgacacagcc a                                              21

<210> SEQ ID NO 46
<211> LENGTH: 21
<212> TYPE: DNA
<213> ORGANISM: Artificial Sequence
<220> FEATURE:
<223> OTHER INFORMATION: Primers

<400> SEQUENCE: 46
tcctatgagc tgacacagct a                                              21

<210> SEQ ID NO 47
<211> LENGTH: 21
<212> TYPE: DNA
<213> ORGANISM: Artificial Sequence
<220> FEATURE:
<223> OTHER INFORMATION: Primers

<400> SEQUENCE: 47
tcctatgagc tgatgcagcc a                                              21

<210> SEQ ID NO 48
<211> LENGTH: 21
<212> TYPE: DNA
<213> ORGANISM: Artificial Sequence
<220> FEATURE:
<223> OTHER INFORMATION: Primers

<400> SEQUENCE: 48
ctgcctgtgc tgactcagcc c                                              21

<210> SEQ ID NO 49
<211> LENGTH: 21
<212> TYPE: DNA
<213> ORGANISM: Artificial Sequence
<220> FEATURE:
<223> OTHER INFORMATION: Primers

<400> SEQUENCE: 49
```
cagcctgtgc tgactcaatc a                                               21

<210> SEQ ID NO 50
<211> LENGTH: 21
<212> TYPE: DNA
<213> ORGANISM: Artificial Sequence
<220> FEATURE:
<223> OTHER INFORMATION: Primers

<400> SEQUENCE: 50
cagcttgtgc tgactcaatc g                                               21

<210> SEQ ID NO 51
<211> LENGTH: 21
<212> TYPE: DNA
<213> ORGANISM: Artificial Sequence
<220> FEATURE:
<223> OTHER INFORMATION: Primers

<400> SEQUENCE: 51
cagcctgtgc tgactcagcc a                                               21

<210> SEQ ID NO 52
<211> LENGTH: 21
<212> TYPE: DNA
<213> ORGANISM: Artificial Sequence
<220> FEATURE:
<223> OTHER INFORMATION: Primers

<400> SEQUENCE: 52
caggctgtgc tgactcagcc g                                               21

<210> SEQ ID NO 53
<211> LENGTH: 21
<212> TYPE: DNA
<213> ORGANISM: Artificial Sequence
<220> FEATURE:
<223> OTHER INFORMATION: Primers

<400> SEQUENCE: 53
aattttatgc tgactcagcc c                                               21

<210> SEQ ID NO 54
<211> LENGTH: 21
<212> TYPE: DNA
<213> ORGANISM: Artificial Sequence
<220> FEATURE:
<223> OTHER INFORMATION: Primers

<400> SEQUENCE: 54
cagactgtgg tgactcagga g                                               21

<210> SEQ ID NO 55
<211> LENGTH: 21
<212> TYPE: DNA
<213> ORGANISM: Artificial Sequence
<220> FEATURE:
<223> OTHER INFORMATION: Primers

<400> SEQUENCE: 55
caggctgtgg tgactcagga g                                               21

<210> SEQ ID NO 56
<211> LENGTH: 21
<212> TYPE: DNA

```
<213> ORGANISM: Artificial Sequence
<220> FEATURE:
<223> OTHER INFORMATION: Primers

<400> SEQUENCE: 56
cagactgtgg tgacccagga g                                              21

<210> SEQ ID NO 57
<211> LENGTH: 21
<212> TYPE: DNA
<213> ORGANISM: Artificial Sequence
<220> FEATURE:
<223> OTHER INFORMATION: Primers

<400> SEQUENCE: 57
cagcctgtgc tgactcagcc a                                              21

<210> SEQ ID NO 58
<211> LENGTH: 21
<212> TYPE: DNA
<213> ORGANISM: Artificial Sequence
<220> FEATURE:
<223> OTHER INFORMATION: Primers

<400> SEQUENCE: 58
caggcagggc tgactcagcc a                                              21

<210> SEQ ID NO 59
<211> LENGTH: 21
<212> TYPE: DNA
<213> ORGANISM: Artificial Sequence
<220> FEATURE:
<223> OTHER INFORMATION: Primers

<400> SEQUENCE: 59
gacatccaga tgacccagtc t                                              21

<210> SEQ ID NO 60
<211> LENGTH: 21
<212> TYPE: DNA
<213> ORGANISM: Artificial Sequence
<220> FEATURE:
<223> OTHER INFORMATION: Primers

<400> SEQUENCE: 60
aacatccaga tgacccagtc t                                              21

<210> SEQ ID NO 61
<211> LENGTH: 21
<212> TYPE: DNA
<213> ORGANISM: Artificial Sequence
<220> FEATURE:
<223> OTHER INFORMATION: Primers

<400> SEQUENCE: 61
gccatccagt tgacccagtc t                                              21

<210> SEQ ID NO 62
<211> LENGTH: 20
<212> TYPE: DNA
<213> ORGANISM: Artificial Sequence
<220> FEATURE:
<223> OTHER INFORMATION: Primers

<400> SEQUENCE: 62
acatccagtt gacccagtct                                                20
```

<210> SEQ ID NO 63
<211> LENGTH: 21
<212> TYPE: DNA
<213> ORGANISM: Artificial Sequence
<220> FEATURE:
<223> OTHER INFORMATION: Primers

<400> SEQUENCE: 63
gccatccgga tgacccagtc t                                     21

<210> SEQ ID NO 64
<211> LENGTH: 21
<212> TYPE: DNA
<213> ORGANISM: Artificial Sequence
<220> FEATURE:
<223> OTHER INFORMATION: Primers

<400> SEQUENCE: 64
gtcatctgga tgacccagtc t                                     21

<210> SEQ ID NO 65
<211> LENGTH: 21
<212> TYPE: DNA
<213> ORGANISM: Artificial Sequence
<220> FEATURE:
<223> OTHER INFORMATION: Primers

<400> SEQUENCE: 65
gccatccaga tgacccagtc t                                     21

<210> SEQ ID NO 66
<211> LENGTH: 21
<212> TYPE: DNA
<213> ORGANISM: Artificial Sequence
<220> FEATURE:
<223> OTHER INFORMATION: Primers

<400> SEQUENCE: 66
gatattgtga tgacccagac t                                     21

<210> SEQ ID NO 67
<211> LENGTH: 21
<212> TYPE: DNA
<213> ORGANISM: Artificial Sequence
<220> FEATURE:
<223> OTHER INFORMATION: Primers

<400> SEQUENCE: 67
gatgttgtga tgactcagtc t                                     21

<210> SEQ ID NO 68
<211> LENGTH: 21
<212> TYPE: DNA
<213> ORGANISM: Artificial Sequence
<220> FEATURE:
<223> OTHER INFORMATION: Primers

<400> SEQUENCE: 68
gatattgtga tgactcagtc t                                     21

<210> SEQ ID NO 69
<211> LENGTH: 20
<212> TYPE: DNA
<213> ORGANISM: Artificial Sequence
<220> FEATURE:

-continued

```
<223> OTHER INFORMATION: Primers

<400> SEQUENCE: 69
aaattgtgtt gacgcagtct                                                    20

<210> SEQ ID NO 70
<211> LENGTH: 21
<212> TYPE: DNA
<213> ORGANISM: Artificial Sequence
<220> FEATURE:
<223> OTHER INFORMATION: Primers

<400> SEQUENCE: 70
gaaattgtga tgacgcagtc t                                                  21

<210> SEQ ID NO 71
<211> LENGTH: 21
<212> TYPE: DNA
<213> ORGANISM: Artificial Sequence
<220> FEATURE:
<223> OTHER INFORMATION: Primers

<400> SEQUENCE: 71
gaaattgtaa tgacgcagtc t                                                  21

<210> SEQ ID NO 72
<211> LENGTH: 21
<212> TYPE: DNA
<213> ORGANISM: Artificial Sequence
<220> FEATURE:
<223> OTHER INFORMATION: Primers

<400> SEQUENCE: 72
gacatcgtga tgacccagtc t                                                  21

<210> SEQ ID NO 73
<211> LENGTH: 21
<212> TYPE: DNA
<213> ORGANISM: Artificial Sequence
<220> FEATURE:
<223> OTHER INFORMATION: Primers

<400> SEQUENCE: 73
gaaacgacac tcacgcagtc t                                                  21

<210> SEQ ID NO 74
<211> LENGTH: 21
<212> TYPE: DNA
<213> ORGANISM: Artificial Sequence
<220> FEATURE:
<223> OTHER INFORMATION: Primers

<400> SEQUENCE: 74
gaaattgtgc tgactcagtc t                                                  21

<210> SEQ ID NO 75
<211> LENGTH: 21
<212> TYPE: DNA
<213> ORGANISM: Artificial Sequence
<220> FEATURE:
<223> OTHER INFORMATION: Primers

<400> SEQUENCE: 75
gatgttgtga tgacacagtc t                                                  21
```

```
<210> SEQ ID NO 76
<211> LENGTH: 21
<212> TYPE: DNA
<213> ORGANISM: Artificial Sequence
<220> FEATURE:
<223> OTHER INFORMATION: Primers

<400> SEQUENCE: 76
ggacggcggg aacagagtga c                                          21

<210> SEQ ID NO 77
<211> LENGTH: 21
<212> TYPE: DNA
<213> ORGANISM: Artificial Sequence
<220> FEATURE:
<223> OTHER INFORMATION: Primers

<400> SEQUENCE: 77
gacagatggt gcagccacag t                                          21

<210> SEQ ID NO 78
<211> LENGTH: 36
<212> TYPE: DNA
<213> ORGANISM: Artificial Sequence
<220> FEATURE:
<223> OTHER INFORMATION: Primers

<400> SEQUENCE: 78
tggacgccca tggcgcaggt gcagctggtg cagtct                          36

<210> SEQ ID NO 79
<211> LENGTH: 36
<212> TYPE: DNA
<213> ORGANISM: Artificial Sequence
<220> FEATURE:
<223> OTHER INFORMATION: Primers

<400> SEQUENCE: 79
tggacgccca tggcgcaggt ccagcttgtg cagtct                          36

<210> SEQ ID NO 80
<211> LENGTH: 36
<212> TYPE: DNA
<213> ORGANISM: Artificial Sequence
<220> FEATURE:
<223> OTHER INFORMATION: Primers

<400> SEQUENCE: 80
tggacgccca tggcgcaggt ccagctggta cagtct                          36

<210> SEQ ID NO 81
<211> LENGTH: 36
<212> TYPE: DNA
<213> ORGANISM: Artificial Sequence
<220> FEATURE:
<223> OTHER INFORMATION: Primers

<400> SEQUENCE: 81
tggacgccca tggcggaggt ccagctggta cagtct                          36

<210> SEQ ID NO 82
<211> LENGTH: 36
<212> TYPE: DNA
<213> ORGANISM: Artificial Sequence
<220> FEATURE:
<223> OTHER INFORMATION: Primers
```

```
<400> SEQUENCE: 82
tggacgccca tggcgcagat gcagctggta cagtct                                  36

<210> SEQ ID NO 83
<211> LENGTH: 36
<212> TYPE: DNA
<213> ORGANISM: Artificial Sequence
<220> FEATURE:
<223> OTHER INFORMATION: Primers

<400> SEQUENCE: 83
tggacgccca tggcgcagat caccttgaag gagtct                                  36

<210> SEQ ID NO 84
<211> LENGTH: 36
<212> TYPE: DNA
<213> ORGANISM: Artificial Sequence
<220> FEATURE:
<223> OTHER INFORMATION: Primers

<400> SEQUENCE: 84
tggacgccca tggcgcaggt caccttgaag gagtct                                  36

<210> SEQ ID NO 85
<211> LENGTH: 36
<212> TYPE: DNA
<213> ORGANISM: Artificial Sequence
<220> FEATURE:
<223> OTHER INFORMATION: Primers

<400> SEQUENCE: 85
tggacgccca tggcggaagt gcagctggtg gagtct                                  36

<210> SEQ ID NO 86
<211> LENGTH: 36
<212> TYPE: DNA
<213> ORGANISM: Artificial Sequence
<220> FEATURE:
<223> OTHER INFORMATION: Primers

<400> SEQUENCE: 86
tggacgccca tggcgcaggt gcagctggtg gagtct                                  36

<210> SEQ ID NO 87
<211> LENGTH: 36
<212> TYPE: DNA
<213> ORGANISM: Artificial Sequence
<220> FEATURE:
<223> OTHER INFORMATION: Primers

<400> SEQUENCE: 87
tggacgccca tggcggaggt gcagctgttg gagtct                                  36

<210> SEQ ID NO 88
<211> LENGTH: 36
<212> TYPE: DNA
<213> ORGANISM: Artificial Sequence
<220> FEATURE:
<223> OTHER INFORMATION: Primers

<400> SEQUENCE: 88
tggacgccca tggcgcaggt gcagctgcag gagtcg                                  36

<210> SEQ ID NO 89
<211> LENGTH: 36
```

```
<212> TYPE: DNA
<213> ORGANISM: Artificial Sequence
<220> FEATURE:
<223> OTHER INFORMATION: Primers

<400> SEQUENCE: 89
tggacgccca tggcgcagct gcagctgcag gagtcg                              36

<210> SEQ ID NO 90
<211> LENGTH: 36
<212> TYPE: DNA
<213> ORGANISM: Artificial Sequence
<220> FEATURE:
<223> OTHER INFORMATION: Primers

<400> SEQUENCE: 90
tggacgccca tggcgcaggt gcagctacag cagtgg                              36

<210> SEQ ID NO 91
<211> LENGTH: 36
<212> TYPE: DNA
<213> ORGANISM: Artificial Sequence
<220> FEATURE:
<223> OTHER INFORMATION: Primers

<400> SEQUENCE: 91
tggacgccca tggcggaagt gcagctggtg cagtct                              36

<210> SEQ ID NO 92
<211> LENGTH: 36
<212> TYPE: DNA
<213> ORGANISM: Artificial Sequence
<220> FEATURE:
<223> OTHER INFORMATION: Primers

<400> SEQUENCE: 92
tggacgccca tggcgcaggt acagctgcag cagtca                              36

<210> SEQ ID NO 93
<211> LENGTH: 36
<212> TYPE: DNA
<213> ORGANISM: Artificial Sequence
<220> FEATURE:
<223> OTHER INFORMATION: Primers

<400> SEQUENCE: 93
tggacgccca tggcgcaggt gcagctggtg caatct                              36

<210> SEQ ID NO 94
<211> LENGTH: 33
<212> TYPE: DNA
<213> ORGANISM: Artificial Sequence
<220> FEATURE:
<223> OTHER INFORMATION: Primers

<400> SEQUENCE: 94
tgggaaaagc ttaagggttg gggcggatgc act                                 33

<210> SEQ ID NO 95
<211> LENGTH: 36
<212> TYPE: DNA
<213> ORGANISM: Artificial Sequence
<220> FEATURE:
<223> OTHER INFORMATION: Primers

<400> SEQUENCE: 95
```
cctacagaac gcgtacagtc tgtgctgacg cagcca    36

<210> SEQ ID NO 96
<211> LENGTH: 36
<212> TYPE: DNA
<213> ORGANISM: Artificial Sequence
<220> FEATURE:
<223> OTHER INFORMATION: Primers

<400> SEQUENCE: 96
cctacagaac gcgtacagtc tgtgctgacg cagccg    36

<210> SEQ ID NO 97
<211> LENGTH: 36
<212> TYPE: DNA
<213> ORGANISM: Artificial Sequence
<220> FEATURE:
<223> OTHER INFORMATION: Primers

<400> SEQUENCE: 97
cctacagaac gcgtacagtc tgccctgact cagcct    36

<210> SEQ ID NO 98
<211> LENGTH: 36
<212> TYPE: DNA
<213> ORGANISM: Artificial Sequence
<220> FEATURE:
<223> OTHER INFORMATION: Primers

<400> SEQUENCE: 98
cctacagaac gcgtatccta tgagctgaca cagcca    36

<210> SEQ ID NO 99
<211> LENGTH: 36
<212> TYPE: DNA
<213> ORGANISM: Artificial Sequence
<220> FEATURE:
<223> OTHER INFORMATION: Primers

<400> SEQUENCE: 99
cctacagaac gcgtatcctc tgagctgaca caggac    36

<210> SEQ ID NO 100
<211> LENGTH: 36
<212> TYPE: DNA
<213> ORGANISM: Artificial Sequence
<220> FEATURE:
<223> OTHER INFORMATION: Primers

<400> SEQUENCE: 100
cctacagaac gcgtatccta tgtgctgaca cagcca    36

<210> SEQ ID NO 101
<211> LENGTH: 36
<212> TYPE: DNA
<213> ORGANISM: Artificial Sequence
<220> FEATURE:
<223> OTHER INFORMATION: Primers

<400> SEQUENCE: 101
cctacagaac gcgtatccta tgagctgaca cagcta    36

<210> SEQ ID NO 102
<211> LENGTH: 36
<212> TYPE: DNA
<213> ORGANISM: Artificial Sequence
<220> FEATURE:
<223> OTHER INFORMATION: Primers

<400> SEQUENCE: 102
cctacagaac gcgtatccta tgagctgatg cagcca                              36

<210> SEQ ID NO 103
<211> LENGTH: 36
<212> TYPE: DNA
<213> ORGANISM: Artificial Sequence
<220> FEATURE:
<223> OTHER INFORMATION: Primers

<400> SEQUENCE: 103
cctacagaac gcgtactgcc tgtgctgact cagccc                              36

<210> SEQ ID NO 104
<211> LENGTH: 36
<212> TYPE: DNA
<213> ORGANISM: Artificial Sequence
<220> FEATURE:
<223> OTHER INFORMATION: Primers

<400> SEQUENCE: 104
cctacagaac gcgtacagcc tgtgctgact caatca                              36

<210> SEQ ID NO 105
<211> LENGTH: 36
<212> TYPE: DNA
<213> ORGANISM: Artificial Sequence
<220> FEATURE:
<223> OTHER INFORMATION: Primers

<400> SEQUENCE: 105
cctacagaac gcgtacagct tgtgctgact caatcg                              36

<210> SEQ ID NO 106
<211> LENGTH: 36
<212> TYPE: DNA
<213> ORGANISM: Artificial Sequence
<220> FEATURE:
<223> OTHER INFORMATION: Primers

<400> SEQUENCE: 106
cctacagaac gcgtacagcc tgtgctgact cagcca                              36

<210> SEQ ID NO 107
<211> LENGTH: 36
<212> TYPE: DNA
<213> ORGANISM: Artificial Sequence
<220> FEATURE:
<223> OTHER INFORMATION: Primers

<400> SEQUENCE: 107
cctacagaac gcgtacaggc tgtgctgact cagccg                              36

<210> SEQ ID NO 108
<211> LENGTH: 36
<212> TYPE: DNA
<213> ORGANISM: Artificial Sequence
<220> FEATURE:
<223> OTHER INFORMATION: Primers

<400> SEQUENCE: 108
cctacagaac gcgtaaattt tatgctgact cagccc                              36

<210> SEQ ID NO 109
<211> LENGTH: 36
<212> TYPE: DNA
<213> ORGANISM: Artificial Sequence
<220> FEATURE:
<223> OTHER INFORMATION: Primers

<400> SEQUENCE: 109
cctacagaac gcgtacagac tgtggtgact caggag                           36

<210> SEQ ID NO 110
<211> LENGTH: 36
<212> TYPE: DNA
<213> ORGANISM: Artificial Sequence
<220> FEATURE:
<223> OTHER INFORMATION: Primers

<400> SEQUENCE: 110
cctacagaac gcgtacaggc tgtggtgact caggag                           36

<210> SEQ ID NO 111
<211> LENGTH: 36
<212> TYPE: DNA
<213> ORGANISM: Artificial Sequence
<220> FEATURE:
<223> OTHER INFORMATION: Primers

<400> SEQUENCE: 111
cctacagaac gcgtacagac tgtggtgacc caggag                           36

<210> SEQ ID NO 112
<211> LENGTH: 36
<212> TYPE: DNA
<213> ORGANISM: Artificial Sequence
<220> FEATURE:
<223> OTHER INFORMATION: Primers

<400> SEQUENCE: 112
cctacagaac gcgtacagcc tgtgctgact cagcca                           36

<210> SEQ ID NO 113
<211> LENGTH: 36
<212> TYPE: DNA
<213> ORGANISM: Artificial Sequence
<220> FEATURE:
<223> OTHER INFORMATION: Primers

<400> SEQUENCE: 113
cctacagaac gcgtacaggc agggctgact cagcca                           36

<210> SEQ ID NO 114
<211> LENGTH: 36
<212> TYPE: DNA
<213> ORGANISM: Artificial Sequence
<220> FEATURE:
<223> OTHER INFORMATION: Primers

<400> SEQUENCE: 114
cctacagaac gcgtagacat ccagatgacc cagtct                           36

<210> SEQ ID NO 115
<211> LENGTH: 36
<212> TYPE: DNA
<213> ORGANISM: Artificial Sequence
<220> FEATURE:
<223> OTHER INFORMATION: Primers

<400> SEQUENCE: 115
cctacagaac gcgtaaacat ccagatgacc cagtct                36

<210> SEQ ID NO 116
<211> LENGTH: 36
<212> TYPE: DNA
<213> ORGANISM: Artificial Sequence
<220> FEATURE:
<223> OTHER INFORMATION: Primers

<400> SEQUENCE: 116
cctacagaac gcgtagccat ccagttgacc cagtct                36

<210> SEQ ID NO 117
<211> LENGTH: 36
<212> TYPE: DNA
<213> ORGANISM: Artificial Sequence
<220> FEATURE:
<223> OTHER INFORMATION: Primers

<400> SEQUENCE: 117
cctacagaac gcgtagacat ccagttgacc cagtct                36

<210> SEQ ID NO 118
<211> LENGTH: 36
<212> TYPE: DNA
<213> ORGANISM: Artificial Sequence
<220> FEATURE:
<223> OTHER INFORMATION: Primers

<400> SEQUENCE: 118
cctacagaac gcgtagccat ccggatgacc cagtct                36

<210> SEQ ID NO 119
<211> LENGTH: 36
<212> TYPE: DNA
<213> ORGANISM: Artificial Sequence
<220> FEATURE:
<223> OTHER INFORMATION: Primers

<400> SEQUENCE: 119
cctacagaac gcgtagtcat ctggatgacc cagtct                36

<210> SEQ ID NO 120
<211> LENGTH: 36
<212> TYPE: DNA
<213> ORGANISM: Artificial Sequence
<220> FEATURE:
<223> OTHER INFORMATION: Primers

<400> SEQUENCE: 120
cctacagaac gcgtagccat ccagatgacc cagtct                36

<210> SEQ ID NO 121
<211> LENGTH: 36
<212> TYPE: DNA
<213> ORGANISM: Artificial Sequence
<220> FEATURE:
<223> OTHER INFORMATION: Primers

<400> SEQUENCE: 121
cctacagaac gcgtagatat tgtgatgacc cagact                36

<210> SEQ ID NO 122

```
<211> LENGTH: 36
<212> TYPE: DNA
<213> ORGANISM: Artificial Sequence
<220> FEATURE:
<223> OTHER INFORMATION: Primers

<400> SEQUENCE: 122
cctacagaac gcgtagatgt tgtgatgact cagtct                               36

<210> SEQ ID NO 123
<211> LENGTH: 36
<212> TYPE: DNA
<213> ORGANISM: Artificial Sequence
<220> FEATURE:
<223> OTHER INFORMATION: Primers

<400> SEQUENCE: 123
cctacagaac gcgtagatat tgtgatgact cagtct                               36

<210> SEQ ID NO 124
<211> LENGTH: 36
<212> TYPE: DNA
<213> ORGANISM: Artificial Sequence
<220> FEATURE:
<223> OTHER INFORMATION: Primers

<400> SEQUENCE: 124
cctacagaac gcgtagaaat tgtgttgacg cagtct                               36

<210> SEQ ID NO 125
<211> LENGTH: 36
<212> TYPE: DNA
<213> ORGANISM: Artificial Sequence
<220> FEATURE:
<223> OTHER INFORMATION: Primers

<400> SEQUENCE: 125
cctacagaac gcgtagaaat tgtgatgacg cagtct                               36

<210> SEQ ID NO 126
<211> LENGTH: 36
<212> TYPE: DNA
<213> ORGANISM: Artificial Sequence
<220> FEATURE:
<223> OTHER INFORMATION: Primers

<400> SEQUENCE: 126
cctacagaac gcgtagaaat tgtaatgacg cagtct                               36

<210> SEQ ID NO 127
<211> LENGTH: 36
<212> TYPE: DNA
<213> ORGANISM: Artificial Sequence
<220> FEATURE:
<223> OTHER INFORMATION: Primers

<400> SEQUENCE: 127
cctacagaac gcgtagacat cgtgatgacc cagtct                               36

<210> SEQ ID NO 128
<211> LENGTH: 36
<212> TYPE: DNA
<213> ORGANISM: Artificial Sequence
<220> FEATURE:
<223> OTHER INFORMATION: Primers

<400> SEQUENCE: 128
```

```
cctacagaac gcgtagaaac gacactcacg cagtct                                   36

<210> SEQ ID NO 129
<211> LENGTH: 36
<212> TYPE: DNA
<213> ORGANISM: Artificial Sequence
<220> FEATURE:
<223> OTHER INFORMATION: Primers

<400> SEQUENCE: 129
cctacagaac gcgtagaaat tgtgctgact cagtct                                   36

<210> SEQ ID NO 130
<211> LENGTH: 36
<212> TYPE: DNA
<213> ORGANISM: Artificial Sequence
<220> FEATURE:
<223> OTHER INFORMATION: Primers

<400> SEQUENCE: 130
cctacagaac gcgtagatgt tgtgatgaca cagtct                                   36

<210> SEQ ID NO 131
<211> LENGTH: 39
<212> TYPE: DNA
<213> ORGANISM: Artificial Sequence
<220> FEATURE:
<223> OTHER INFORMATION: Primers

<400> SEQUENCE: 131
gggcggcagg gcggccgcgg acggcgggaa cagagtgac                                39

<210> SEQ ID NO 132
<211> LENGTH: 39
<212> TYPE: DNA
<213> ORGANISM: Artificial Sequence
<220> FEATURE:
<223> OTHER INFORMATION: Primers

<400> SEQUENCE: 132
gggcggcagg gcggccgcga cagatggtgc agccacagt                                39

<210> SEQ ID NO 133
<211> LENGTH: 4923
<212> TYPE: DNA
<213> ORGANISM: Artificial Sequence
<220> FEATURE:
<223> OTHER INFORMATION: Plasmid

<400> SEQUENCE: 133
actcgagagc gggcagtgag cgcaacgcaa ttaatgtgag ttagctcact cattaggcac         60
cccaggcttt acactttatg cttccggctc gtatgttgtg tggaattgtg agcggataac        120
aatttcacac agaattcatt aaagaggaga attaaccat gaaataccta ttgcctacgg         180
cagccgctgg cttgctgctg ctggcagctc agccggccat ggcgcaggta cagctgcagg        240
agtctggggg aggcgtggtc cagcctggga ggtccctgag actctcctgt gcagcctctg        300
gattctcctt cagtaattat ggcatacact gggtccgcca ggctccaggc aaggggctgg        360
agtgggtggc acttatatca tatgatggaa ataagaaatt ctatgcagac tccgtgaagg        420
gccgattcgc catctccaga gacacttcta agaatacggt ggatctgcaa atgaccagcc        480
tgagacctga ggacacgtct tcagcgctga gctcgaagac tggtcaccgt ctcctcagcc        540
```

```
tccaccaagg gcccaaagct tgaagaaggt gaattttcag aagcacgcgt atcctatgaa    600
ctgactcagc caccctcggt gtcagtggcc ccaggacaga cggccatgat tacctgtggg    660
ggaaacaaca ttggaagtac aaccgtgcac tggtatcagc agaagccagg ccaggcccct    720
gtgctggtcg tctatgatga taacgagcga ccctcaggga tccctgagcg attctctggc    780
tccaactctg ggagcacggc caccctgacc atcaacaggg tcgaagccgg ggatgaggcc    840
gactattatt gtcaagtgtg ggatagtggt agtgatcatg tggtattcgg cggagggacg    900
aagctgaccg tcctaggtca gcccaaggct gccccctcgg tcactctgtt cccgccctcc    960
tctgcggccg ctggatccca tcaccatcac catcactagg aacaaaagct gatctcagaa   1020
gaagacctaa acggatccaa agatatcaga gctgaaactg ttgaaagttg tttagcaaaa   1080
tcccatacag aaaattcatt tactaacgtc tggaaagacg acaaaacttt agatcgttac   1140
gctaactatg agggctgtct gtggaatgct acaggcgttg tagtttgtac tggtgacgaa   1200
actcagtgtt acggtacatg ggttcctatt gggcttgcta tccctgaaaa tgagggtggt   1260
ggctctgagg gtggcggttc tgagggtggc ggttctgagg gtggcggtac taaacctcct   1320
gagtacggtg atacacctat tccgggctat acttatatca accctctcga cggcacttat   1380
ccgcctggta ctgagcaaaa ccccgctaat cctaatcctt ctcttgagga gtctcagcct   1440
cttaatactt tcatgtttca gaataatagg ttccgaaata ggcaggggc attaactgtt   1500
tatacgggca ctgttactca aggcactgac cccgttaaaa cttattacca gtacactcct   1560
gtatcatcaa agccatgta tgacgcttac tggaacggta aattcagaga ctgcgctttc   1620
cattctggct ttaatgagga tttatttgtt tgtgaatatc aaggccaatc gtctgacctg   1680
cctcaacctc ctgtcaatgc tggcggcggc tctggtggtg gttctggtgg cggctctgag   1740
ggtggtggct ctgagggtgg cggttctgag gtggcggct ctgagggagg cggttccggt   1800
ggtggctctg gttccggtga ttttgattat gaaaagatgg caaacgctaa taagggggct   1860
atgaccgaaa atgccgatga aaacgcgcta cagtctgacg ctaaaggcaa acttgattct   1920
gtcgctactg attacggtgc tgctatcgat ggtttcattg gtgacgtttc cggccttgct   1980
aatggtaatg gtgctactgg tgattttgct ggctctaatt cccaaatggc tcaagtcggt   2040
gacggtgata attcaccttt aatgaataat ttccgtcaat atttaccttc cctccctcaa   2100
tcggttgaat gtcgcccttt tgtctttggc gctggtaaac catatgaatt ttctattgat   2160
tgtgacaaaa taaacttatt ccgtggtgtc tttgcgtttc ttttatatgt tgccaccttt   2220
atgtatgtat tttctacgtt tgctaacata ctgcgtaata aggagtctta atgatctaga   2280
ggcctgtgct aatgatcagc tagcttgagg catcaataaa acgaaaggct cagtcgaaag   2340
actgggcctt tcgttttatc tgttgtttgt cggttaacgt cgacctggcg taatagcgaa   2400
gaggcccgca ccgatcgccc ttcccaacag ttgcgcagcc tgaatggcga atgggacgcg   2460
ccctgtagcg cgcattaag cgcggcgggt gtggtggtta cgcgcagcgt gaccgctaca   2520
cttgccagcg ccctagcgcc cgctcctttc gctttcttcc cttcctttct cgccacgttc   2580
gccggctttc cccgtcaagc tctaaatcgg gggctccctt tagggttccg atttagtgct   2640
ttacggcacc tcgaccccaa aaaacttgat tagggtgatg gttcacgtag tgggccatcg   2700
ccctgataga cggttttcg ccctttgacg ttggagtcca cgttctttaa tagtggactc   2760
ttgttccaaa ctggaacaac actcaaccct atctcggtct attcttttga tttataaggg   2820
attttgccga tttcggccta ttggttaaaa aatgagctga tttaacaaaa atttaacgcg   2880
aattttaaca aaatattaac gcttacaatt taggtggcac ttttcgggga aatgtgcgcg   2940
```

```
gaacccctat tgtttatttt ttctaaatac attcaaatat gtatccgctc atgagacaat    3000
aaccctgata aatgcttcaa taatattgaa aaggaagag tatgagtatt caacatttcc    3060
gtgtcgccct tattccctt tttgcggcat tttgccttcc tgttttgct cacccagaaa    3120 cgctggtgaa agtaaaagat gctgaagatc agttgggtgc acgagtgggt tacatcgaac    3180
tggatctcaa cagcggtaag atccttgaga gttttcgccc cgaagaacgt tttccaatga    3240
tgagcacttt taaagttctg ctatgtggcg cggtattatc ccgtattgac gccgggcaag    3300
agcaactcgg tcgccgcata cactattctc agaatgactt ggttgagtac tcaccagtca    3360
cagaaaagca tcttacggat ggcatgacag taagagaatt atgcagtgct gccataacca    3420
tgagtgataa cactgcggcc aacttacttc tgacaacgat cggaggaccg aaggagctaa    3480
ccgctttttt gcacaacatg gggatcatg taactcgcct tgatcgttgg gaaccggagc    3540
tgaatgaagc cataccaaac gacgagcgtg acaccacgat gcctgtagca atggcaacaa    3600
cgttgcgcaa actattaact ggcgaactac ttactctagc ttcccggcaa caattaatag    3660
actggatgga ggcggataaa gttgcaggac cacttctgcg ctcggccctt ccggctggct    3720
ggtttattgc tgataaatct ggagccggtg agcgtgggtc tcgcggtatc attgcagcac    3780
tggggccaga tggtaagccc tcccgtatcg tagttatcta cacgacgggg agtcaggcaa    3840
ctatggatga acgaaataga cagatcgctg agataggtgc ctcactgatt aagcattggt    3900
aactgtcaga ccaagtttac tcatatatac tttagattga tttaaaactt catttttaat    3960
ttaaaaggat ctaggtgaag atcctttttg ataatctcat gaccaaaatc ccttaacgtg    4020
agttttcgtt ccactgagcg tcagaccccg tagaaaagat caaaggatct tcttgagatc    4080
ctttttttct gcgcgtaatc tgctgcttgc aaacaaaaaa accaccgcta ccagcggtgg    4140
tttgtttgcc ggatcaagag ctaccaactc ttttccgaa ggtaactggc ttcagcagag    4200
cgcagatacc aaatactgtc cttctagtgt agccgtagtt aggccaccac ttcaagaact    4260
ctgtagcacc gcctacatac ctcgctctgc taatcctgtt accagtggct gctgccagtg    4320
gcgataagtc gtgtcttacc gggttggact caagacgata gttaccggat aaggcgcagc    4380
ggtcgggctg aacggggggt tcgtgcacac agcccagctt ggagcgaacg acctacaccg    4440
aactgagata cctacagcgt gagctatgag aaagcgccac gcttcccgaa gggagaaagg    4500
cggacaggta tccggtaagc ggcagggtcg gaacaggaga gcgcacgagg gagcttccag    4560
ggggaaacgc ctggtatctt tatagtcctg tcgggtttcg ccacctctga cttgagcgtc    4620
gatttttgtg atgctcgtca ggggggcgga gcctatggaa aaacgccagc aacgcggcct    4680
ttttacggtt cctggccttt tgctggcctt ttgctcacat gttctttcct gcgttatccc    4740
ctgattctgt ggataaccgt attaccgcct ttgagtgagc tgataccgct cgccgcagcc    4800
gaacgaccga gcgcagcgag tcagtgagcg aggaagcgga agagcgccca atacgcaaac    4860
cgcctctccc cgcgcgttgg ccgattcatt aatgcaggta tcacgaggcc ctttcgtctt    4920
cac                                                                 4923
```

<210> SEQ ID NO 134
<211> LENGTH: 4925
<212> TYPE: DNA
<213> ORGANISM: Artificial Sequence
<220> FEATURE:
<223> OTHER INFORMATION: Plasmid

<400> SEQUENCE: 134

-continued

```
ctcgagagcg ggcagtgagc gcaacgcaat taatgtgagt tagctcactc attaggcacc      60
ccaggcttta cactttatgc ttccggctcg tatgttgtgt ggaattgtga gcggataaca     120
atttcacaca gaattcatta aagaggagaa attaaccatg aaatacctat tgcctacggc     180
agccgctggc ttgctgctgc tggcagctca gccggccatg gcgcaggtgc agctgcagga     240
gtctggggga ggcttggtac agcctggggg gtccctgaga ctctcctgtg cagcctctgg     300
attcatgttt agcaggtatg ccatgagctg ggtccgccag gctccaggga aggggccaga     360
gtgggtctca ggtattagtg gtagtggtgg tagtacatac tacgcagact ccgtgaaggg     420
ccggttcacc gtctccagag acaattccaa gaacacgctg tatctgcaaa tgaacagcct     480
gagagccgag gacacgtctt cagcgctgag ctcgaagact ggtcaccgtc tcctcaggga     540
gtgcatccgc cccaaagctt gaagaaggtg aattttcaga agcacgcgta tctgaactga     600
ctcaggaccc tgctgtgtct gtggccttgg gacagacagt caggatcaca tgccaaggag     660
acagcctcag aaacttttat gcaagctggt accagcagaa gccaggacag gcccctactc     720
ttgtcatcta tggtttaagt aaaaggccct cagggatccc agaccgattc tctgcctcca     780
gctcaggaaa cacagcttcc ttgaccatca ctggggctca ggcggaagat gaggctgact     840
attactgtaa ctcccgggac agaagtggta atcatgtaaa tgtgctattc ggcggaggga     900
ccaagctgac cgtcctacgt cagcccaagg ctgccccctc ggtcactctg ttcccgccct     960
cttctgcggc cgctggatcc catcaccatc accatcacta ggaacaaaag ctgatctcag    1020
aagaagacct aaacgatccc aaagatatca gagctgaaac tgttgaaagt tgtttagcaa    1080
aatcccatac agaaaattca tttactaacg tctggaaaga cgacaaaact ttagatcgtt    1140
acgctaacta tgagggctgt ctgtggaatg ctacaggcgt tgtagtttgt actggtgacg    1200
aaactcagtg ttacggtaca tgggttccta ttgggcttgc tatccctgaa aatgagggtg    1260
gtggctctga gggtggcggt tctgaggtgg cggttctgag ggtggcggt actaaacctc    1320
ctgagtacgg tgatacacct attccgggct atacttatat caaccctctc gacggcactt    1380
atccgcctgg tactgagcaa aaccccgcta atcctaatcc ttctcttgag gagtctcagc    1440
ctcttaatac tttcatgttt cagaataata ggttccgaaa taggcagggg gcattaactg    1500
tttatacggg cactgttact caaggcactg accccgttaa aacttattac cagtacactc    1560
ctgtatcatc aaaagccatg tatgacgctt actggaacgg taaattcaga gactgcgctt    1620
tccattctgg ctttaatgag gatttatttg tttgtgaata tcaaggccaa tcgtctgacc    1680
tgcctcaacc tcctgtcaat gctggcggcg gctctggtgg tggttctggt ggcggctctg    1740
agggtggtgg ctctgagggt ggcggttctg agggtggcgg ctctgaggga ggcggttccg    1800
gtggtggctc tggttccggt gattttgatt atgaaaagat ggcaaacgct aataagggg    1860
ctatgaccga aaatgccgat gaaaacgcgc tacagtctga cgctaaaggc aaacttgatt    1920
ctgtcgctac tgattacggt gctgctatcg atggtttcat tggtgacgtt tccggccttg    1980
ctaatggtaa tggtgctact ggtgattttg ctggctctaa ttcccaaatg gctcaagtcg    2040
gtgacggtga taattcacct ttaatgaata atttccgtca atatttacct tccctccctc    2100
aatcggttga atgtcgccct tttgtctttg cgctggtaa accatatgaa ttttctattg    2160
attgtgacaa aataaactta ttccgtggtg tctttgcgtt tcttttatat gttgccacct    2220
ttatgtatgt attttctacg tttgctaaca tactgcgtaa taaggagtct aatgatcta    2280
gaggcctgtg ctaatgatca gctagcttga ggcatcaata aaacgaaagg ctcagtcgaa    2340
agactgggcc tttcgtttta tctgttgttt gtcggttaac gtcgacctgg cgtaatagcg    2400
```

```
aagaggcccg caccgatcgc ccttcccaac agttgcgcag cctgaatggc gaatgggacg    2460
cgccctgtag cggcgcatta agcgcggcgg gtgtggtggt tacgcgcagc gtgaccgcta    2520
cacttgccag cgccctagcg cccgctcctt tcgctttctt cccttccttt ctcgccacgt    2580
tcgccggctt tccccgtcaa gctctaaatc gggggctccc tttagggttc cgatttagtg    2640
ctttacggca cctcgacccc aaaaaacttg attagggtga tggttcacgt agtgggccat    2700
cgccctgata gacggttttt cgcccttttga cgttggagtc cacgttcttt aatagtggac    2760
tcttgttcca aactggaaca acactcaacc ctatctcggt ctattctttt gatttataag    2820 ggatttttgcc gatttcggcc tattggttaa aaaatgagct gatttaacaa aaatttaacg    2880
cgaattttaa caaatatta acgcttacaa tttaggtggc acttttcggg gaaatgtgcg    2940
cggaacccct atttgtttat ttttctaaat acattcaaat atgtatccgc tcatgagaca    3000
ataaccctga taaatgcttc aataatattg aaaaaggaag agtatgagta ttcaacattt    3060
ccgtgtcgcc cttattccct tttttgcggc attttgcctt cctgttttg ctcacccaga    3120 aacgctggtg aaagtaaaag atgctgaaga tcagttgggt gcacgagtgg gttacatcga    3180
actggatctc aacagcggta agatccttga gagttttcgc cccgaagaac gttttccaat    3240
gatgagcact tttaaagttc tgctatgtgg cgcggtatta tcccgtattg acgccgggca    3300
agagcaactc ggtcgccgca tacactattc tcagaatgac ttggttgagt actcaccagt    3360
cacagaaaag catcttacgg atggcatgac agtaagagaa ttatgcagtg ctgccataac    3420
catgagtgat aacactgcgg ccaacttact tctgacaacg atcggaggac cgaaggagct    3480
aaccgctttt ttgcacaaca tgggggatca tgtaactcgc cttgatcgtt gggaaccgga    3540
gctgaatgaa gccataccaa acgacgagcg tgacaccacg atgcctgtag caatggcaac    3600
aacgttgcgc aaactattaa ctggcgaact acttactcta gcttcccggc aacaattaat    3660
agactggatg gaggcggata aagttgcagg accacttctg cgctcggccc ttccggctgg    3720
ctggtttatt gctgataaat ctggagccgg tgagcgtggg tctcgcggta tcattgcagc    3780
actggggcca gatggtaagc cctcccgtat cgtagttatc tacacgacgg ggagtcaggc    3840
aactatggat gaacgaaata gacagatcgc tgagataggt gcctcactga ttaagcattg    3900
gtaactgtca gaccaagttt actcatatat actttagatt gatttaaaac ttcattttta    3960
atttaaaagg atctaggtga agatcctttt tgataatctc atgaccaaaa tcccttaacg    4020
tgagttttcg ttccactgag cgtcagaccc cgtagaaaag atcaaaggat cttcttgaga    4080 tcctttttttt ctgcgcgtaa tctgctgctt gcaaacaaaa aaaccaccgc taccagcggt    4140
ggtttgtttg ccggatcaag agctaccaac tcttttccg aaggtaactg gcttcagcag    4200
agcgcagata ccaaatactg tccttctagt gtagccgtag ttaggccacc acttcaagaa    4260
ctctgtagca ccgcctacat acctcgctct gctaatcctg ttaccagtgg ctgctgccag    4320
tggcgataag tcgtgtctta ccgggttgga ctcaagacga tagttaccgg ataaggcgca    4380
gcggtcgggc tgaacggggg gttcgtgcac acagcccagc ttggagcgaa cgacctacac    4440
cgaactgaga tacctacagc gtgagctatg agaaagcgcc acgcttcccg aagggagaaa    4500
ggcggacagg tatccggtaa gcggcagggt cggaacagga gagcgcacga gggagcttcc    4560 aggggggaaac gcctggtatc tttatagtcc tgtcgggttt cgccacctct gacttgagcg    4620
tcgatttttg tgatgctcgt caggggggcg gagcctatgg aaaaacgcca gcaacgcggc    4680 cttttttacgg ttcctggcct tttgctggcc ttttgctcac atgttctttc ctgcgttatc    4740
```

-continued

```
ccctgattct gtggataacc gtattaccgc ctttgagtga gctgataccg ctcgccgcag    4800
ccgaacgacc gagcgcagcg agtcagtgag cgaggaagcg gaagagcgcc caatacgcaa    4860
accgcctctc cccgcgcgtt ggccgattca ttaatgcagg tatcacgagg ccctttcgtc    4920
ttcac                                                                4925
```

<210> SEQ ID NO 135
<211> LENGTH: 4922
<212> TYPE: DNA
<213> ORGANISM: Artificial Sequence
<220> FEATURE:
<223> OTHER INFORMATION: Plasmid

<400> SEQUENCE: 135

```
ctcgagagcg ggcagtgagc gcaacgcaat taatgtgagt tagctcactc attaggcacc      60
ccaggcttta cactttatgc ttccggctcg tatgttgtgt ggaattgtga gcggataaca     120
atttcacaca gaattcatta agaggagaa attaaccatg aaatacctat tgcctacggc      180
agccgctggc ttgctgctgc tggcagctca gccggccatg gcgcaggtac agctgcagga    240
gtctggggga ggcgtggtcc agcctgggag gtccctgaga ctctcctgtg cagcctctgg    300
attctccttc agtaattatg gcatacactg gtccgccag gctccaggca aggggctgga     360
gtgggtggca cttatatcat atgatggaaa taagaaattc tatgcagact ccgtgaaggg    420
ccgattcgcc atctccagag acacttctaa gaatacggtg atctgcaaa tgaccagcct     480 gagacctgag gacacgtctt cagcgctgag ctcgaagact ggtcaccgtc tcctcagcct    540
ccaccaaggg cccaaagctt gaagaaggtg aattttcaga agcacgcgta tcctatgaac    600
tgactcagcc accctcggtg tcagtggccc caggacagac ggccatgatt acctgtgggg    660
gaaacaacat tggaagtaca accgtgcact ggtatcagca gaagccaggc caggcccctg    720
tgctggtcgt ctatgatgat aacgagcgac cctcagggat ccctgagcga ttctctggct    780
ccaactctgg gagcacggcc accctgacca tcaacagggt cgaagccggg gatgaggccg    840
actattattg tcaagtgtgg gatagtggta gtgatcatgt ggtattcggc ggagggacga    900
agctgaccgt cctaggtcag cccaaggctg ccccctcggt cactctgttc ccgccctcct    960
ctgcggccgc tggatcccat caccatcacc atcactagga caaaagctg atctcagaag    1020 aggacctaaa cggatccaaa gatatcagag ctgaaactgt tgaaagttgt ttagcaaaat    1080
cccatacaga aaattcattt actaacgtct ggaaagacga caaaacttta gatcgttacg    1140
ctaactatga gggctgtctg tggaatgcta caggcgttgt agtttgtact ggtgacgaaa    1200
ctcagtgtta cggtacatgg gttcctattg ggcttgctat ccctgaaaat gagggtggtg    1260
gctctgaggg tggcggttct gagggtggcg gttctgaggg tggcggtact aaacctcctg    1320
agtacggtga tacacctatt ccgggctata cttatatcaa ccctctcgac ggcacttatc    1380
cgcctggtac tgagcaaaac cccgctaatc ctaatccttc tcttgaggag tctcagcctc    1440
ttaatacttt catgtttcag aataataggt tccgaaatag cagggggca ttaactgttt    1500 atacgggcac tgttactcaa ggcactgacc ccgttaaaac ttattaccag tacactcctg    1560
tatcatcaaa agccatgtat gacgcttact ggaacggtaa attcagagac tgcgctttcc    1620
attctggctt taatgaggat ttatttgttt gtgaatatca aggccaatcg tctgacctgc    1680
ctcaacctcc tgtcaatgct ggcggcggct ctggtggtgg ttctggtggc ggctctgagg    1740
gtggtggctc tgagggtggc ggttctgagg gtggcggctc tgagggaggc ggttccggtg    1800
gtggctctgg ttccggtgat tttgattatg aaaagatggc aaacgctaat aagggggcta    1860
```

```
tgaccgaaaa tgccgatgaa aacgcgctac agtctgacgc taaaggcaaa cttgattctg    1920
tcgctactga ttacggtgct gctatcgatg gtttcattgg tgacgtttcc ggccttgcta    1980
atggtaatgg tgctactggt gattttgctg gctctaattc ccaaatggct caagtcggtg    2040
acggtgataa ttcacctttt atgaataatt ccgtcaata tttaccttcc ctccctcaat    2100
cggttgaatg tcgcccttt gtctttggcg ctggtaaacc atatgaattt tctattgatt    2160
gtgacaaaat aaacttattc cgtggtgtct ttgcgtttct tttatatgtt gccacctta    2220 tgtatgtatt ttctacgttt gctaacatac tgcgtaataa ggagtcttaa tgatctagag    2280
gcctgtgcta atgatcagct agcttgaggc atcaataaaa cgaaaggctc agtcgaaaga    2340
ctgggccttt cgttttatct gttgtttgtc ggttaacgtc gacctggcgt aatagcgaag    2400
aggcccgcac cgatcgccct tcccaacagt tgcgcagcct gaatggcgaa tgggacgcgc    2460
cctgtagcgg cgcattaagc gcggcgggtg tggtggttac gcgcagcgtg accgctacac    2520
ttgccagcgc cctagcgccc gctcctttcg ctttcttccc ttcctttctc gccacgttcg    2580
ccggctttcc ccgtcaagct ctaaatcggg gctccctt agggttccga tttagtgctt    2640
tacggcacct cgaccccaaa aaacttgatt agggtgatgg ttcacgtagt gggccatcgc    2700
cctgatagac ggttttcgc cctttgacgt tggagtccac gttctttaat agtggactct    2760
tgttccaaac tggaacaaca ctcaacccta tctcggtcta ttcttttgat ttataaggga    2820
ttttgccgat ttcggcctat tggttaaaaa atgagctgat ttaacaaaaa tttaacgcga    2880
attttaacaa aatattaacg cttacaattt aggtggcact tttcggggaa atgtgcgcgg    2940 aaccccctatt tgtttatttt tctaaataca ttcaaatatg tatccgctca tgagacaata    3000
accctgataa atgcttcaat aatattgaaa aaggaagagt atgagtattc aacatttccg    3060
tgtcgccctt attccctttt ttgcggcatt ttgccttcct gtttttgctc acccagaaac    3120
gctggtgaaa gtaaaagatg ctgaagatca gttgggtgca cgagtgggtt acatcgaact    3180
ggatctcaac agcggtaaga tccttgagag ttttcgcccc gaagaacgtt ttccaatgat    3240
gagcactttt aaagttctgc tatgtggcgc ggtattatcc cgtattgacg ccgggcaaga    3300
gcaactcggt cgccgcatac actattctca gaatgacttg gttgagtact caccagtcac    3360
agaaaagcat cttacggatg gcatgacagt aagagaatta tgcagtgctg ccataaccat    3420
gagtgataac actgcggcca acttacttct gacaacgatc ggaggaccga aggagctaac    3480
cgcttttttg cacaacatgg gggatcatgt aactcgcctt gatcgttggg aaccggagct    3540
gaatgaagcc ataccaaacg acgagcgtga caccacgatg cctgtagcaa tggcaacaac    3600
gttgcgcaaa ctattaactg gcgaactact tactctagct tcccggcaac aattaataga    3660
ctggatggag gcggataaag ttgcaggacc acttctgcgc tcggcccttc cggctggctg    3720
gtttattgct gataaatctg gagccggtga gcgtgggtct cgcggtatca ttgcagcact    3780
ggggccagat ggtaagccct cccgtatcgt agttatctac acgacgggga gtcaggcaac    3840
tatggatgaa cgaaatagac agatcgctga gataggtgcc tcactgatta agcattggta    3900
actgtcagac caagtttact catatatact ttagattgat ttaaaacttc attttaatt    3960 taaaaggatc taggtgaaga tccttttga taatctcatg accaaaatcc cttaacgtga    4020
gttttcgttc cactgagcgt cagacccgt agaaaagatc aaaggatctt cttgagatcc    4080 ttttttctg cgcgtaatct gctgcttgca acaaaaaaa ccaccgctac cagcggtggt    4140
ttgtttgccg gatcaagagc taccaactct ttttccgaag gtaactggct tcagcagagc    4200
```

```
gcagatacca aatactgtcc ttctagtgta gccgtagtta ggccaccact tcaagaactc      4260
tgtagcaccg cctacatacc tcgctctgct aatcctgtta ccagtggctg ctgccagtgg      4320
cgataagtcg tgtcttaccg ggttggactc aagacgatag ttaccggata aggcgcagcg      4380
gtcgggctga acgggggtt cgtgcacaca gcccagcttg gagcgaacga cctacaccga       4440
actgagatac ctacagcgtg agctatgaga aagcgccacg cttcccgaag ggagaaaggc      4500
ggacaggtat ccggtaagcg gcagggtcgg aacaggagag cgcacgaggg agcttccagg      4560
gggaaacgcc tggtatcttt atagtcctgt cgggtttcgc cacctctgac ttgagcgtcg      4620
atttttgtga tgctcgtcag gggggcgag cctatggaaa aacgccagca acgcggcctt       4680
tttacggttc ctggcctttt gctggccttt tgctcacatg ttctttcctg cgttatcccc      4740
tgattctgtg gataaccgta ttaccgcctt tgagtgagct gataccgctc gccgcagccg      4800
aacgaccgag cgcagcgagt cagtgagcga ggaagcggaa gagcgcccaa tacgcaaacc      4860
gcctctcccc gcgcgttggc cgattcatta atgcaggtat cacgaggccc tttcgtcctc      4920
ac                                                                     4922

<210> SEQ ID NO 136
<211> LENGTH: 4925
<212> TYPE: DNA
<213> ORGANISM: Artificial Sequence
<220> FEATURE:
<223> OTHER INFORMATION: Plasmid

<400> SEQUENCE: 136
ctcgagagcg ggcagtgagc gcaacgcaat taatgtgagt tagctcactc attaggcacc        60
ccaggcttta cactttatgc ttccggctcg tatgttgtgt ggaattgtga gcggataaca       120
atttcacaca gaattcatta agaggagaaa attaaccatg aaataccata tgcctacggc       180
agccgctggc ttgctgctgc tggcagctca gccggccatg gcgcaggtgc agctgcagga       240
gtctggggga ggcttggtac agcctggggg gtccctgaga ctctcctgtg cagcctctgg       300
attcatgttt agcaggtatg ccatgagctg ggtccgccag gctccaggga aggggccaga       360
gtgggtctca ggtattagtg gtagtggtgg tagtacatac tacgcagact ccgtgaaggg       420
ccggttcacc gtctccagag acaattccaa gaacacgctg tatctgcaaa tgaacagcct       480
gagagccgag gacacgtctt cagcgctgag ctcgaagact ggtcaccgtc tcctcaggga       540
gtgcatccgc cccaaagctt gaagaaggtg aattttcaga agcacgcgta tctgaactga       600
ctcaggaccc tgctgtgtct gtggccttgg gacagacagt caggatcaca tgccaaggag       660
acagcctcag aaacttttat gcaagctggt accagcagaa gccaggacag gcccctactc       720
ttgtcatcta tggtttaagt aaaaggccct cagggatccc agaccgattc tctgcctcca       780
gctcaggaaa cacagcttcc ttgaccatca ctggggctca ggcggaagat gaggctgact       840
attactgtaa ctcccgggac agaagtggta atcatgtaaa tgtgctattc ggcggaggga       900
ccaagctgac cgtcctacgt cagcccaagg ctgccccctc ggtcactctg ttcccgccct      960
cttctgcggc cgctggatcc catcaccatc accatcacta ggaacaaaag ctgatctcag      1020
aagaggacct aaacggatcc aaagatatca gagctgaaac tgttgaaagt tgtttagcaa      1080
aatcccatac agaaaattca tttactaacg tctggaaaga cgacaaaact ttagatcgtt      1140
acgctaacta tgagggctgt ctgtggaatg ctacaggcgt tgtagtttgt actggtgacg      1200
aaactcagtg ttacggtaca tgggttccta ttgggcttgc tatccctgaa aatgagggtg      1260
gtggctctga gggtggcggt tctgagggtg gcggttctga gggtggcggt actaaacctc      1320
```

```
ctgagtacgg tgatacacct attccgggct atacttatat caaccctctc gacggcactt   1380
atccgcctgg tactgagcaa accccgcta atcctaatcc ttctcttgag gagtctcagc   1440
ctcttaatac tttcatgttt cagaataata ggttccgaaa taggcagggg gcattaactg   1500
tttatacggg cactgttact caaggcactg accccgttaa aacttattac cagtacactc   1560
ctgtatcatc aaaagccatg tatgacgctt actggaacgg taaattcaga gactgcgctt   1620
tccattctgg ctttaatgag gatttatttg tttgtgaata tcaaggccaa tcgtctgacc   1680
tgcctcaacc tcctgtcaat gctggcgcg gctctggtgg tggttctggt ggcggctctg   1740
agggtggtgg ctctgagggt ggcggttctg agggtggcgg ctctgaggga ggcggttccg   1800
gtggtggctc tggttccggt gattttgatt atgaaaagat ggcaaacgct aataaggggg   1860
ctatgaccga aaatgccgat gaaaacgcgc tacagtctga cgctaaaggc aaacttgatt   1920
ctgtcgctac tgattacggt gctgctatcg atggtttcat tggtgacgtt tccggccttg   1980
ctaatggtaa tggtgctact ggtgattttg ctggctctaa ttcccaaatg gctcaagtcg   2040
gtgacggtga taattcacct ttaatgaata atttccgtca atatttacct tccctccctc   2100
aatcggttga atgtcgccct tttgtctttg gcgctggtaa accatatgaa ttttctattg   2160
attgtgacaa aataaactta ttccgtggtg tctttgcgtt tcttttatat gttgccacct   2220
ttatgtatgt attttctacg tttgctaaca tactgcgtaa taaggagtct taatgatcta   2280
gaggcctgtg ctaatgatca gctagcttga ggcatcaata aaacgaaagg ctcagtcgaa   2340
agactgggcc tttcgtttta tctgttgttt gtcggttaac gtcgacctgg cgtaatagcg   2400
aagaggcccg caccgatcgc ccttcccaac agttgcgcag cctgaatggc gaatgggacg   2460
cgccctgtag cggcgcatta agcgcggcgg gtgtggtggt tacgcgcagc gtgaccgcta   2520
cacttgccag cgccctagcg cccgctcctt tcgctttctt cccttccttt ctcgccacgt   2580
tcgccggctt tccccgtcaa gctctaaatc ggggctccc tttagggttc cgatttagtg   2640
ctttacggca cctcgacccc aaaaaacttg attagggtga tggttcacgt agtgggccat   2700
cgccctgata gacggttttt cgccctttga cgttggagtc cacgttcttt aatagtggac   2760
tcttgttcca aactggaaca acactcaacc ctatctcggt ctattctttt gatttataag   2820
ggattttgcc gatttcggcc tattggttaa aaaatgagct gatttaacaa aaatttaacg   2880
cgaattttaa caaaatatta acgcttacaa tttaggtggc acttttcggg gaaatgtgcg   2940
cggaacccct atttgtttat ttttctaaat acattcaaat atgtatccgc tcatgagaca   3000
ataaccctga taaatgcttc aataatattg aaaaaggaag agtatgagta ttcaacattt   3060
ccgtgtcgcc cttattccct tttttgcggc attttgcctt cctgttttg ctcacccaga   3120
aacgctggtg aaagtaaaag atgctgaaga tcagttgggt gcacgagtgg gttacatcga   3180
actggatctc aacagcggta agatccttga gagttttcgc cccgaagaac gttttccaat   3240
gatgagcact tttaaagttc tgctatgtgg cgcggtatta tcccgtattg acgccgggca   3300
agagcaactc ggtcgccgca tacactattc tcagaatgac ttggttgagt actcaccagt   3360
cacagaaaag catcttacgg atggcatgac agtaagagaa ttatgcagtg ctgccataac   3420
catgagtgat aacactgcgg ccaacttact tctgacaacg atcggaggac cgaaggagct   3480
aaccgctttt ttgcacaaca tgggggatca tgtaactcgc cttgatcgtt gggaaccgga   3540
gctgaatgaa gccataccaa acgacgagcg tgacaccacg atgcctgtag caatggcaac   3600
aacgttgcgc aaactattaa ctggcgaact acttactcta gcttcccggc aacaattaat   3660
```

-continued

```
agactggatg gaggcggata aagttgcagg accacttctg cgctcggccc ttccggctgg   3720
ctggtttatt gctgataaat ctggagccgg tgagcgtggg tctcgcggta tcattgcagc   3780
actggggcca gatggtaagc cctcccgtat cgtagttatc tacacgacgg ggagtcaggc   3840
aactatggat gaacgaaata gacagatcgc tgagataggt gcctcactga ttaagcattg   3900
gtaactgtca gaccaagttt actcatatat actttagatt gatttaaaac ttcattttta   3960
atttaaaagg atctaggtga agatccttttt tgataatctc atgaccaaaa tcccttaacg   4020
tgagttttcg ttccactgag cgtcagaccc cgtagaaaag atcaaggat cttcttgaga    4080 tcctttttttt ctgcgcgtaa tctgctgctt gcaaacaaaa aaaccaccgc taccagcggt   4140
ggtttgtttg ccggatcaag agctaccaac tctttttccg aaggtaactg gcttcagcag   4200
agcgcagata ccaaatactg tccttctagt gtagccgtag ttaggccacc acttcaagaa   4260
ctctgtagca ccgcctacat acctcgctct gctaatcctg ttaccagtgg ctgctgccag   4320
tggcgataag tcgtgtctta ccgggttgga ctcaagacga tagttaccgg ataaggcgca   4380
gcggtcgggc tgaacggggg gttcgtgcac acagcccagc ttggagcgaa cgacctacac   4440
cgaactgaga tacctacagc gtgagctatg agaaagcgcc acgcttcccg aagggagaaa   4500
ggcggacagg tatccggtaa gcggcagggt cggaacagga gagcgcacga gggagcttcc   4560
agggggaaac gcctggtatc tttatagtcc tgtcgggttt cgccacctct gacttgagcg   4620
tcgatttttg tgatgctcgt caggggggcg gagcctatgg aaaaacgcca gcaacgcggc   4680
ctttttacgg ttcctggcct tttgctggcc ttttgctcac atgttctttc ctgcgttatc   4740
ccctgattct gtggataacc gtattaccgc ctttgagtga gctgataccg ctcgccgcag   4800
ccgaacgacc gagcgcagcg agtcagtgag cgaggaagcg gaagagcgcc caatacgcaa   4860
accgcctctc cccgcgcgtt ggccgattca ttaatgcagg tatcacgagg ccctttcgtc   4920
ctcac                                                              4925
```

<210> SEQ ID NO 137
<211> LENGTH: 31
<212> TYPE: DNA
<213> ORGANISM: Artificial Sequence
<220> FEATURE:
<223> OTHER INFORMATION: Synthetic

<400> SEQUENCE: 137

```
aatgcaggta tcacgaggcc ctttcgtctt c                                 31
```

<210> SEQ ID NO 138
<211> LENGTH: 34
<212> TYPE: DNA
<213> ORGANISM: Artificial Sequence
<220> FEATURE:
<223> OTHER INFORMATION: Synthetic

<400> SEQUENCE: 138

```
tactacgaag acgcctcatc cccggcttcg accc                              34
```

<210> SEQ ID NO 139
<211> LENGTH: 37
<212> TYPE: DNA
<213> ORGANISM: Artificial Sequence
<220> FEATURE:
<223> OTHER INFORMATION: Synthetic

<400> SEQUENCE: 139

```
tactacgaag actgaccgtc ctacgtcagc ccaaggc                           37
```

<210> SEQ ID NO 140
<211> LENGTH: 37
<212> TYPE: DNA
<213> ORGANISM: Artificial Sequence
<220> FEATURE:
<223> OTHER INFORMATION: Synthetic

<400> SEQUENCE: 140
tactacgaag actgaccgtc ctasgtcagc ccaaggc                              37

<210> SEQ ID NO 141
<211> LENGTH: 39
<212> TYPE: DNA
<213> ORGANISM: Artificial Sequence
<220> FEATURE:
<223> OTHER INFORMATION: Synthetic

<400> SEQUENCE: 141
cagctctgat atctttggat ccgtttaggt cttcttctg                            39

<210> SEQ ID NO 142
<211> LENGTH: 32
<212> TYPE: DNA
<213> ORGANISM: Artificial Sequence
<220> FEATURE:
<223> OTHER INFORMATION: Synthetic

<400> SEQUENCE: 142
tgaggcgtct tcagcgctga gctcgaagac tg                                   32

<210> SEQ ID NO 143
<211> LENGTH: 32
<212> TYPE: DNA
<213> ORGANISM: Artificial Sequence
<220> FEATURE:
<223> OTHER INFORMATION: Synthetic

<400> SEQUENCE: 143
cggtcagtct tcgagctcag cgctgaagac gc                                   32

<210> SEQ ID NO 144
<211> LENGTH: 36
<212> TYPE: DNA
<213> ORGANISM: Artificial Sequence
<220> FEATURE:
<223> OTHER INFORMATION: Synthetic

<400> SEQUENCE: 144
agcctggagc tctaaaaagc gtgctgctga acagta                               36

<210> SEQ ID NO 145
<211> LENGTH: 36
<212> TYPE: DNA
<213> ORGANISM: Artificial Sequence
<220> FEATURE:
<223> OTHER INFORMATION: Synthetic

<400> SEQUENCE: 145
cgactggagc tcgaacacgg ctcactttta ccttca                               36

<210> SEQ ID NO 146
<211> LENGTH: 64
<212> TYPE: DNA
<213> ORGANISM: Artificial Sequence
<220> FEATURE:

<223> OTHER INFORMATION: Synthetic
<220> FEATURE:
<221> NAME/KEY: misc_feature
<222> LOCATION: (30)..(31)
<223> OTHER INFORMATION: n is a, c, g, or t

<400> SEQUENCE: 146
atgaggccga ctattattgt caagtgtggn nkgtggtatt cggcggaggg acgaagctga    60
ccgt                                                                64

<210> SEQ ID NO 147
<211> LENGTH: 64
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (30)..(31)
<223> OTHER INFORMATION: n is a, c, g, or t

<400> SEQUENCE: 147
atgaggccga ctattattgt caagtgtggn nkgtggtatt cggcggaggg acgaagctga    60
ccgt                                                                64

<210> SEQ ID NO 148
<211> LENGTH: 64
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (30)..(31)
<223> OTHER INFORMATION: n is a, c, g, or t

<400> SEQUENCE: 148
atgaggccga ctattattgt caagtgtggn nkgtggtatt cggcggaggg acgaagctga    60
ccgt                                                                64

<210> SEQ ID NO 149
<211> LENGTH: 39
<212> TYPE: DNA
<213> ORGANISM: Artificial Sequence
<220> FEATURE:
<223> OTHER INFORMATION: Synthetic

<400> SEQUENCE: 149
tactacgaag acgatgaggc cgactattat tgtcaagtg                           39

<210> SEQ ID NO 150
<211> LENGTH: 39
<212> TYPE: DNA
<213> ORGANISM: Artificial Sequence
<220> FEATURE:
<223> OTHER INFORMATION: Synthetic

<400> SEQUENCE: 150
tactacgaag acgacggtca gcttcgtccc tccgccgaa                           39

<210> SEQ ID NO 151
<211> LENGTH: 64
<212> TYPE: DNA
<213> ORGANISM: Artificial Sequence
<220> FEATURE:
<223> OTHER INFORMATION: Synthetic

```
<220> FEATURE:
<221> NAME/KEY: misc_feature
<222> LOCATION: (30)..(31)
<223> OTHER INFORMATION: n is a, c, g, or t

<400> SEQUENCE: 151
atgaggctga ctattactgt aactcccggn nkgtgctatt cggcggaggg accaagctga      60
ccgt                                                                   64

<210> SEQ ID NO 152
<211> LENGTH: 64
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (30)..(31)
<223> OTHER INFORMATION: n is a, c, g, or t

<400> SEQUENCE: 152
atgaggctga ctattactgt aactcccggn nkgtgctatt cggcggaggg accaagctga      60
ccgt                                                                   64

<210> SEQ ID NO 153
<211> LENGTH: 64
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (30)..(31)
<223> OTHER INFORMATION: n is a, c, g, or t

<400> SEQUENCE: 153
atgaggctga ctattactgt aactcccggn nkgtgctatt cggcggaggg accaagctga      60
ccgt                                                                   64

<210> SEQ ID NO 154
<211> LENGTH: 39
<212> TYPE: DNA
<213> ORGANISM: Artificial Sequence
<220> FEATURE:
<223> OTHER INFORMATION: Synthetic

<400> SEQUENCE: 154
tactacgaag acgatgaggc tgactattac tgtaactcc                             39

<210> SEQ ID NO 155
<211> LENGTH: 39
<212> TYPE: DNA
<213> ORGANISM: Artificial Sequence
<220> FEATURE:
<223> OTHER INFORMATION: Synthetic

<400> SEQUENCE: 155
tactacgaag acgacggtca gcttggtccc tccgccgaa                             39

<210> SEQ ID NO 156
<211> LENGTH: 32
<212> TYPE: DNA
<213> ORGANISM: Artificial Sequence
<220> FEATURE:
<223> OTHER INFORMATION: Synthetic
```

<400> SEQUENCE: 156
tactacgaag acgatgaggc tgaytattac tg					32

<210> SEQ ID NO 157
<211> LENGTH: 33
<212> TYPE: DNA
<213> ORGANISM: Artificial Sequence
<220> FEATURE:
<223> OTHER INFORMATION: Synthetic

<400> SEQUENCE: 157
tactacgaag acgacggtca gcttggtccc tcc					33

<210> SEQ ID NO 158
<211> LENGTH: 5612
<212> TYPE: DNA
<213> ORGANISM: human pREFAB9/MB9 plasmid

<400> SEQUENCE: 158

| | | | | | |
|---|---|---|---|---|---|
| ctcgagagcg | ggcagtgagc | gcaacgcaat | taatgtgagt | tagctcactc | attaggcacc | 60 |
| ccaggcttta | cactttatgc | tcccggctcg | tatgttgtgt | ggaattgtga | gcggataaca | 120 |
| atttcacaca | gaattcatta | aagaggagaa | attaaccatg | aagtacctct | taccaaccgc | 180 |
| agcggctggt | ttactgctcc | tggcggctca | gccggcaatg | gcacaggctg | tgctgactca | 240 |
| gccgccctcg | gtgtcagtgg | ccccaggaca | gacggccagg | attacctgtg | ggggaaacaa | 300 |
| cattggaagt | aaaagtgtgc | agtggtacca | gcagaagcca | ggccaggccc | ctgtgctggt | 360 |
| cgtctatgat | gatagcgacc | ggccctcagg | gatccctgag | cgattctctg | gctccaactc | 420 |
| tgggaacatg | gccaccctga | ccatcagcag | ggtcgaagcc | ggggatgagg | ccgactatta | 480 |
| ctgtcaggtg | tgggatagta | gtagtgatca | tgtggtattc | ggcggaggga | ccaagctgac | 540 |
| cgtcctaggt | cagcccaagg | ctgccccctc | ggtcactctg | ttcccgccct | cctctgagga | 600 |
| gcttcaagcc | aacaaggcca | cactggtgtg | tctcataagt | gacttctacc | cgggagccgt | 660 |
| gacagtggcc | tggaaggcag | atagcagccc | cgtcaaggcg | ggagtggaga | ccaccacacc | 720 |
| ctccaaacaa | agcaacaaca | agtacgcggc | cagcagctat | ctgagcctga | cgcctgagca | 780 |
| gtggaagtcc | cacagaagct | acagctgcca | ggtcacgcat | gaagggagca | ccgtggagaa | 840 |
| gacagtggcc | cctacagaat | gttcagaaca | aaagcttatc | tcagaagagg | acctaaacta | 900 |
| atgaacgcgt | tattaaagag | gagaaattaa | ccatgaaata | cctattgcct | acggcagccg | 960 |
| ctggcttgct | gctgctggca | gcacaaccgg | ccatggcgga | agtgcagctg | gtgcagtctg | 1020 |
| gagctgaggt | gaataagcct | ggggcctcag | tgaaggtctc | ctgcaaggct | tctggataca | 1080 |
| ccttcaccgg | ctactatatg | cactgggtgc | acaggcccc | tggacaaggg | cttgagtgga | 1140 |
| tgggatggat | caaccctaac | agtggtggca | caaactatgc | acagaagttt | cagggctggg | 1200 |
| tcaccatgac | cagggacacg | tccatcagca | ccgcctacat | ggagctgagc | aggctgagat | 1260 |
| ctgacgacac | ggccgtgtat | tactgtgcga | gaggccgtgc | tttgtataac | cggaacgacc | 1320 |
| ggtcccccaa | ctggttcgac | ccctgggcc | agggaaccct | ggtcaccgtc | tcctcagcct | 1380 |
| ccaccaaggg | cccatcggtc | ttccccctgg | caccctcctc | caagagcacc | tctggggca | 1440 |
| cagcggccct | gggctgcctg | gtcaaggact | acttccccga | accggtgacg | gtgtcgtgga | 1500 |
| actcaggcgc | cctgaccagc | ggcgtgcaca | ccttcccggc | tgtcctacag | tcctcaggac | 1560 |
| tctactccct | cagcagcgtg | gtgaccgtgc | cctccagcag | cttgggcacc | cagacctaca | 1620 |
| tctgcaacgt | gaatcacaag | cccagcaaca | ccaaggtgga | caagaaagtt | gagcccaaat | 1680 |

```
cttgtgcggc cgctggatcc catcaccatc accatcacta gggatccaaa gatatcagag   1740
ctgaaactgt tgaaagttgt ttagcaaaat cccatacaga aaattcattt actaacgtct   1800
ggaaagacga caaaacttta gatcgttacg ctaactatga gggctgtctg tggaatgcta   1860
caggcgttgt agtttgtact ggtgacgaaa ctcagtgtta cggtacatgg gttcctattg   1920
ggcttgctat ccctgaaaat gagggtggtg gctctgaggg tggcggttct gagggtggcg   1980
gttctgaggg tggcggtact aaacctcctg agtacggtga tacacctatt ccgggctata   2040
cttatatcaa ccctctcgac ggcacttatc cgcctggtac tgagcaaaac cccgctaatc   2100
ctaatccttc tcttgaggag tctcagcctc ttaatacttt catgtttcag aataataggt   2160
tccgaaatag caggggggca ttaactgttt atacgggcac tgttactcaa ggcactgacc   2220
ccgttaaaac ttattaccag tacactcctg tatcatcaaa agccatgtat gacgcttact   2280
ggaacggtaa attcagagac tgcgctttcc attctggctt taatgaggat ttatttgttt   2340
gtgaatatca aggccaatcg tctgacctgc ctcaacctcc tgtcaatgct ggcggcggct   2400
ctggtggtgg ttctggtggc ggctctgagg gtggtggctc tgagggtggc ggttctgagg   2460
gtggcggctc tgagggaggc ggttccggtg gtggctctgg ttccggtgat tttgattatg   2520
aaaagatggc aaacgctaat aagggggcta tgaccgaaaa tgccgatgaa aacgcgctac   2580
agtctgacgc taaaggcaaa cttgattctg tcgctactga ttacggtgct gctatcgatg   2640
gtttcattgg tgacgtttcc ggccttgcta atggtaatgg tgctactggt gattttgctg   2700
gctctaattc ccaaatggct caagtcgtga cggtgataa ttcaccttta atgaataatt   2760
tccgtcaata tttaccttcc ctccctcaat cggttgaatg tcgcccttt gtctttggcg   2820 ctggtaaacc atatgaattt tctattgatt gtgacaaaat aaacttattc cgtggtgtct   2880
ttgcgtttct tttatatgtt gccacctta tgtatgtatt ttctacgttt gctaacatac   2940
tgcgtaataa ggagtcttaa tgatctagag gcctgtgcta atgatcagct agcttgaggc   3000
atcaataaaa cgaaaggctc agtcgaaaga ctgggccttt cattttatct gttgtttgtc   3060
ggttaacgtc gacctggcgt aatagcgaag aggcccgcac cgatcgccct tcccaacagt   3120
tgcgcagcct gaatggcgaa tgggacgcgc cctgtagcgg cgcattaagc gcggcgggtg   3180
tggtggttac gcgcagcgtg accgctacac ttgccagcgc cctagcgccc gctcctttcg   3240
ctttcttccc ttcctttctc gccacgttcg ccggcttttc ccgtcaagct ctaaatcggg   3300
ggctcccttt agggttccga tttagtgctt tacggcacct cgaccccaaa aaacttgatt   3360
agggtgatgg ttcacgtagt gggccatcgc cctgatagac ggtttttcgc cctttgacgt   3420
tggagtccac gttctttaat agtggactct tgttccaaac tggaacaaca ctcaacccta   3480
tctcggtcta ttcttttgat ttataaggga ttttgccgat ttcggcctat tggttaaaaa   3540
atgagctgat ttaacaaaaa tttaacgcga attttaacaa aatattaacg cttacaattt   3600
aggtggcact tttcggggaa atgtgcgcgg aacccctatt tgtttatttt tctaaataca   3660
ttcaaatatg tatccgctca tgagacaata accctgataa atgcttcaat aatattgaaa   3720
aaggaagagt atgagtattc aacatttccg tgtcgccctt attcccttt ttgcggcatt   3780 ttgccttcct gtttttgctc acccagaaac gctggtgaaa gtaaaagatg ctgaagatca   3840
gttgggtgca cgagtgggtt acatcgaact ggatctcaac agcggtaaga tccttgagag   3900
ttttcgcccc gaagaacgtt ttccaatgat gagcactttt aaagttctgc tatgtggcgc   3960
ggtattatcc cgtattgacg ccgggcaaga gcaactcggt cgccgcatac actattctca   4020
```

```
gaatgacttg gttgagtact caccagtcac agaaaagcat cttacggatg gcatgacagt    4080
aagagaatta tgcagtgctg ccataaccat gagtgataac actgcggcca acttacttct    4140
gacaacgatc ggaggaccga aggagctaac cgcttttttg cacaacatgg gggatcatgt    4200
aactcgcctt gatcgttggg aaccggagct gaatgaagcc ataccaaacg acgagcgtga    4260
caccacgatg cctgtagcaa tggcaacaac gttgcgcaaa ctattaactg gcgaactact    4320
tactctagct tcccggcaac aattaataga ctggatggag gcggataaag ttgcaggacc    4380
acttctgcgc tcggcccttc cggctggctg gtttattgct gataaatctg gagccggtga    4440
gcgtgggtct cgcggtatca ttgcagcact ggggccagat ggtaagccct cccgtatcgt    4500
agttatctac acgacgggga gtcaggcaac tatggatgaa cgaaatagac agatcgctga    4560
gataggtgcc tcactgatta agcattggta actgtcagac caagtttact catatatact    4620
ttagattgat ttaaaacttc attttttaatt taaaaggatc taggtgaaga tcctttttga    4680
taatctcatg accaaaatcc cttaacgtga gttttcgttc cactgagcgt cagaccccgt    4740
agaaaagatc aaaggatctt cttgagatcc ttttttttctg cgcgtaatct gctgcttgca    4800
aacaaaaaaa ccaccgctac cagcggtggt ttgtttgccg gatcaagagc taccaactct    4860
ttttccgaag gtaactggct tcagcagagc gcagatacca atactgtcc ttctagtgta    4920 gccgtagtta ggccaccact tcaagaactc tgtagcaccg cctacatacc tcgctctgct    4980
aatcctgtta ccagtggctg ctgccagtgg cgataagtcg tgtcttaccg ggttggactc    5040
aagacgatag ttaccggata aggcgcagcg gtcgggctga acggggggtt cgtgcacaca    5100
gcccagcttg gagcgaacga cctacaccga actgagatac ctacagcgtg agctatgaga    5160
aagcgccacg cttcccgaag ggagaaaggc ggacaggtat ccggtaagcg cagggtcgg    5220 aacaggagag cgcacgaggg agcttccagg gggaaacgcc tggtatcttt atagtcctgt    5280
cgggtttcgc cacctctgac ttgagcgtcg atttttgtga tgctcgtcag ggggcggag    5340 cctatggaaa aacgccagca acgcggcctt tttacggttc ctggccttt gctggccttt    5400 tgctcacatg ttctttcctg cgttatcccc tgattctgtg ataaccgta ttaccgcctt    5460 tgagtgagct gataccgctc gccgcagccg aacgaccgag cgcagcgagt cagtgagcga    5520
ggaagcggaa gagcgcccaa tacgcaaacc gcctctcccc gcgcgttggc cgattcatta    5580
atgcaggtat cacgaggccc tttcgtcctc ac                                 5612
```

<210> SEQ ID NO 159
<211> LENGTH: 282
<212> TYPE: PRT
<213> ORGANISM: MB9 scFv Translation Recombinant Human Antibody Fragment

<400> SEQUENCE: 159

Met Ala Glu Val Gln Leu Val Gln Ser Gly Ala Glu Val Asn Lys Pro
1               5                   10                  15

Gly Ala Ser Val Lys Val Ser Cys Lys Ala Ser Gly Tyr Thr Phe Thr
                20                  25                  30

Gly Tyr Tyr Met His Trp Val Arg Gln Ala Pro Gly Gln Gly Leu Glu
            35                  40                  45

Trp Met Gly Trp Ile Asn Pro Asn Ser Gly Gly Thr Asn Tyr Ala Gln
        50                  55                  60

Lys Phe Gln Gly Trp Val Thr Met Thr Arg Asp Thr Ser Ile Ser Thr
65                  70                  75                  80

Ala Tyr Met Glu Leu Ser Arg Leu Arg Ser Asp Asp Thr Ala Val Tyr
                85                  90                  95

```
Tyr Cys Ala Arg Gly Arg Ala Leu Tyr Asn Arg Asn Asp Arg Ser Pro
            100                 105                 110

Asn Trp Phe Asp Pro Trp Gly Gln Gly Thr Leu Val Thr Val Ser Ser
        115                 120                 125

Gly Ser Ala Ser Ala Pro Thr Leu Lys Leu Glu Glu Gly Glu Phe Ser
    130                 135                 140

Glu Ala Arg Val Gln Ala Val Leu Thr Gln Pro Pro Ser Val Ser Val
145                 150                 155                 160

Ala Pro Gly Gln Thr Ala Arg Ile Thr Cys Gly Gly Asn Asn Ile Gly
                165                 170                 175

Ser Lys Ser Val Gln Trp Tyr Gln Gln Lys Pro Gly Gln Ala Pro Val
            180                 185                 190

Leu Val Val Tyr Asp Asp Ser Asp Arg Pro Ser Gly Ile Pro Glu Arg
        195                 200                 205

Phe Ser Gly Ser Asn Ser Gly Asn Met Ala Thr Leu Thr Ile Ser Arg
    210                 215                 220

Val Glu Ala Gly Asp Glu Ala Asp Tyr Tyr Cys Gln Val Trp Asp Ser
225                 230                 235                 240

Ser Ser Asp His Val Val Phe Gly Gly Gly Thr Lys Leu Thr Val Leu
                245                 250                 255

Gly Gln Pro Lys Ala Ala Pro Ser Val Thr Leu Phe Pro Pro Ser Ala
            260                 265                 270

Ala Ala Gly Ser His His His His His His
        275                 280

<210> SEQ ID NO 160
<211> LENGTH: 29
<212> TYPE: PRT
<213> ORGANISM: mb9 SCfV (SCfV21)

<400> SEQUENCE: 160

Val Thr Val Ser Ser Gly Ser Ala Ser Ala Pro Thr Leu Lys Leu Glu
1               5                   10                  15

Glu Gly Glu Phe Ser Glu Ala Arg Val Gln Ala Val Leu
            20                  25

<210> SEQ ID NO 161
<211> LENGTH: 11
<212> TYPE: PRT
<213> ORGANISM: MB9 diabody (scFv3)

<400> SEQUENCE: 161

Val Thr Val Ser Ser Arg Val Gln Ala Val Leu
1               5                   10

<210> SEQ ID NO 162
<211> LENGTH: 11
<212> TYPE: PRT
<213> ORGANISM: Artificial Sequence
<220> FEATURE:
<223> OTHER INFORMATION: peptide derived from random synthetic DNA

<400> SEQUENCE: 162

Cys Ala Arg Arg Tyr Arg Val Gly Phe Asp Tyr
1               5                   10

<210> SEQ ID NO 163
<211> LENGTH: 21
<212> TYPE: PRT
```

<213> ORGANISM: Artificial Sequence
<220> FEATURE:
<223> OTHER INFORMATION: peptide derived from random synthetic DNA

<400> SEQUENCE: 163

Cys Ala Arg Gly Ala Thr Tyr Thr Ser Arg Ser Asp Val Pro Asp Gln
1               5                   10                  15

Thr Ser Phe Asp Tyr
            20

<210> SEQ ID NO 164
<211> LENGTH: 21
<212> TYPE: PRT
<213> ORGANISM: Artificial Sequence
<220> FEATURE:
<223> OTHER INFORMATION: peptide derived from random synthetic DNA

<400> SEQUENCE: 164

Cys Ala Arg Asp Asp Leu Ala Tyr Cys Arg Gly Asp Cys Ser Gly Arg
1               5                   10                  15

Phe Ala Phe Asp Ile
            20

<210> SEQ ID NO 165
<211> LENGTH: 13
<212> TYPE: PRT
<213> ORGANISM: Artificial Sequence
<220> FEATURE:
<223> OTHER INFORMATION: peptide derived from random synthetic DNA

<400> SEQUENCE: 165

Cys Ala Arg Arg Phe Ser Ile Ser Arg Ala Phe Asp Tyr
1               5                   10

<210> SEQ ID NO 166
<211> LENGTH: 13
<212> TYPE: PRT
<213> ORGANISM: Artificial Sequence
<220> FEATURE:
<223> OTHER INFORMATION: peptide derived from random synthetic DNA

<400> SEQUENCE: 166

Cys Ala Arg Arg Trp Gly Lys Ala Arg Ser Phe Asp Tyr
1               5                   10

<210> SEQ ID NO 167
<211> LENGTH: 22
<212> TYPE: PRT
<213> ORGANISM: Artificial Sequence
<220> FEATURE:
<223> OTHER INFORMATION: peptide derived from random synthetic DNA

<400> SEQUENCE: 167

Cys Ala Lys Glu Leu Glu Ala Tyr Cys Arg Gly Asp Cys Tyr Pro Pro
1               5                   10                  15

Tyr Tyr Gly Met Asp Val
            20

<210> SEQ ID NO 168
<211> LENGTH: 19
<212> TYPE: PRT
<213> ORGANISM: Artificial Sequence
<220> FEATURE:
<223> OTHER INFORMATION: peptide derived from random synthetic DNA

<400> SEQUENCE: 168

```
Cys Ala Arg Asp Leu Phe Arg Gly Arg Gly Asp Tyr Gly Asp Tyr Gly
1               5                   10                  15

Met Asp Val

<210> SEQ ID NO 169
<211> LENGTH: 21
<212> TYPE: PRT
<213> ORGANISM: Artificial Sequence
<220> FEATURE:
<223> OTHER INFORMATION: peptide derived from random synthetic DNA

<400> SEQUENCE: 169

Cys Ala Arg Thr Tyr Tyr Tyr Asp Ser Arg Thr Asp Arg Arg Pro Pro
1               5                   10                  15

His Ala Phe Asp Ile
            20

<210> SEQ ID NO 170
<211> LENGTH: 16
<212> TYPE: PRT
<213> ORGANISM: Artificial Sequence
<220> FEATURE:
<223> OTHER INFORMATION: peptide derived from random synthetic DNA

<400> SEQUENCE: 170

Cys Leu Leu Tyr Tyr Gly Gly Gly Gln Gln Gly Val Phe Gly Gly Gly
1               5                   10                  15

<210> SEQ ID NO 171
<211> LENGTH: 14
<212> TYPE: PRT
<213> ORGANISM: Artificial Sequence
<220> FEATURE:
<223> OTHER INFORMATION: peptide derived from random synthetic DNA

<400> SEQUENCE: 171

Cys Leu Leu Tyr Tyr Gly Gly Ala Trp Val Phe Gly Gly Gly
1               5                   10
```